United States Patent
Kang et al.

(10) Patent No.: US 11,069,859 B2
(45) Date of Patent: Jul. 20, 2021

(54) FLUORENE-BASED COMPOUND, ORGANIC LIGHT-EMITTING DEVICE USING SAME AND METHOD FOR PREPARING SAME

(71) Applicant: LG Chem, Ltd., Seoul (KR)

(72) Inventors: Sungkyoung Kang, Daejeon (KR); Jaesoon Bae, Daejeon (KR); Jaechol Lee, Daejeon (KR); Seokhee Yoon, Daejeon (KR); Donggu Lee, Daejeon (KR); Yongwook Kim, Daejeon (KR); Ho Gyu Lee, Daejeon (KR)

(73) Assignee: LG Chem, Ltd.

( * ) Notice: Subject to any disclaimer, the term of this patent is extended or adjusted under 35 U.S.C. 154(b) by 319 days.

(21) Appl. No.: 16/337,997

(22) PCT Filed: Jan. 8, 2018

(86) PCT No.: PCT/KR2018/000347
§ 371 (c)(1),
(2) Date: Mar. 29, 2019

(87) PCT Pub. No.: WO2018/159937
PCT Pub. Date: Sep. 7, 2018

(65) Prior Publication Data
US 2019/0237669 A1  Aug. 1, 2019

(30) Foreign Application Priority Data
Feb. 28, 2017 (KR) .................. 10-2017-0026712

(51) Int. Cl.
*H01L 51/00* (2006.01)
*H01L 51/50* (2006.01)
(Continued)

(52) U.S. Cl.
CPC .......... *H01L 51/006* (2013.01); *C07C 211/61* (2013.01); *C07C 217/76* (2013.01);
(Continued)

(58) Field of Classification Search
CPC .......... C09D 7/63; C09D 4/00; C07C 211/61; C07C 217/76; H01L 51/006; H01L 51/56; H01L 51/5056
See application file for complete search history.

(56) References Cited

U.S. PATENT DOCUMENTS

2004/0062949 A1  4/2004  Pfeiffer et al.
2005/0240011 A1  10/2005  Wallace et al.
(Continued)

FOREIGN PATENT DOCUMENTS

CN  105733562 A  7/2016
EP  2610240 A1  7/2013
(Continued)

OTHER PUBLICATIONS

STN Search (Mar. 30, 2021).*
(Continued)

*Primary Examiner* — Vu A Nguyen
(74) *Attorney, Agent, or Firm* — Lerner, David, Littenberg, Krumholz & Mentlik, LLP

(57) ABSTRACT

The present specification relates to a fluorene-based compound of Formula 1, a coating composition comprising the fluorene-based compound of Formula 1, an organic light emitting device using the same, and a manufacturing method thereof.

19 Claims, 5 Drawing Sheets

(51) Int. Cl.
*H01L 51/56* (2006.01)
*C07C 211/61* (2006.01)
*C07C 217/76* (2006.01)
*C09K 11/06* (2006.01)
*C09D 7/63* (2018.01)
*C09D 4/00* (2006.01)
*C09D 7/40* (2018.01)

(52) U.S. Cl.
CPC .................. *C09D 4/00* (2013.01); *C09D 7/40* (2018.01); *C09D 7/63* (2018.01); *C09K 11/06* (2013.01); *C09K 2211/1007* (2013.01); *C09K 2211/1011* (2013.01); *H01L 51/0035* (2013.01); *H01L 51/0039* (2013.01); *H01L 51/0058* (2013.01); *H01L 51/5056* (2013.01); *H01L 51/5088* (2013.01); *H01L 51/56* (2013.01)

(56) References Cited

U.S. PATENT DOCUMENTS

| | | |
|---|---|---|
| 2012/0326137 A1 | 12/2012 | Song et al. |
| 2015/0094437 A1 | 4/2015 | Caille et al. |
| 2015/0115239 A1 | 4/2015 | Pflumm et al. |
| 2019/0225581 A1 | 7/2019 | Scheible |
| 2019/0237669 A1 | 8/2019 | Kang et al. |

FOREIGN PATENT DOCUMENTS

| | | |
|---|---|---|
| JP | 2004514257 A | 5/2004 |
| JP | 2006504764 A | 2/2006 |
| JP | 2015511215 A | 4/2015 |
| JP | 2016160420 A | 9/2016 |
| JP | 2016194021 A | 11/2016 |
| JP | 2019531311 A | 10/2019 |
| JP | 2019532958 A | 11/2019 |
| KR | 20030072355 A | 9/2003 |
| KR | 20090114716 A | 11/2009 |
| KR | 20090117078 A | 11/2009 |
| KR | 20120112277 A | 10/2012 |
| KR | 20130028813 A | 3/2013 |
| KR | 20140107594 A | 9/2014 |
| KR | 20140132562 A | 11/2014 |
| KR | 20140146103 A | 12/2014 |
| KR | 20150034379 A | 4/2015 |
| KR | 20150093995 A | 8/2015 |
| KR | 20150093995 A * | 8/2015 |
| KR | 20160041124 A | 4/2016 |
| KR | 20160067728 A | 6/2016 |
| WO | 0241414 A1 | 5/2002 |

OTHER PUBLICATIONS

International Search Report for PCT/KR2017/014484, dated Mar. 26, 2018.
Extended European Search Report including the Search Opinion for Application No. 17899165.9 dated Oct. 9, 2019, 9 pages.
Extended European Search Report including the Search Opinion for Application No. 18760593.6 dated Oct. 9, 2019, 9 pages.
International Search Report for PCT/KR2018/000347 dated Apr. 13, 2018.

* cited by examiner

[Figure 1]
[Figure 2]
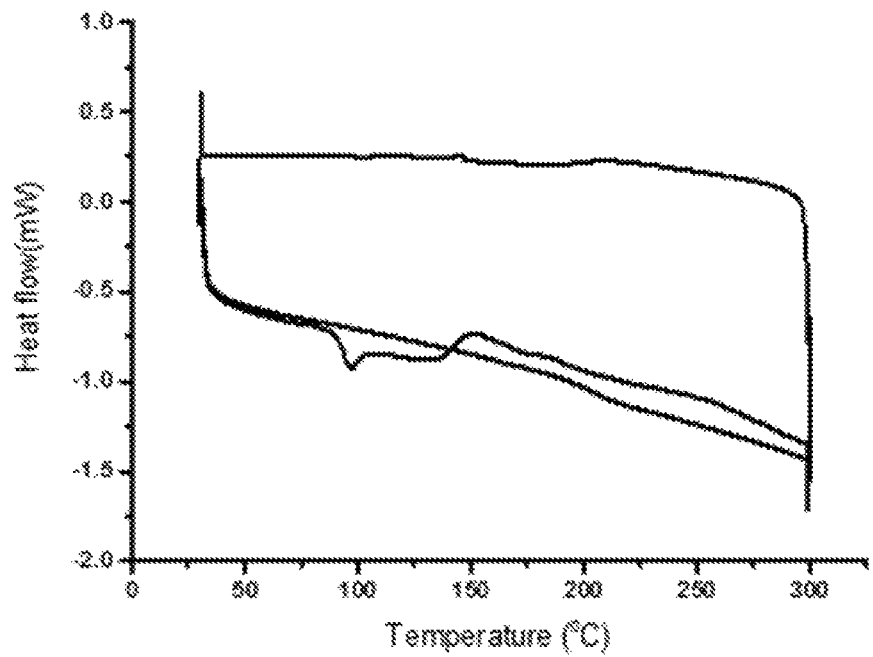

[Figure 3]
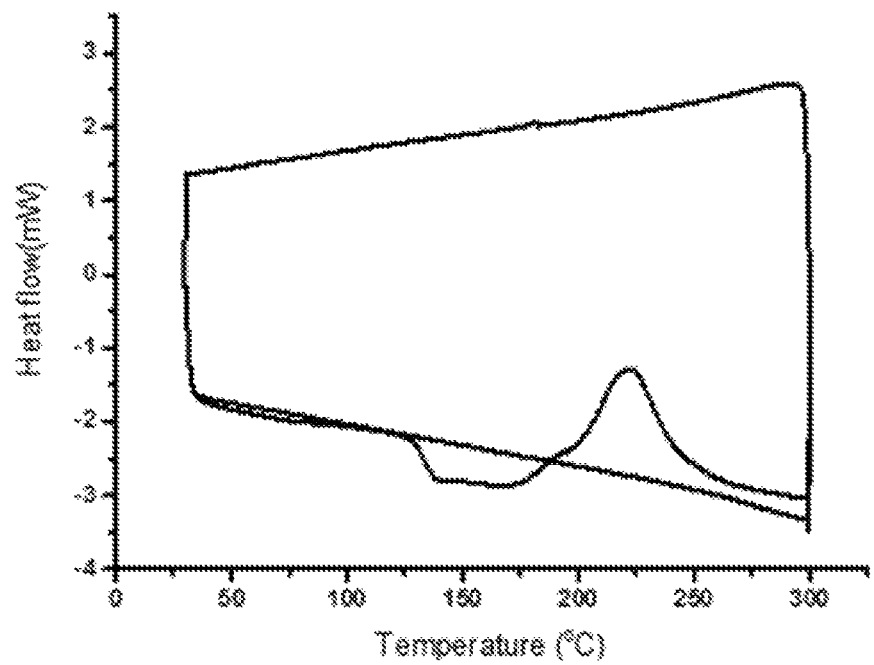
[Figure 4]
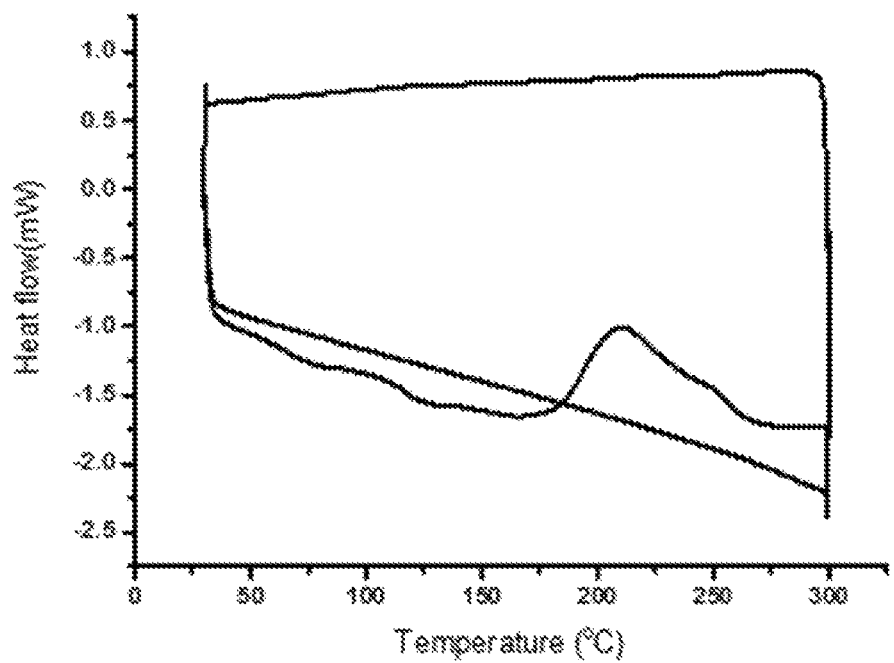

[Figure 5]
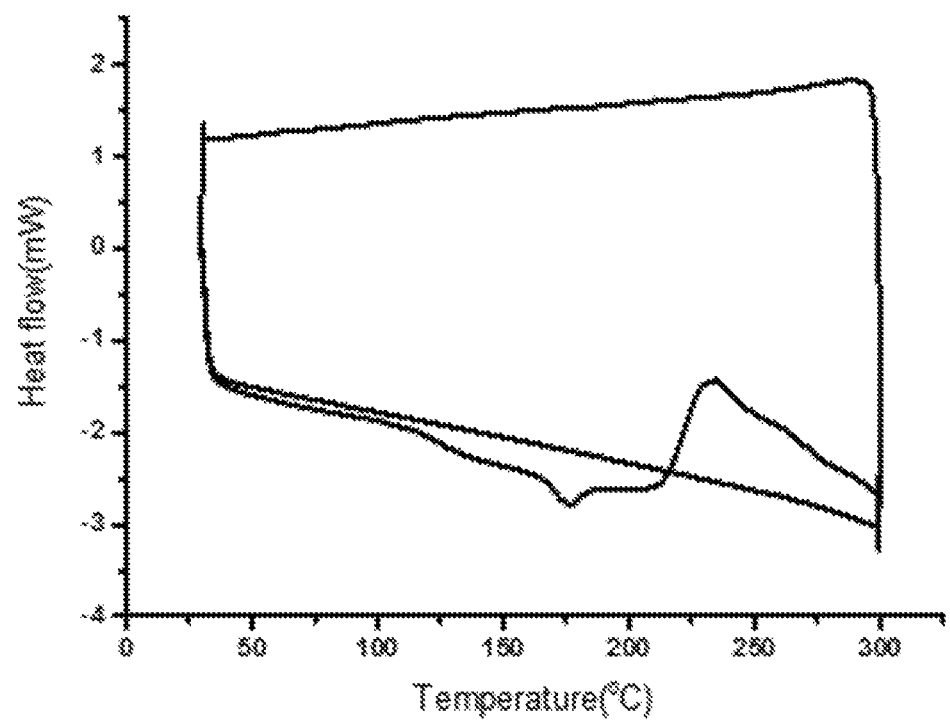

[Figure 6]
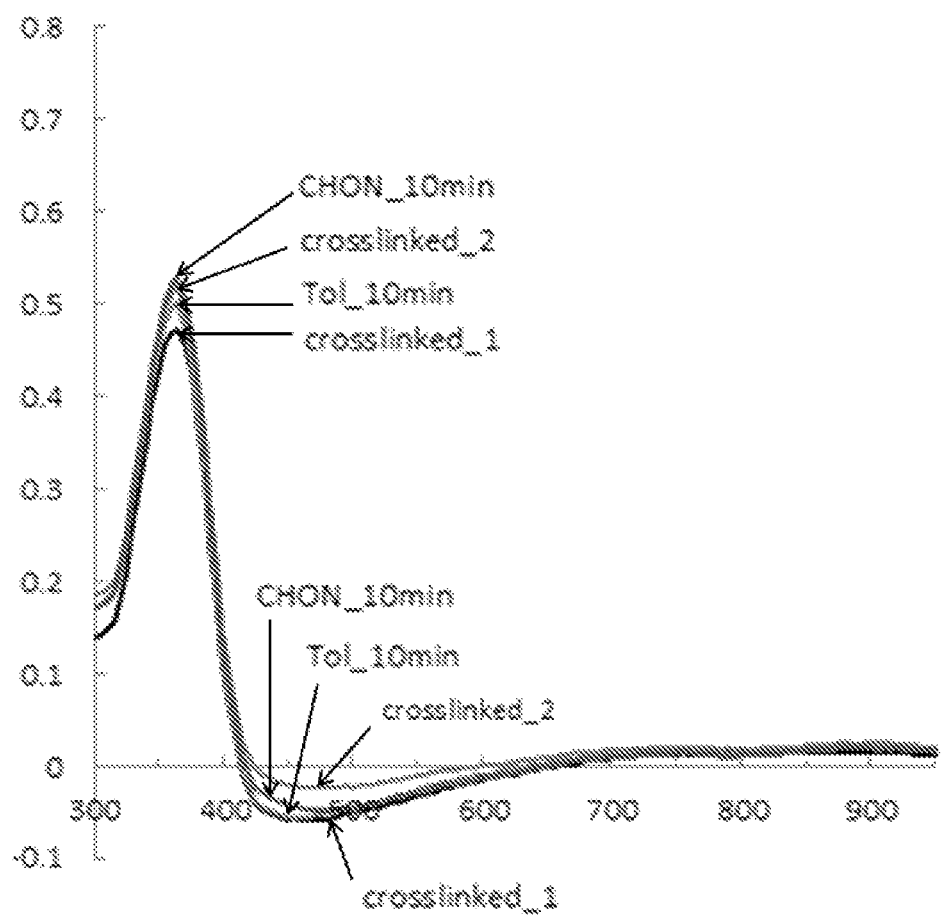

[Figure 7]
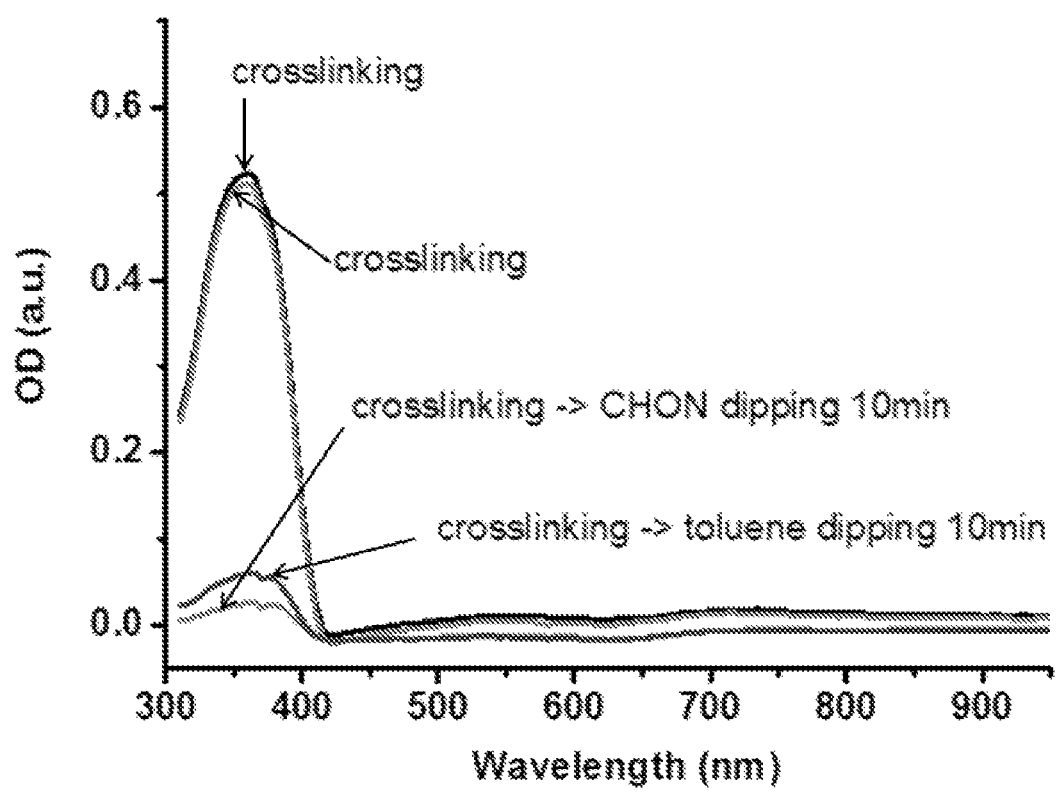

FLUORENE-BASED COMPOUND, ORGANIC LIGHT-EMITTING DEVICE USING SAME AND METHOD FOR PREPARING SAME

CROSS-REFERENCE TO RELATED APPLICATIONS

The present application is a national phase entry under 35 U.S.C. § 371 of International Application No. PCT/KR2018/000347 filed Jan. 8, 2018, which claims priority from Korean Patent Application No. 10-2017-0026712 filed Feb. 28, 2017, all of which are incorporated herein by reference.

TECHNICAL FIELD

The present specification relates to a fluorene-based compound, a coating composition comprising the fluorene-based compound, an organic light emitting device formed by using the coating composition, and a manufacturing method thereof.

BACKGROUND ART

An organic light emission phenomenon is one of the examples of converting an electric current into visible rays through an internal process of a specific organic molecule. The principle of the organic light emission phenomenon is as follows. When an organic material layer is disposed between an anode and a cathode, if an electric current is applied between the two electrodes, electrons and holes are injected into the organic material layer from the cathode and the anode, respectively. The electrons and the holes which are injected into the organic material layer are recombined to form an exciton, and the exciton falls down again to the ground state to emit light. An organic light emitting device using this principle may be generally composed of a cathode, an anode, and an organic material layer disposed therebetween, for example, an organic material layer comprising a hole injection layer, a hole transport layer, a light emitting layer, and an electron transport layer.

The materials used in the organic light emitting device are mostly pure organic materials or complex compounds in which organic materials and metals form a complex, and may be classified into a hole injection material, a hole transport material, a light emitting material, an electron transport material, an electron injection material, and the like according to the use thereof. Here, an organic material having a p-type property, that is, an organic material, which is easily oxidized and electrochemically stable when the material is oxidized, is usually used as the hole injection material or the hole transport material. Meanwhile, an organic material having an n-type property, that is, an organic material, which is easily reduced and electrochemically stable when the material is reduced, is usually used as the electron injection material or the electron transport material. As the light emitting layer material, a material having both p-type and n-type properties, that is, a material, which is stable in both the oxidation and reduction states, is preferred, and when an exciton is formed, a material having high light emitting efficiency for converting the exciton into light is preferred.

In order to obtain a high efficiency organic light emitting device which is capable of being driven at low voltage, holes or electrons injected into the organic light emitting device need to be smoothly transferred to a light emitting layer, and simultaneously, the injected holes and electrons need not go out of the light emitting layer. For this purpose, the materials used in the organic light emitting device need to have an appropriate band gap and HOMO or LUMO energy levels.

In addition, the materials used in the organic light emitting device need to have excellent chemical stability, excellent charge mobility, excellent interface characteristics with electrodes or adjacent layers, and the like. That is, the materials used in the organic light emitting device need to be minimally deformed by moisture or oxygen. Further, by having appropriate hole or electron mobility to make a balance between densities of holes and electrons in a light emitting layer of the organic light emitting device, the materials used in the organic light emitting device need to enable excitons to be maximally formed. Moreover, the materials used in the organic light emitting device need to enable the interface with an electrode comprising a metal or a metal oxide to be improved for the stability of the device.

In addition to those mentioned above, materials used in an organic light emitting device for a solution process need to additionally have the following properties.

First, the materials used in the organic light emitting device need to form a storable homogenous solution. Since a commercialized material for a deposition process has good crystallinity so that the material is not dissolved well in a solution or the crystals thereof are easily formed even though the material forms a solution, it is highly likely that according to the storage period, the concentration gradient of the solution varies or a defective device is formed.

Second, layers in which a solution process is carried out need to have resistance to a solvent and a material, which are used during a process of forming other layers, and are required to have excellent current efficiency and excellent service life characteristics when an organic light emitting device is manufactured.

Therefore, there is a need for developing a new organic material in the art.

DETAILED DESCRIPTION OF THE INVENTION

Technical Problem

An object of the present specification is to provide a fluorene-based compound, which can be used in an organic light emitting device for a solution process, and an organic light emitting device comprising the same.

Technical Solution

Provided is a fluorene-based compound represented by the following Formula 1.

[Formula 1]

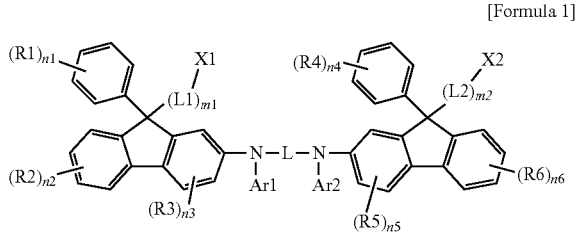

In Formula 1,

L1 and L2 are the same as or different from each other, and are each independently a substituted or unsubstituted alkylene group; a substituted or unsubstituted cycloalkylene group; or a substituted or unsubstituted heteroarylene group, L is a substituted or unsubstituted arylene group; or a substituted or unsubstituted heteroarylene group, R1 to R6 are the same as or different from each other, and are each independently hydrogen; deuterium; a halogen group; a substituted or unsubstituted alkyl group; a substituted or unsubstituted alkoxy group; a substituted or unsubstituted aryl group; or a substituted or unsubstituted heteroaryl group, or adjacent groups may combine with each other to form a substituted or unsubstituted hydrocarbon ring, Ar1 and Ar2 are the same as or different from each other, and are each independently a substituted or unsubstituted aryl group; or a substituted or unsubstituted heteroaryl group, X1 and X2 are the same as or different from each other, and are each independently a photocurable group or a thermosetting group, n1 and n4 are each independently an integer of 0 to 5,
n2 and n6 are each independently an integer of 0 to 4,
n3 and n5 are each independently an integer of 0 to 3,
when n1 to n6 are each 2 or more, the substituents in the parenthesis are the same as or different from each other,
m1 and m2 are each independently an integer of 2 to 12, and
when m1 and m2 are each 2 or more, the substituents in the parenthesis are the same as or different from each other.

The present specification provides a coating composition comprising the above-described fluorene-based compound.

The present specification also provides an organic light emitting device comprising: a first electrode; a second electrode; and an organic material layer having one or more layers provided between the first electrode and the second electrode, in which one or more layers of the organic material layer comprise the coating composition or a cured product thereof, and the cured product of the coating composition is in a state where the coating composition is cured by a heat treatment or a light treatment.

Finally, the present specification provides a method for manufacturing an organic light emitting device, the method comprising: preparing a substrate; forming a first electrode on the substrate; forming an organic material layer having one or more layers on the first electrode; and forming a second electrode on the organic material layer, in which the forming of the organic material layer comprises forming the organic material layer having one or more layers by using the coating composition.

Advantageous Effects

A fluorene-based compound according to an exemplary embodiment of the present specification forms a stable thin film, which is not damaged in the next solution process, by a heat treatment at less than 220° C. or a UV treatment alone. A fluorene structure, an aryl group directly attached to the number 9 carbon of fluorene, and an appropriate spacer between a curing group and the fluorene may adjust a glass transition temperature and a melting point by interrupting an intermolecular interaction. Further, the mobility of a curing group is increased or the steric hindrance around the curing group is decreased, thereby allowing the fluorene-based compound according to an exemplary embodiment of the present specification to have a low curing point. The fluorene-based compound according to an exemplary embodiment of the present specification may be used as a material for an organic material layer of an organic light emitting device for a solution process, and may provide low driving voltage, high light emitting efficiency, and high service life characteristics. Further, as the fluorene-based compound is used, the solubility is increased, so that there are advantages in that when an ink of a solution process is prepared, the selection of the solvent is widened, and the melting point and the curing temperature can be lowered.

BRIEF DESCRIPTION OF DRAWINGS

FIG. 1 illustrates an example of an organic light emitting device according to an exemplary embodiment of the present specification.

FIG. 2 is a view illustrating a DSC measurement graph of Compound 1.

FIG. 3 is a view illustrating a DSC measurement graph of Comparative Compound A.

FIG. 4 is a view illustrating a DSC measurement graph of Comparative Compound B.

FIG. 5 is a view illustrating a DSC measurement graph of Comparative Compound C.

FIG. 6 is a view illustrating a result of a film retention rate experiment of Compound 1.

FIG. 7 is a view illustrating a result of a film retention rate experiment of Comparative Compound A.

101: Substrate
201: Anode
301: Hole injection layer
401: Hole transport layer
501: Light emitting layer
601: Layer which simultaneously injects and transports electrons
701: Cathode

BEST MODE

In general, since an arylamine-based single molecule used in an organic light emitting device for a solution process does not have resistance to a solvent in the next process, a curing group needs to be introduced into the arylamine-based single molecule which can be used in an OLED device for a solution process. As an appropriate distance is maintained between the curing group and the fluorene due to a linker in a fluorene-based compound to which an amine group is bonded according to the present invention, the steric hindrance around the curing group is reduced and the mobility of the curing group itself is increased, thereby efficiently performing a curing reaction during a light and heat treatment on a thin film and forming a thin film having excellent solvent resistance.

Further, when a styrene group or an ethenyl group as a curing group is bonded to a fluorene-based compound according to an exemplary embodiment of the present specification, the curing group is introduced into the number 9 carbon position of fluorene, at which a conjugation with the core structure of the fluorene is broken, thereby reducing interference on a thin film at a moiety at which the fluorene to which a cured body is bonded is connected to an arylamine-based single molecule core backbone, minimizing undesirable effects on a molecular orbital function of the core backbone, and manufacturing an organic light emitting device having a longer service life.

Hereinafter, the present specification will be described in detail.

When one member is disposed "on" another member in the present specification, this comprises not only a case where the one member is brought into contact with another member, but also a case where still another member is present between the two members.

When one part "comprises" one constituent element in the present specification, unless otherwise specifically described, this does not mean that another constituent element is excluded, but means that another constituent element may be further included.

In the present specification, the term "combination thereof" included in the Markush type expression means a mixture or a combination of one or more selected from the group consisting of constituent elements described in the Markush type expression, and means comprising one or more selected from the group consisting of the above-described constituent elements.

An exemplary embodiment of the present specification provides a fluorene-based compound represented by the following Formula 1. A material having a fluorene cured body represented by Formula 1 has an advantage in that a melting point and a curing temperature can be lowered by introducing a curing group having an aryl group directly attached to the number 9 carbon of fluorene and an appropriate spacer. Further, the combination of 9H of fluorene may interrupt an aggregation phenomenon during the manufacture of a device.

[Formula 1]

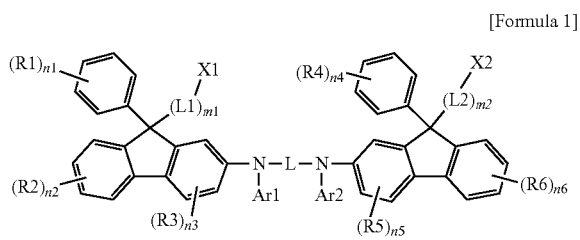

In Formula 1,

L1 and L2 are the same as or different from each other, and are each independently a substituted or unsubstituted alkylene group; a substituted or unsubstituted cycloalkylene group; or a substituted or unsubstituted heteroarylene group, L is a substituted or unsubstituted arylene group; or a substituted or unsubstituted heteroarylene group, R1 to R6 are the same as or different from each other, and are each independently hydrogen; deuterium; a halogen group; a substituted or unsubstituted alkyl group; a substituted or unsubstituted alkoxy group; a substituted or unsubstituted aryl group; or a substituted or unsubstituted heteroaryl group, or adjacent groups may combine with each other to form a substituted or unsubstituted hydrocarbon ring, Ar1 and Ar2 are the same as or different from each other, and are each independently a substituted or unsubstituted aryl group; or a substituted or unsubstituted heteroaryl group, X1 and X2 are the same as or different from each other, and are each independently a photocurable group or a thermosetting group, n1 and n4 are each independently an integer of 0 to 5,
n2 and n6 are each independently an integer of 0 to 4,
n3 and n5 are each independently an integer of 0 to 3,
when n1 to n6 are each 2 or more, the substituents in the parenthesis are the same as or different from each other,
m1 and m2 are each independently an integer of 2 to 12, and when m1 and m2 are each 2 or more, the substituents in the parenthesis are the same as or different from each other.

In an exemplary embodiment of the present specification, the fluorene-based compound of Formula 1 is preferably compounds having solubility to a suitable organic solvent.

In the present specification, the "a thermosetting group or a photocurable group" may mean a reactive substituent which cross-links compounds by being exposed to heat and/or light. The cross-linkage may be produced while radicals produced by decomposing carbon-carbon multiple bonds and cyclic structures by means of a heat treatment or light irradiation are linked to each other.

In an exemplary embodiment of the present specification, the thermosetting group or the photocurable group is any one of the following structures.

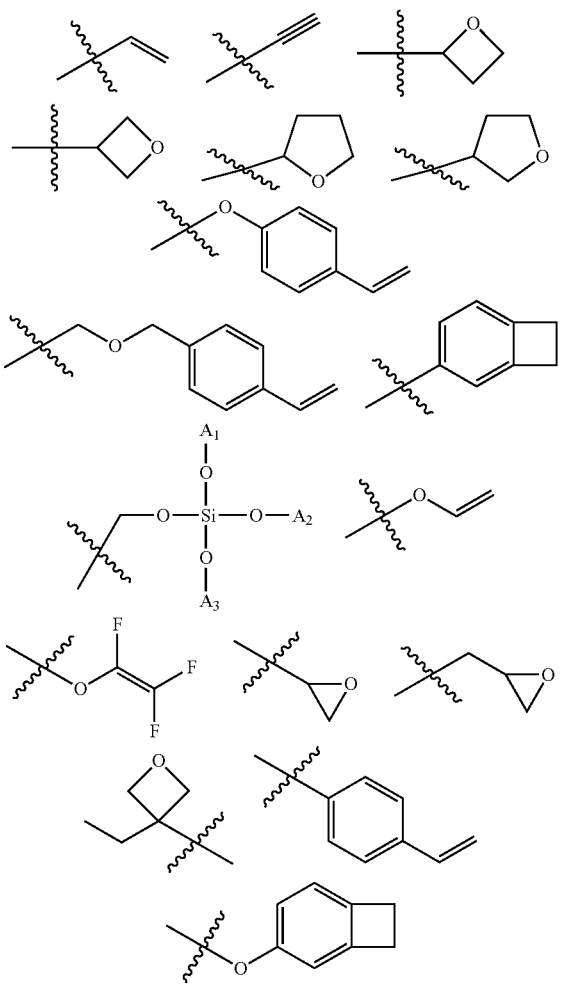

In the structures,

A1 to A3 are the same as or different from each other, and are each independently a substituted or unsubstituted alkyl group having 1 to 6 carbon atoms.

In an exemplary embodiment of the present specification, a fluorene-based compound comprising a thermosetting group or a photocurable group has an economic effect in terms of time and cost because an organic light emitting device can be manufactured by a solution application method.

Further, when a coating layer is formed by using a coating composition comprising a fluorene-based compound comprising a thermosetting group or a photocurable group, the thermosetting group or the photocurable group forms a cross-linkage by heat or light, and as a result, when an additional layer is stacked on an upper portion of the coating layer, the compound included in the coating composition is prevented from being washed away by a solvent, thereby retaining the coating layer and simultaneously stacking the additional layer on the upper portion.

Additionally, when the thermosetting group or the photocurable group forms a cross-linkage, so that a coating layer is formed, there is an effect in that chemical resistance of the coating layer to the solvent is enhanced, and the film retention rate is high.

Further, in the case of a fluorene-based compound according to an exemplary embodiment of the present specification, an organic light emitting device may be manufactured by a solution application method, thereby enabling a large area of the device to be implemented.

A fluorene-based compound in which a cross-linkage is formed by a heat treatment or light irradiation according to an exemplary embodiment of the present specification has an effect in that the thermal stability is excellent because a plurality of fluorene-based compounds is cross-linked, and thus the cross-linkage is provided in the form of a thin film in the organic light emitting device.

In addition, the fluorene-based compound according to an exemplary embodiment of the present specification comprises an amine structure in the core structure and thus may have appropriate energy level and bandgap as hole injection, a hole transport material or a light emitting material in the organic light emitting device. Furthermore, it is possible to finely adjust appropriate energy level and bandgap by adjusting a substituent of a fluorene-based compound of Formula 1 according to an exemplary embodiment of the present specification, and to provide an organic light emitting device having low driving voltage and high light emitting efficiency by improving interfacial characteristics between the organic materials. Hereinafter, the substituent of the present specification will be described in detail.

A position where a substituent is not bonded to the compound described in the present specification may be hydrogen, or deuterium may be bonded to the position.

In the present specification,

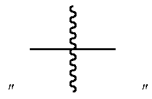

and "- - - - - -" If mean a moiety bonded to another substituent or a bonding portion.

In the present specification, the term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being unsubstituted or substituted with one or more substituents selected from the group consisting of hydrogen; deuterium; a halogen group; a nitrile group; a nitro group; a hydroxyl group; a silyl group; an alkyl group; a cycloalkyl group; an alkoxy group; an alkenyl group; an aryl group; and a heteroaryl group, or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

In the present specification, the halogen group is fluorine; chlorine; bromine; or iodine.

In the present specification, the alkyl group may be straight-chained, branched or cyclic, and the number of carbon atoms thereof is not particularly limited, but is preferably 1 to 40. According to an exemplary embodiment, the number of carbon atoms of the alkyl group is 1 to 20. Specific examples thereof comprise a methyl group, an ethyl group, a propyl group, an n-propyl group, an isopropyl group, a butyl group, an n-butyl group, an isobutyl group, a tert-butyl group, a sec-butyl group, a pentyl group, an n-pentyl group, an isopentyl group, a tert-pentyl group, a hexyl group, an n-hexyl group, heptyl, an n-heptyl group, a hexyl group, an n-hexyl group, and the like, but are not limited thereto.

In the present specification, the alkoxy group may be straight-chained, branched, or cyclic.

The number of carbon atoms of the alkoxy group is not particularly limited, but is preferably 1 to 20. Specific examples thereof comprise a methoxy group, an ethoxy group, an n-propoxy group, an isopropoxy group, an i-propyloxy group, an n-butoxy group, an isobutoxy group, a tert-butoxy group, a sec-butoxy group, an n-pentyloxy group, an neopentyloxy group, an isopentyloxy group, an n-hexyloxy group, a 3,3-dimethylbutyloxy group, a 2-ethylbutyloxy group, an n-octyloxy group, an n-nonyloxy group, an n-decyloxy group, a benzyloxy group, a p-methylbenzyloxy group, and the like, but are not limited thereto.

In the present specification, the alkenyl group may be straight-chained or branched, and the number of carbon atoms thereof is not particularly limited, but is preferably 2 to 40. Specific examples thereof comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, and the like, but are not limited thereto.

In the present specification, a silyl group may be represented by a formula of —SiRR'R", and R, R', and R" may be each hydrogen; a substituted or unsubstituted alkyl group; or a substituted or unsubstituted aryl group. Specific examples thereof comprise a trimethylsilyl group, a triethylsilyl group, a tert-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 40. According to another exemplary embodiment, the number of carbon atoms of the cycloalkyl group is 3 to 20. Specific examples thereof comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group, and the like, but are not limited thereto.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 40. According to an exemplary embodiment, the number of carbon atoms of the aryl group is 6 to 20. Examples of the monocyclic aryl group comprise a phenyl group, a biphenyl group, a terphenyl group, and the like, but are not limited thereto. Examples of the polycyclic aryl group comprise a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the fluorenyl group may be

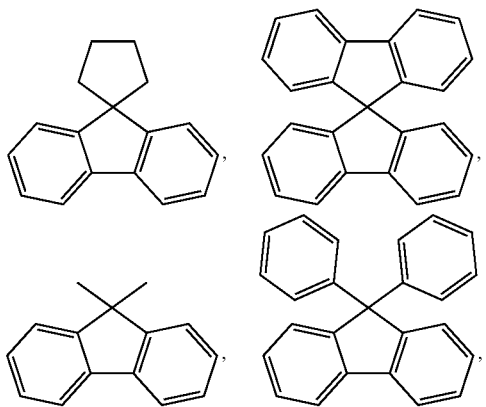

and the like. However, the fluorenyl group is not limited thereto.

In the present specification, a heteroaryl group comprises one or more atoms other than carbon, that is, one or more heteroatoms, and specifically, the heteroatom may comprise one or more atoms selected from the group consisting of O, N, Se, S, and the like. The number of carbon atoms thereof is not particularly limited, but is preferably 2 to 60. According to an exemplary embodiment, the number of carbon atoms of the heteroaryl group is 2 to 40. According to an exemplary embodiment, the number of carbon atoms of the heteroaryl group is 2 to 20. The heteroaryl group may be monocyclic or polycyclic. Examples of a heterocyclic group comprise a thiophene group, a furanyl group, a pyrrole group, an imidazolyl group, a triazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group (phenanthroline), a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the arylene group may be selected from the above-described examples of the aryl group, except for being a divalent group.

In the present specification, the alkylene group may be selected from the above-described examples of the alkyl group, except for being a divalent group.

In the present specification, the cycloalkylene group may be selected from the above-described examples of the cycloalkyl group, except for being a divalent group.

In the present specification, the heteroarylene group may be selected from the above-described examples of the heteroaryl group, except for being a divalent group.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the ring formed by combining the adjacent groups with each other may be monocyclic or polycyclic, may be an aliphatic ring, an aromatic ring, or a condensed ring of the aliphatic ring and the aromatic ring, and may form a hydrocarbon ring.

The hydrocarbon ring may be selected from the above-described examples of the cycloalkyl group or the aryl group, except for being a divalent group.

According to an exemplary embodiment of the present specification, R1 is hydrogen; deuterium; a halogen group; a substituted or unsubstituted alkyl group having 1 to 20 carbon atoms; a substituted or unsubstituted alkoxy group having 1 to 20 carbon atoms; a substituted or unsubstituted aryl group having 6 to 60 carbon atoms; or a substituted or unsubstituted heteroaryl group having 2 to 60 carbon atoms, or adjacent groups combine with each other to form a substituted or unsubstituted hydrocarbon ring.

According to another exemplary embodiment, R1 is hydrogen; deuterium; a halogen group; a substituted or unsubstituted alkyl group having 1 to 20 carbon atoms; a substituted or unsubstituted alkoxy group having 1 to 20 carbon atoms; a substituted or unsubstituted aryl group having 6 to 30 carbon atoms; or a substituted or unsubstituted heteroaryl group having 2 to 30 carbon atoms, or when n1 is 2 or more, adjacent groups combine with each other to form a substituted or unsubstituted hydrocarbon ring.

According to an exemplary embodiment of the present specification, R1 is hydrogen; deuterium; a halogen group; a substituted or unsubstituted alkyl group; or a substituted or unsubstituted aryl group, or adjacent groups combine with each other to form a hydrocarbon ring.

In an exemplary embodiment of the present specification, R1 is hydrogen; deuterium; a halogen group; a substituted or unsubstituted alkyl group having 1 to 20 carbon atoms; or a substituted or unsubstituted aryl group having 6 to 30 carbon atoms, or when n1 is 2 or more, adjacent groups combine with each other to form a hydrocarbon ring.

In another exemplary embodiment, R1 is hydrogen; deuterium; a halogen group; a substituted or unsubstituted methyl group; a substituted or unsubstituted ethyl group; a substituted or unsubstituted propyl group; a substituted or unsubstituted butyl group; a substituted or unsubstituted t-butyl group; a substituted or unsubstituted phenyl group; a substituted or unsubstituted biphenyl group; or a substituted or unsubstituted naphthyl group, or when n1 is 2 or more, adjacent groups combine with each other to form a hydrocarbon ring.

In still another exemplary embodiment, R1 is hydrogen; deuterium; a halogen group; a methyl group; an ethyl group; a propyl group; a butyl group; a t-butyl group; a phenyl group; a biphenyl group; or a naphthyl group, or when n1 is 2 or more, adjacent groups combine with each other to form a hydrocarbon ring.

In yet another exemplary embodiment, when n1 is 2 or more, two or more R1's may combine with each other to form an aromatic hydrocarbon ring.

In still yet another exemplary embodiment, when n1 is 2 or more, two or more R1's may combine with each other to form an aromatic hydrocarbon ring having 6 to 12 carbon atoms.

In a further exemplary embodiment, when n1 is 2 or more, two or more R1's may combine with each other to form a substituted or unsubstituted benzene ring and thus may become a substituted or unsubstituted naphthyl group.

According to another further exemplary embodiment, when n1 is 2 or more, two or more R1's may combine with each other to form a benzene ring and thus may become a naphthyl group.

According to an exemplary embodiment of the present specification, R4 is hydrogen; deuterium; a halogen group; a substituted or unsubstituted alkyl group having 1 to 20 carbon atoms; a substituted or unsubstituted alkoxy group having 1 to 20 carbon atoms; a substituted or unsubstituted aryl group having 6 to 60 carbon atoms; or a substituted or unsubstituted heteroaryl group having 2 to 60 carbon atoms, or adjacent groups combine with each other to form a substituted or unsubstituted hydrocarbon ring.

According to another exemplary embodiment, R4 is hydrogen; deuterium; a halogen group; a substituted or unsubstituted alkyl group having 1 to 20 carbon atoms; a substituted or unsubstituted alkoxy group having 1 to 20 carbon atoms; a substituted or unsubstituted aryl group having 6 to 30 carbon atoms; or a substituted or unsubstituted heteroaryl group having 2 to 30 carbon atoms, or when n4 is 2 or more, adjacent groups combine with each other to form a substituted or unsubstituted hydrocarbon ring.

According to an exemplary embodiment of the present specification, R4 is hydrogen; deuterium; a halogen group; a substituted or unsubstituted alkyl group; or a substituted or unsubstituted aryl group, or adjacent groups combine with each other to form a hydrocarbon ring.

In an exemplary embodiment of the present specification, R4 is hydrogen; deuterium; a halogen group; a substituted or unsubstituted alkyl group having 1 to 20 carbon atoms; or a substituted or unsubstituted aryl group having 6 to 30 carbon atoms, or when n4 is 2 or more, adjacent groups combine with each other to form a hydrocarbon ring.

In another exemplary embodiment, R4 is hydrogen; deuterium; a halogen group; a substituted or unsubstituted methyl group; a substituted or unsubstituted ethyl group; a substituted or unsubstituted propyl group; a substituted or unsubstituted butyl group; a substituted or unsubstituted t-butyl group; a substituted or unsubstituted phenyl group; a substituted or unsubstituted biphenyl group; or a substituted or unsubstituted naphthyl group, or when n4 is 2 or more, adjacent groups combine with each other to form a hydrocarbon ring.

In still another exemplary embodiment, R4 is hydrogen; deuterium; a halogen group; a methyl group; an ethyl group; a propyl group; a butyl group; a t-butyl group; a phenyl group; a biphenyl group; or a naphthyl group, or when n4 is 2 or more, adjacent groups combine with each other to form a hydrocarbon ring.

In yet another exemplary embodiment, when n4 is 2 or more, two or more R4's may combine with each other to form an aromatic hydrocarbon ring.

In still yet another exemplary embodiment, when n4 is 2 or more, two or more R4's may combine with each other to form an aromatic hydrocarbon ring having 6 to 12 carbon atoms.

In a further exemplary embodiment, when n4 is 2 or more, two or more R4's may combine with each other to form a substituted or unsubstituted benzene ring and thus may become a substituted or unsubstituted naphthyl group.

According to another further exemplary embodiment, when n4 is 2 or more, two or more R4's may combine with each other to form a benzene ring and thus may become a naphthyl group.

In an exemplary embodiment of the present specification, n1 and n4 are each independently an integer of 0 to 2.

In an exemplary embodiment of the present specification, R2, R3, R5, and R6 are the same as or different from each other, and are each independently hydrogen; deuterium; a halogen group; a substituted or unsubstituted alkyl group having 1 to 20 carbon atoms; a substituted or unsubstituted alkoxy group having 1 to 20 carbon atoms; a substituted or unsubstituted aryl group having 6 to 60 carbon atoms; or a substituted or unsubstituted heteroaryl group having 2 to 60 carbon atoms.

In an exemplary embodiment of the present specification, R2, R3, R5, and R6 are the same as or different from each other, and are each independently hydrogen; deuterium; a substituted or unsubstituted alkyl group having 1 to 20 carbon atoms; or a substituted or unsubstituted aryl group having 6 to 30 carbon atoms.

In an exemplary embodiment of the present specification, R2, R3, R5, and R6 are the same as or different from each other, and are each independently hydrogen; deuterium; a substituted or unsubstituted methyl group; a substituted or unsubstituted ethyl group; a substituted or unsubstituted propyl group; a substituted or unsubstituted butyl group; a substituted or unsubstituted phenyl group; a substituted or unsubstituted biphenyl group; or a substituted or unsubstituted naphthyl group.

In another exemplary embodiment, R2, R3, R5, and R6 are the same as or different from each other, and are each independently hydrogen; deuterium; a methyl group; an ethyl group; a propyl group; a butyl group; a phenyl group; a biphenyl group; or a naphthyl group.

According to still another exemplary embodiment, R2, R3, R5, and R6 are hydrogen.

According to an exemplary embodiment of the present specification, n2, n3, n5, and n6 are 0 or 1.

In an exemplary embodiment of the present specification, L1 and L2 are the same as or different from each other, and are each independently a substituted or unsubstituted alkylene group having 1 to 20 carbon atoms; a substituted or unsubstituted cycloalkylene group having 3 to 60 carbon atoms; or a substituted or unsubstituted heteroarylene group having 2 to 60 carbon atoms.

According to an exemplary embodiment of the present specification, L1 and L2 are the same as or different from each other, and each independently a substituted or unsubstituted alkylene group. When L1 and L2 are a substituted or unsubstituted alkylene group, L1 and L2 more efficiently reduce a steric hindrance around a curing group as compared to other linkers, and increase the mobility of the curing group itself to help the curing reaction, thereby manufacturing a thin film having excellent resistance to a solvent.

According to an exemplary embodiment of the present specification, L1 and L2 are the same as or different from each other, and are each independently a substituted or unsubstituted alkylene group having 1 to 20 carbon atoms.

According to another exemplary embodiment, L1 and L2 are the same as or different from each other, and are each independently an alkylene group having 1 to 12 carbon atoms.

According to still another exemplary embodiment, L1 and L2 are the same as or different from each other, and are each independently a substituted or unsubstituted methylene group; a substituted or unsubstituted ethylene group; a substituted or unsubstituted propylene group; a substituted or unsubstituted butylene group; a substituted or unsubstituted pentylene group; a substituted or unsubstituted hexylene group; a substituted or unsubstituted heptylene group; a substituted or unsubstituted phenylene group; a substituted or unsubstituted biphenylene group; or a substituted or unsubstituted triphenylene group.

In yet another exemplary embodiment, L1 and L2 are the same as or different from each other, and are each independently a methylene group; an ethylene group; a propylene group; a butylene group; a pentylene group; a hexylene group; or a heptylene group.

According to still yet another exemplary embodiment, L1 and L2 are a methylene group.

According to an exemplary embodiment of the present specification, m1 and m2 are each an integer of 2 to 12.

In an exemplary embodiment of the present specification, L is a substituted or unsubstituted arylene group; or a substituted or unsubstituted heteroarylene group.

In an exemplary embodiment of the present specification, L is a substituted or unsubstituted arylene group having 6 to 30 carbon atoms; or a substituted or unsubstituted heteroarylene group having 2 to 30 carbon atoms.

According to another exemplary embodiment, L is an arylene group having 6 to 30 carbon atoms, which is unsubstituted or substituted with one or more selected from the group consisting of an aryl group and an alkyl group; or a heteroarylene group having 2 to 30 carbon atoms, which is unsubstituted or substituted with one or more selected from the group consisting of an aryl group and an alkyl group.

According to still another exemplary embodiment, L is an arylene group having 6 to 30 carbon atoms, which is unsubstituted or substituted with one or more selected from the group consisting of an aryl group having 6 to 30 carbon atoms and an alkyl group having 1 to 20 carbon atoms; or a heteroarylene group having 2 to 30 carbon atoms, which is unsubstituted or substituted with one or more selected from the group consisting of an aryl group having 6 to 30 carbon atoms and an alkyl group having 1 to 20 carbon atoms.

In an exemplary embodiment of the present specification, L may be any one of the following structures, but is not limited thereto, and the following structures may be additionally substituted.

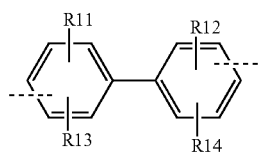

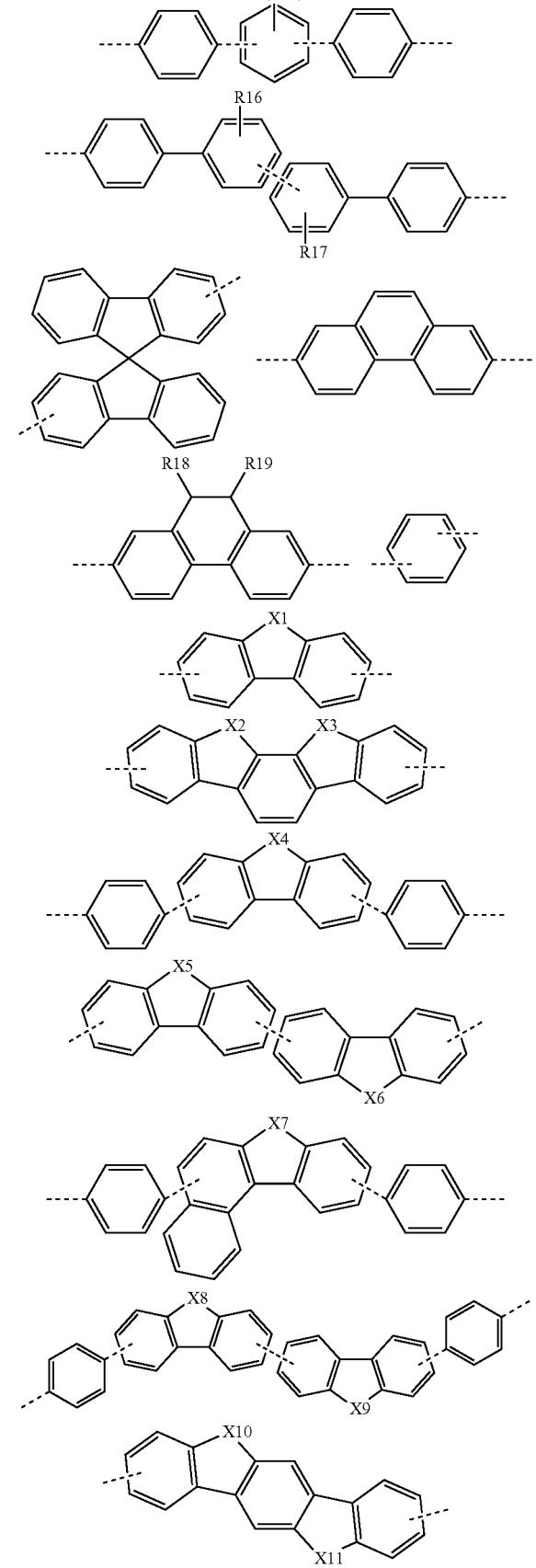

-continued

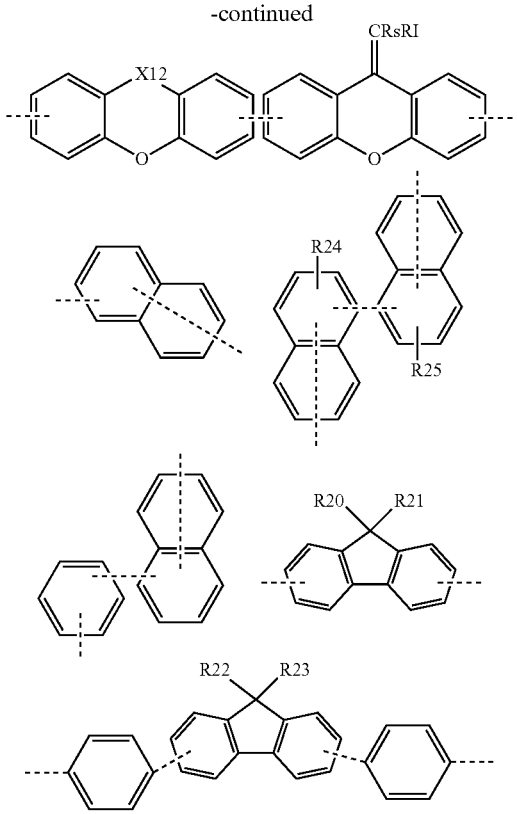

In the structures,

X12 is S, SO, CRuRv, SiRwRx or NRy,

X1 to X11 are the same as or different from each other, and are each independently O, S, SiR'R" or NR, R11 to R25, Rs, Rt, Ru, Rv, Rw, Rx, Ry, R, R', and R" are the same as or different from each other, and are each independently hydrogen; deuterium; a halogen group; a substituted or unsubstituted alkyl group; or a substituted or unsubstituted aryl group, and s1 is an integer of 0 to 4.

s1 is an integer of 0 to 2.

In an exemplary embodiment of the present specification, R11 to R25, Rs, Rt, Ru, Rv, Rw, Rx, and Ry are the same as or different from each other, and are each independently hydrogen; deuterium; a halogen group; a substituted or unsubstituted alkyl group having 1 to 30 carbon atoms; or a substituted or unsubstituted aryl group having 6 to 30 carbon atoms.

In another exemplary embodiment, R11 to R25, Rs, Rt, Ru, Rv, Rw, Rx, and Ry are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

In still another exemplary embodiment, R11 to R25, Rs, Rt, Ru, Rv, Rw, Rx, and Ry are the same as or different from each other, and are each independently hydrogen; deuterium; a halogen group; a substituted or unsubstituted alkyl group having 1 to 8 carbon atoms; or a substituted or unsubstituted aryl group having 6 to 12 carbon atoms.

According to yet another exemplary embodiment, R11 to R25, Rs, Rt, Ru, Rv, Rw, Rx, and Ry are the same as or different from each other, and are each independently hydrogen; deuterium; a substituted or unsubstituted methyl group; a substituted or unsubstituted ethyl group; a substituted or unsubstituted propyl group; a substituted or unsubstituted butyl group; a substituted or unsubstituted t-butyl group; a substituted or unsubstituted pentyl group; a substituted or unsubstituted hexyl group; a substituted or unsubstituted heptyl group; a substituted or unsubstituted octyl group; or a substituted or unsubstituted phenyl group.

According to still yet another exemplary embodiment, R11 to R25, Rs, Rt, Ru, Rv, Rw, Rx, and Ry are the same as or different from each other, and are each independently hydrogen; deuterium; a methyl group; an ethyl group; a propyl group; a butyl group; a t-butyl group; a pentyl group; a hexyl group; a heptyl group; an octyl group; or a phenyl group unsubstituted or substituted with a butyl group or a hexyl group.

In an exemplary embodiment of the present specification, R, R', and R" are the same as or different from each other, and are each independently hydrogen; deuterium; a halogen group; a substituted or unsubstituted alkyl group having 1 to 30 carbon atoms; or a substituted or unsubstituted aryl group having 6 to 30 carbon atoms.

In another exemplary embodiment, R, R', and R" are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

In still another exemplary embodiment, R, R', and R" are the same as or different from each other, and are each independently hydrogen; deuterium; a halogen group; a substituted or unsubstituted alkyl group having 1 to 8 carbon atoms; or a substituted or unsubstituted aryl group having 6 to 12 carbon atoms.

According to yet another exemplary embodiment, R, R', and R" are the same as or different from each other, and are each independently hydrogen; deuterium; a substituted or unsubstituted methyl group; a substituted or unsubstituted ethyl group; a substituted or unsubstituted propyl group; a substituted or unsubstituted butyl group; a substituted or unsubstituted t-butyl group; a substituted or unsubstituted pentyl group; a substituted or unsubstituted hexyl group; or a substituted or unsubstituted phenyl group.

According to still yet another exemplary embodiment, R, R', and R" are the same as or different from each other, and are each independently hydrogen; deuterium; a methyl group; an ethyl group; a propyl group; a butyl group; a t-butyl group; a pentyl group; a hexyl group; or a phenyl group.

In an exemplary embodiment of the present specification, X12 is S or SO.

In an exemplary embodiment of the present specification, X12 is CRuRv, SiRwRx or NRy.

In an exemplary embodiment of the present specification, Ar1 and Ar2 are the same as or different from each other, and are each independently a substituted or unsubstituted aryl group having 6 to 30 carbon atoms; or a substituted or unsubstituted heteroaryl group having 2 to 30 carbon atoms.

In another exemplary embodiment, Ar1 and Ar2 are the same as or different from each other, and are each independently a substituted or unsubstituted aryl group having 6 to 20 carbon atoms; or a substituted or unsubstituted heteroaryl group having 2 to 20 carbon atoms.

In an exemplary embodiment of the present specification, Ar1 and Ar2 may be any one of the following structures, but are not limited thereto, and the following structures may be additionally substituted.

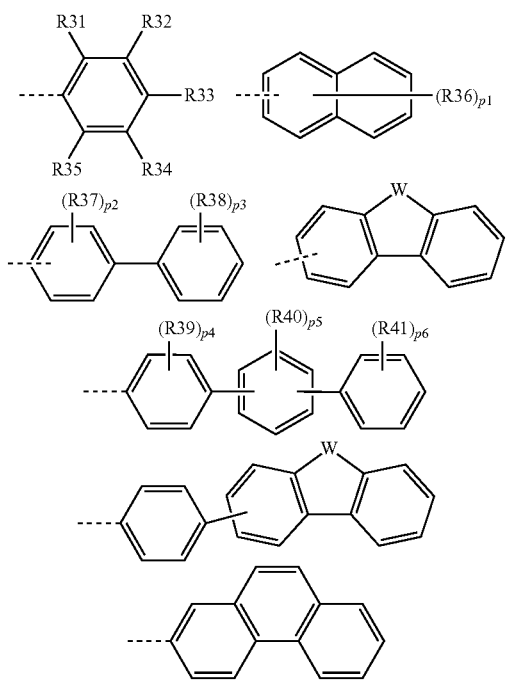

In the structures,

W is O, S, NRa, CRbRc or SiRdRe,

R31 to R41, Ra, Rb, Rc, Rd, and Re are the same as or different from each other, and are each independently hydrogen; deuterium; a halogen group; a substituted or unsubstituted alkyl group; or a substituted or unsubstituted aryl group, p1 is an integer of 0 to 7, p2, p4, and p5 are each an integer of 0 to 4, p3 and p6 are each an integer of 0 to 5, and when p1 to p6 are each 2 or more, the substituents in the parenthesis are the same as or different from each other.

In an exemplary embodiment of the present specification, R39 to R41 are the same as or different from each other, and are each independently hydrogen; deuterium; a halogen group; a substituted or unsubstituted alkyl group having 1 to 30 carbon atoms; or a substituted or unsubstituted aryl group having 6 to 30 carbon atoms.

In an exemplary embodiment of the present specification, R39 to R41 are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

In another exemplary embodiment, R39 to R41 are the same as or different from each other, and are each independently hydrogen; deuterium; a halogen group; a substituted or unsubstituted alkyl group having 1 to 8 carbon atoms; or a substituted or unsubstituted aryl group having 6 to 12 carbon atoms.

In still another exemplary embodiment, R39 to R41 are the same as or different from each other, and are each independently hydrogen.

In an exemplary embodiment of the present specification, R31 to R38 are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

In another exemplary embodiment, R31 to R38 are the same as or different from each other, and are each independently hydrogen; deuterium; a halogen group; a substituted or unsubstituted alkyl group having 1 to 8 carbon atoms; or a substituted or unsubstituted aryl group having 6 to 12 carbon atoms.

In an exemplary embodiment of the present specification, R31 to R38 are the same as or different from each other, and are each independently hydrogen; deuterium; a fluoro group; a substituted or unsubstituted methyl group; a substituted or unsubstituted ethyl group; a substituted or unsubstituted propyl group; a substituted or unsubstituted phenyl group; a substituted or unsubstituted naphthyl group; or a substituted or unsubstituted biphenyl group.

In another exemplary embodiment, R31 to R38 are the same as or different from each other, and are each independently hydrogen; deuterium; a fluoro group; a methyl group; an ethyl group; a propyl group; a phenyl group; a naphthyl group; or a biphenyl group.

In an exemplary embodiment of the present specification, W is O.

In an exemplary embodiment of the present specification, W is S.

In an exemplary embodiment of the present specification, W is CRbRc.

In an exemplary embodiment of the present specification, W is SiRdRe.

In an exemplary embodiment of the present specification, Ra, Rb, Rc, Rd, and Re are the same as or different from each other, and are each independently hydrogen; deuterium; a halogen group; a substituted or unsubstituted alkyl group having 1 to 30 carbon atoms; or a substituted or unsubstituted aryl group having 6 to 30 carbon atoms.

In an exemplary embodiment of the present specification, Ra, Rb, Rc, Rd, and Re are the same as or different from each other, and are each independently hydrogen; deuterium; a halogen group; a substituted or unsubstituted alkyl group having 1 to 20 carbon atoms; or a substituted or unsubstituted aryl group having 6 to 20 carbon atoms.

In another exemplary embodiment, Ra, Rb, Rc, Rd, and Re are the same as or different from each other, and are each independently hydrogen; deuterium; a halogen group; a substituted or unsubstituted alkyl group having 1 to 8 carbon atoms; or a substituted or unsubstituted aryl group having 6 to 12 carbon atoms.

According to still another exemplary embodiment, Ra, Rb, Rc, Rd, and Re are the same as or different from each other, and are each independently hydrogen; deuterium; a substituted or unsubstituted methyl group; a substituted or unsubstituted ethyl group; or a substituted or unsubstituted phenyl group.

According to yet another exemplary embodiment, Ra, Rb, Rc, Rd, and Re are the same as or different from each other, and are each independently hydrogen; deuterium; a methyl group; an ethyl group; or a phenyl group unsubstituted or substituted with a tert-butyl group.

According to still yet another exemplary embodiment, Ar1 and Ar2 are the same as or different from each other, and are each independently a substituted or unsubstituted phenyl group; a substituted or unsubstituted biphenyl group; a substituted or unsubstituted terphenyl group; a substituted or unsubstituted naphthyl group; a substituted or unsubstituted phenanthrenyl group; or a substituted or unsubstituted fluorenyl group.

In a further exemplary embodiment, Ar1 and Ar2 are the same as or different from each other, and are each independently a phenyl group unsubstituted or substituted with one or more selected from the group consisting of deuterium, a halogen group, and a methyl group; a biphenyl group unsubstituted or substituted with one or more selected from the group consisting of deuterium, a halogen group, and a methyl group; a terphenyl group unsubstituted or substituted with one or more selected from the group consisting of deuterium, a halogen group, and a methyl group; a napththyl group unsubstituted or substituted with one or more selected from the group consisting of deuterium, a halogen group, and a methyl group; a phenanthrenyl group unsubstituted or substituted with one or more selected from the group consisting of deuterium, a halogen group, and a methyl group; or a fluorenyl group unsubstituted or substituted with one or more selected from the group consisting of a phenyl group substituted with deuterium, a halogen group, a methyl group, and a tert-butyl group.

According to an exemplary embodiment of the present invention, the fluorene-based compound of Formula 1 may be represented by any one of the following Compounds 1 to 48.

Compound 1

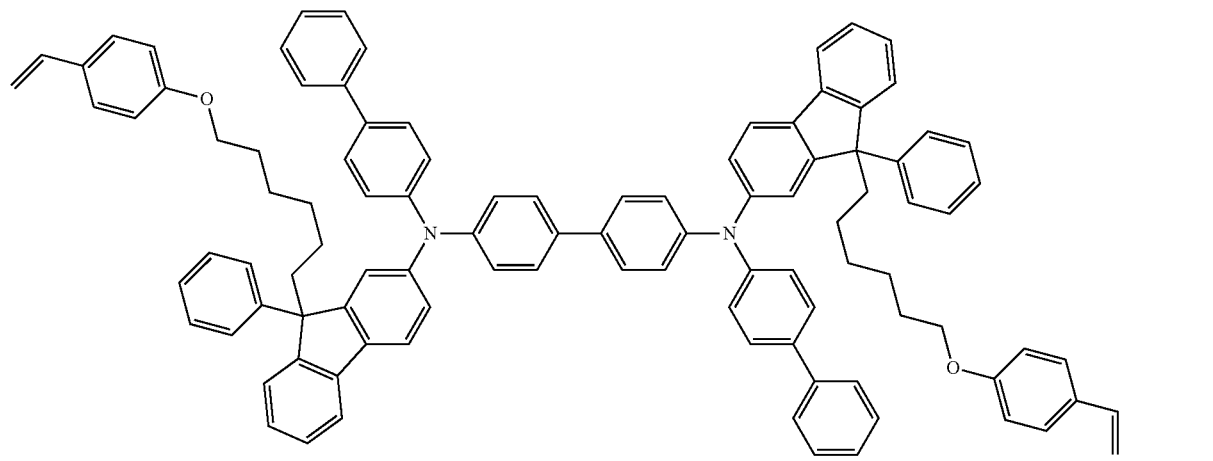

Compound 2

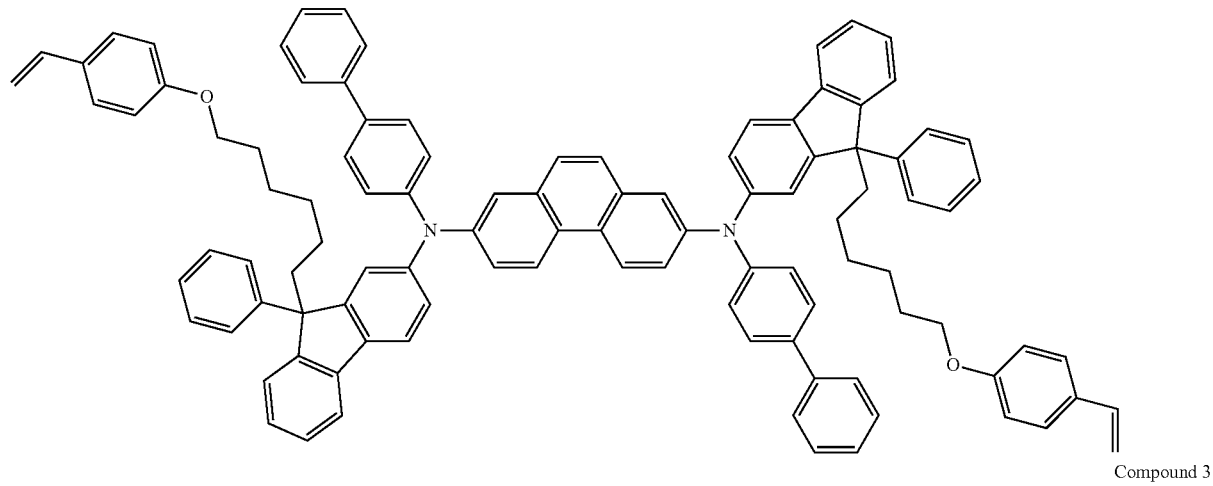

Compound 3

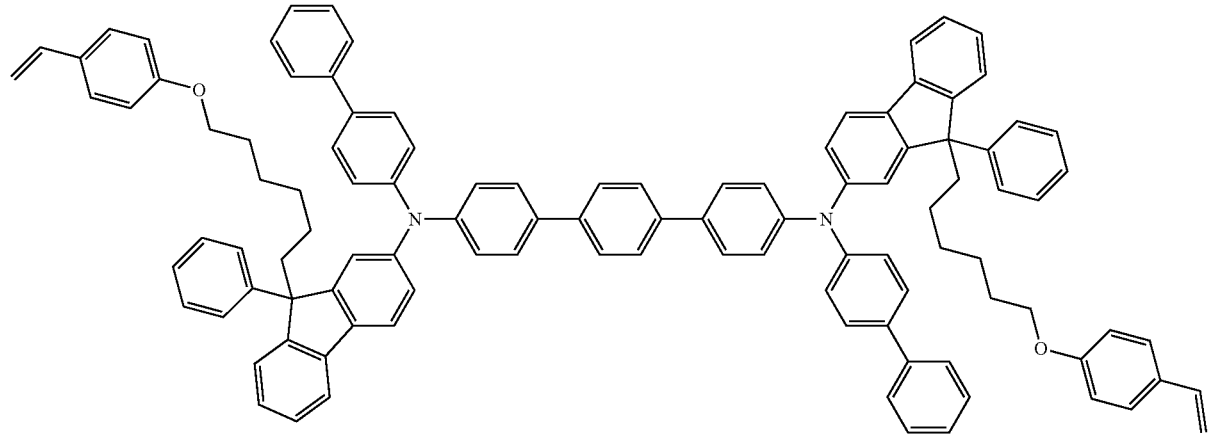

-continued
Compound 4
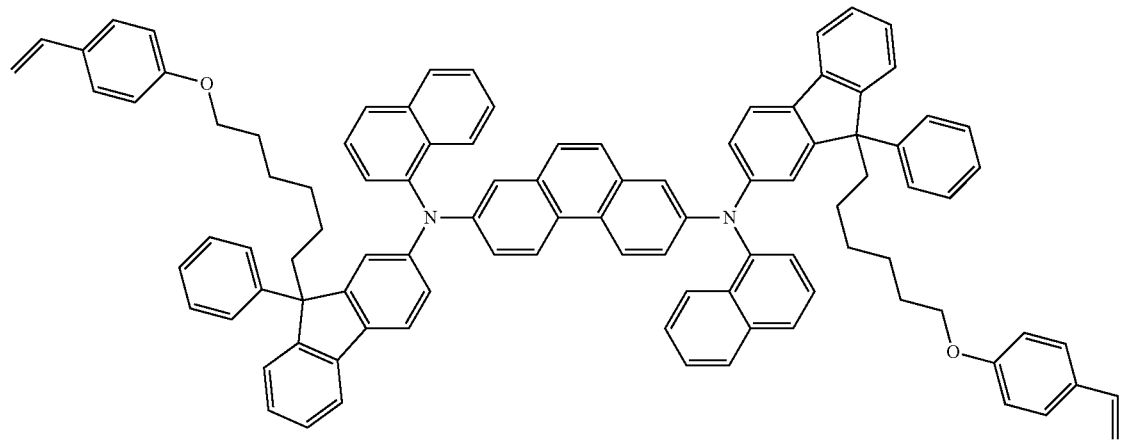
Compound 5
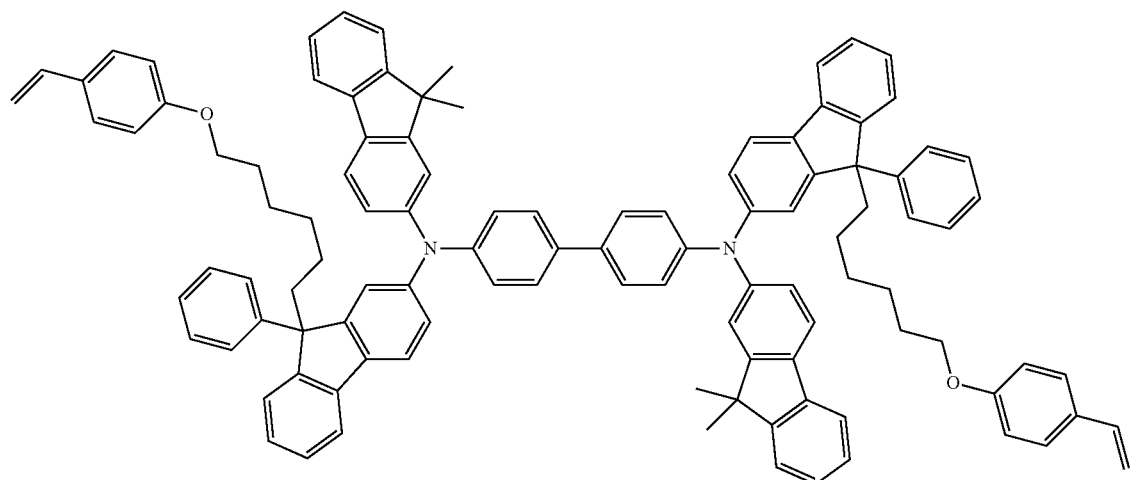
Compound 6
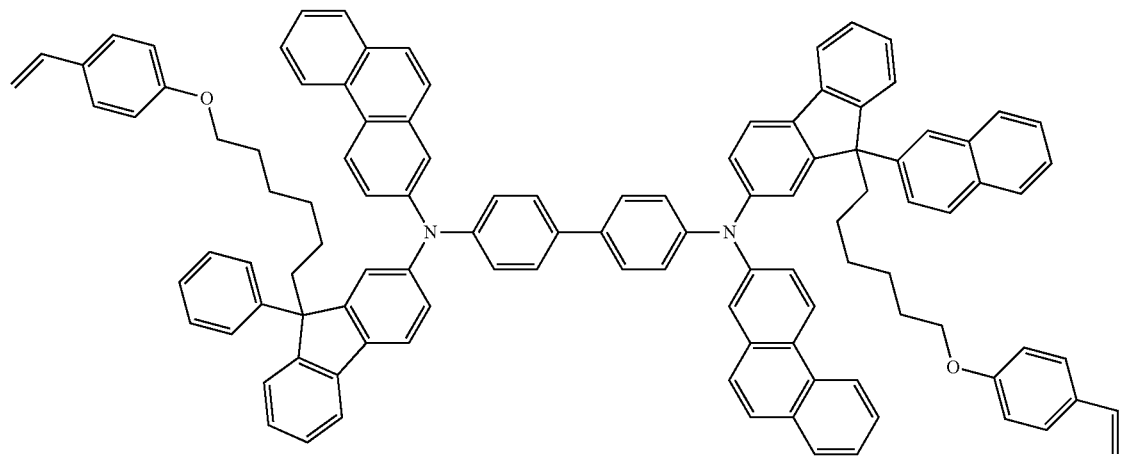

Compound 7
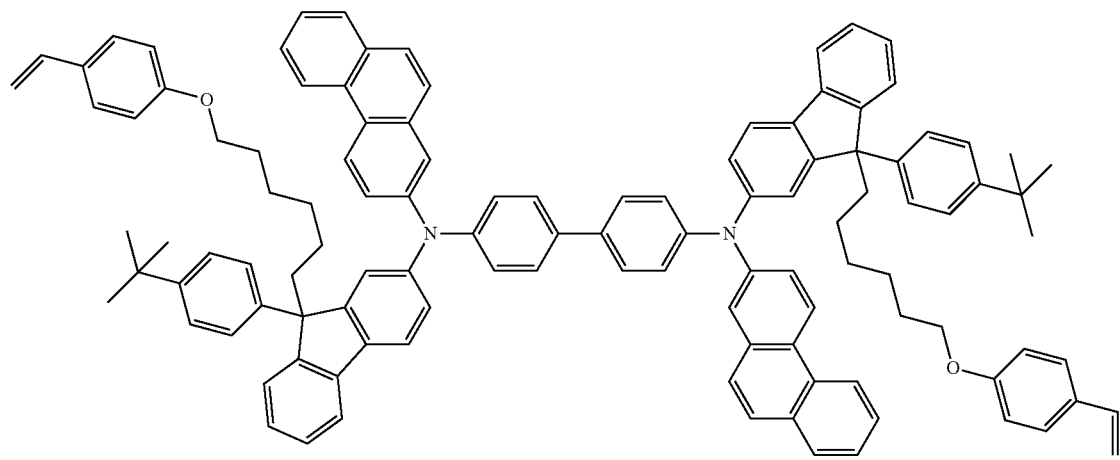
Compound 8
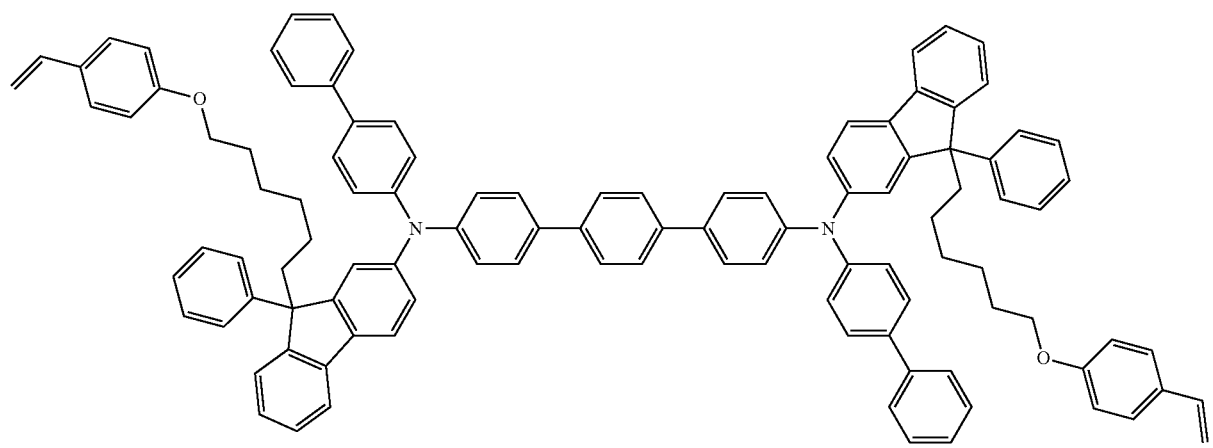
Compound 9
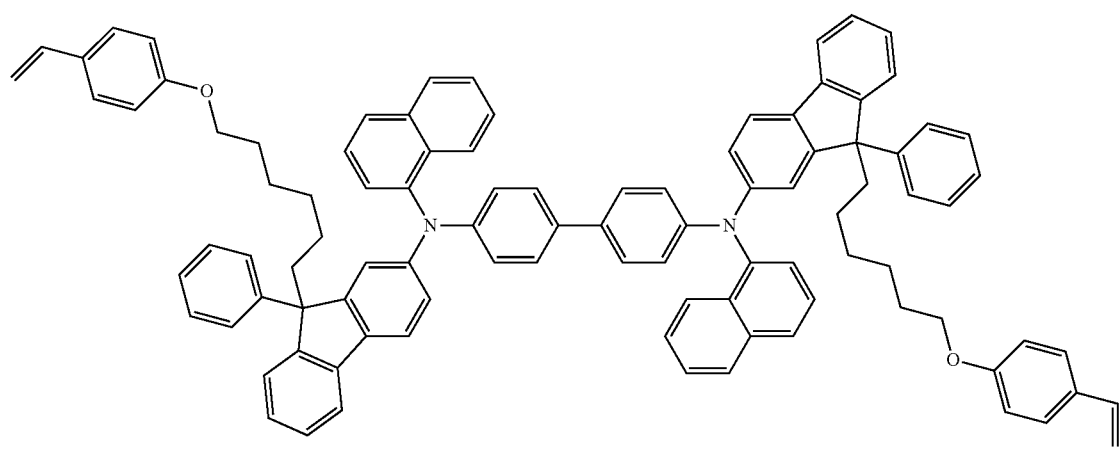

Compound 10
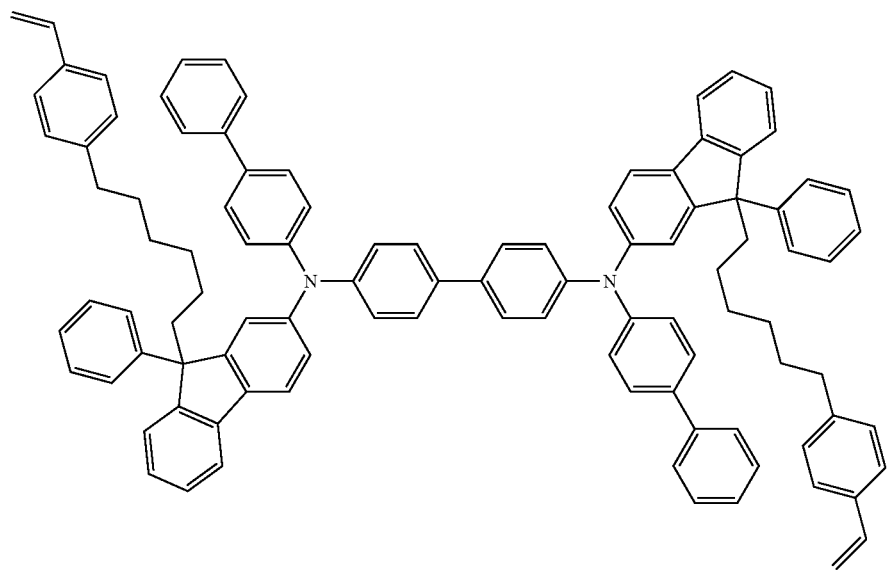
Compound 11
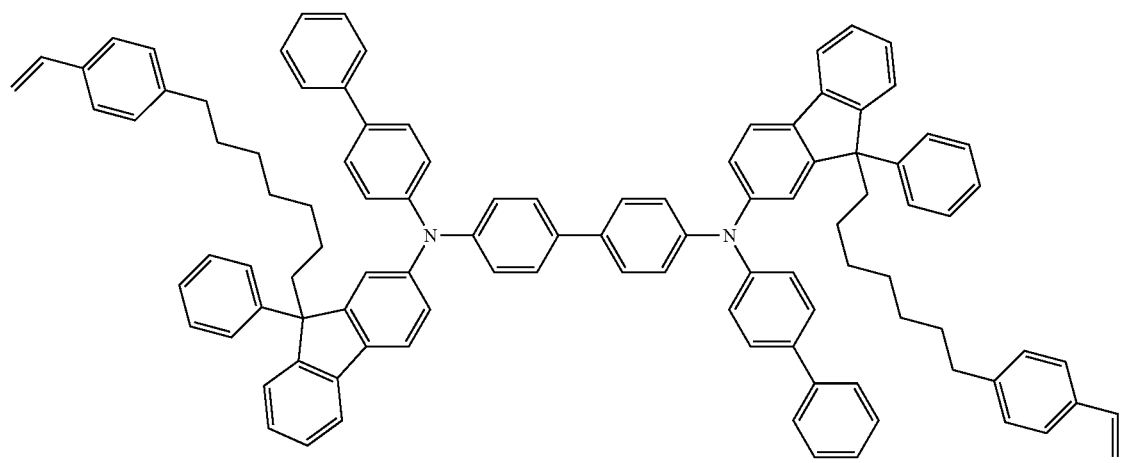
Compound 12
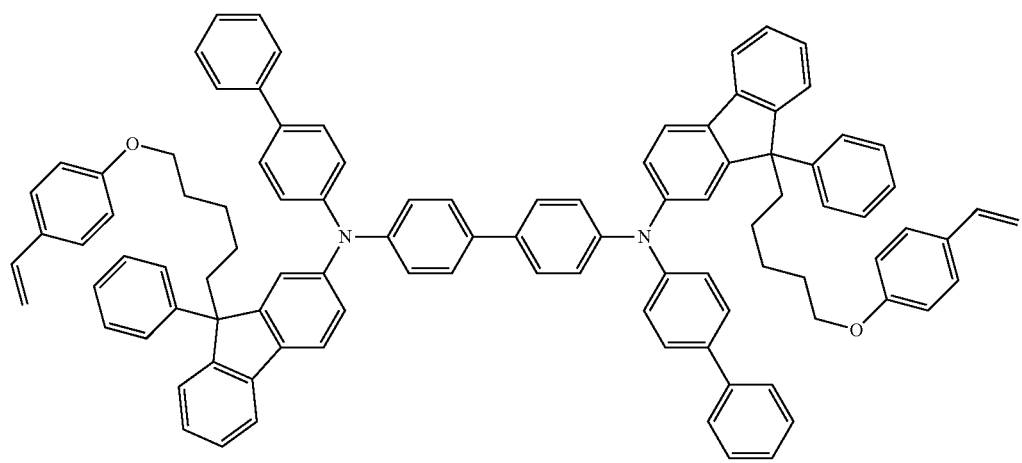

Compound 13
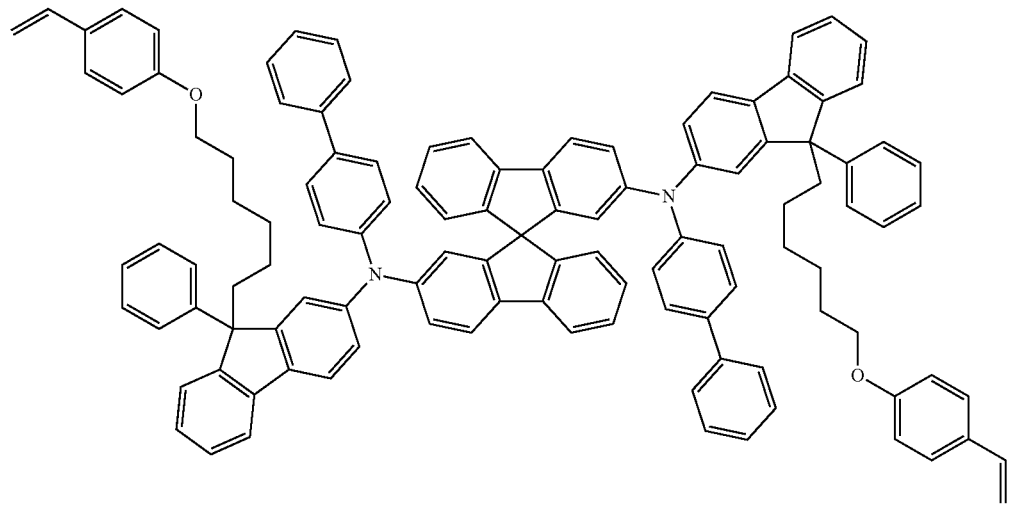
Compound 14
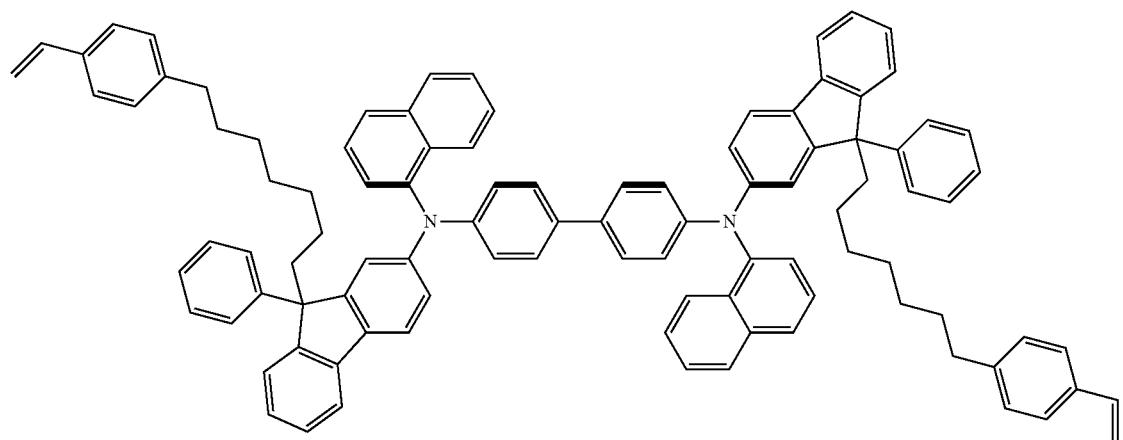
Compound 15
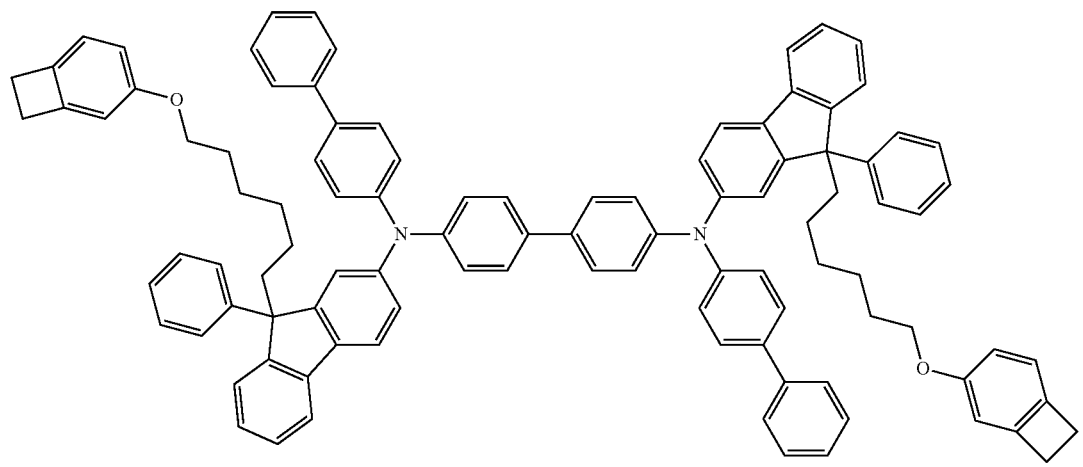

-continued
Compound 16
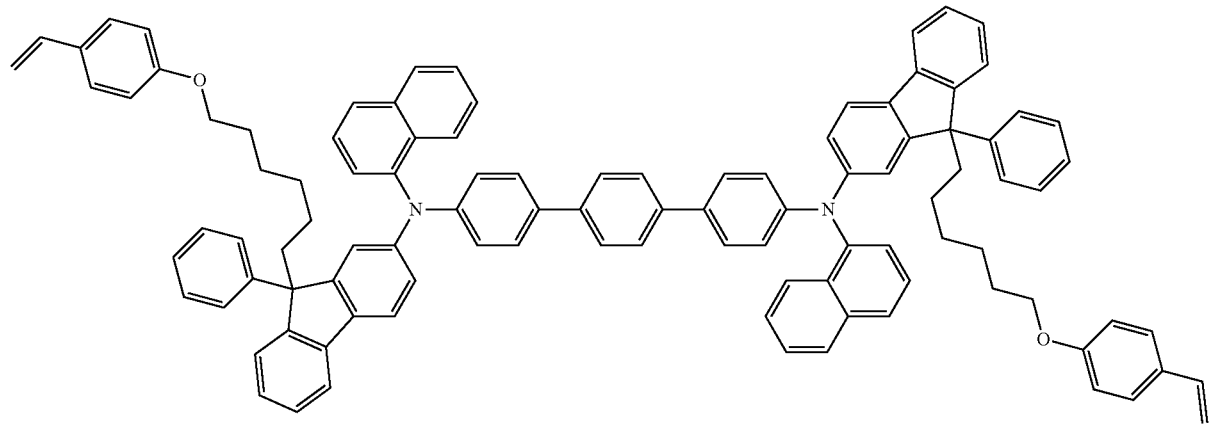
Compound 17
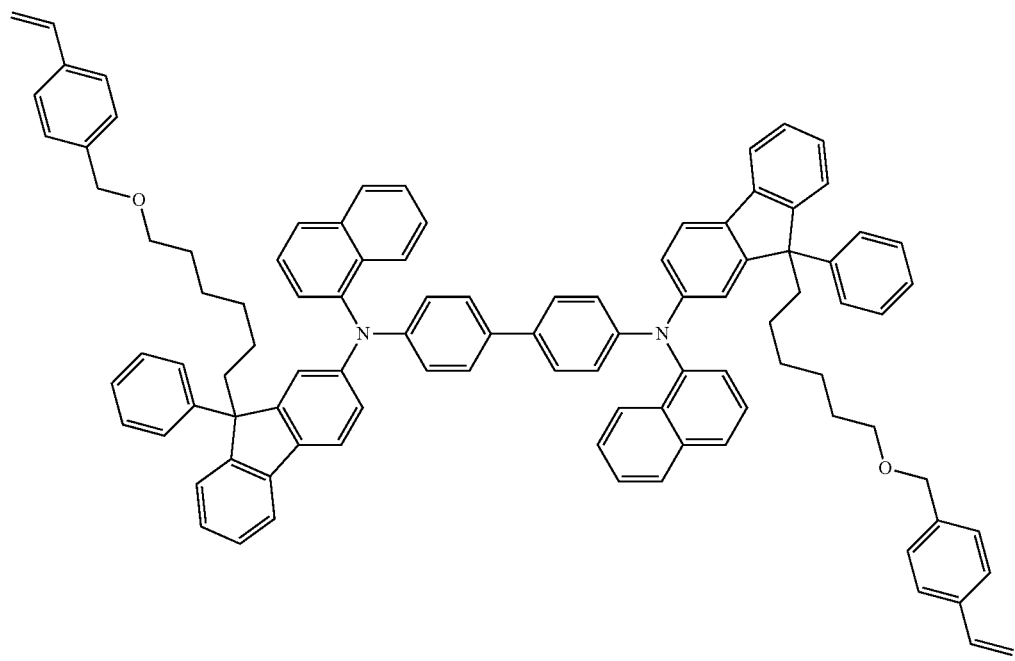
Compound 18
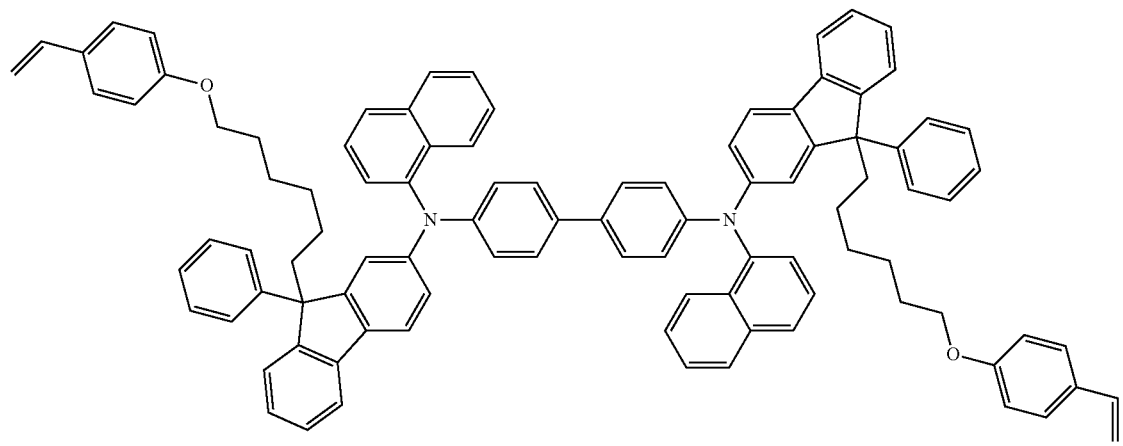

Compound 19
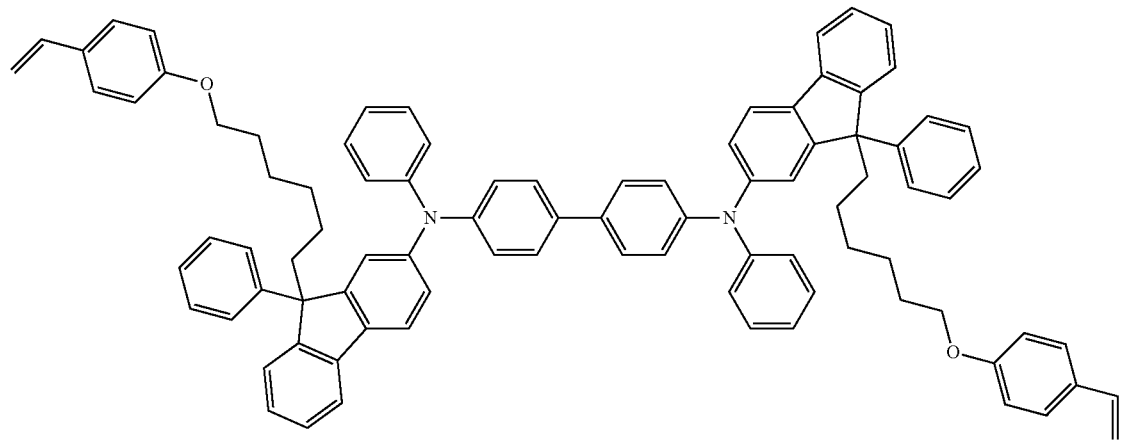
Compound 20
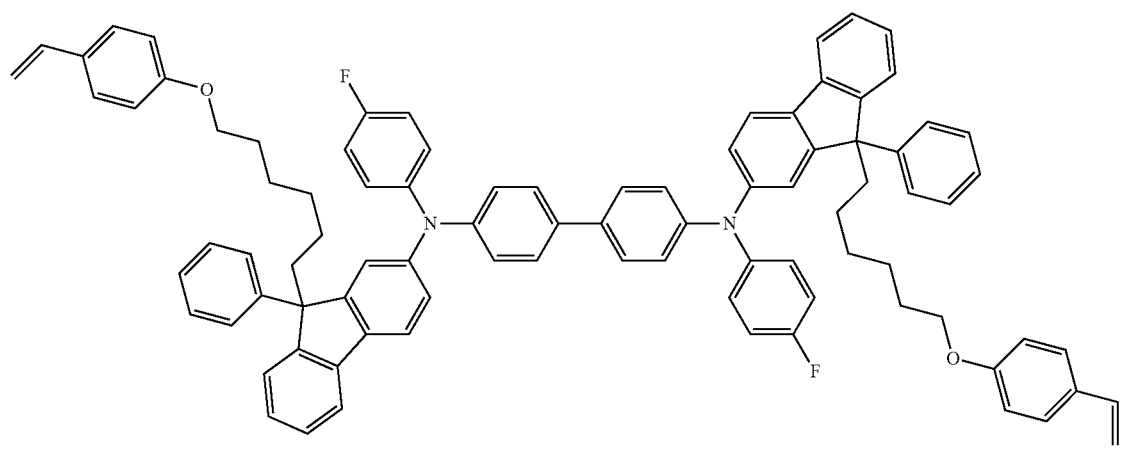
Compound 21
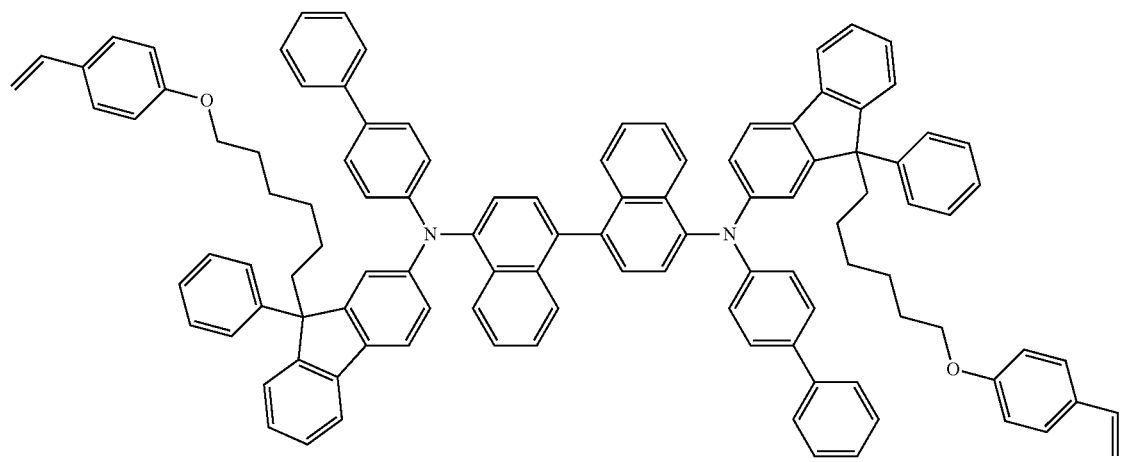

Compound 22
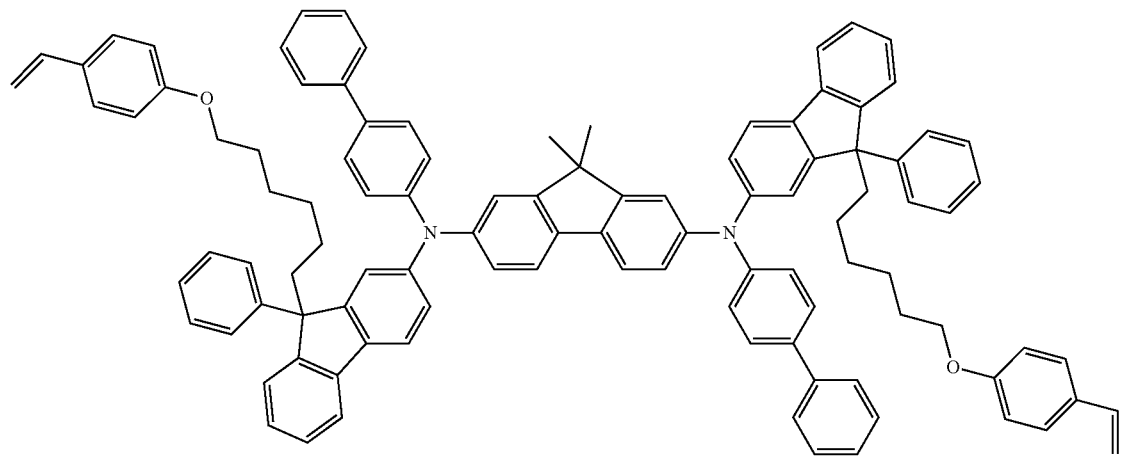
Compound 23
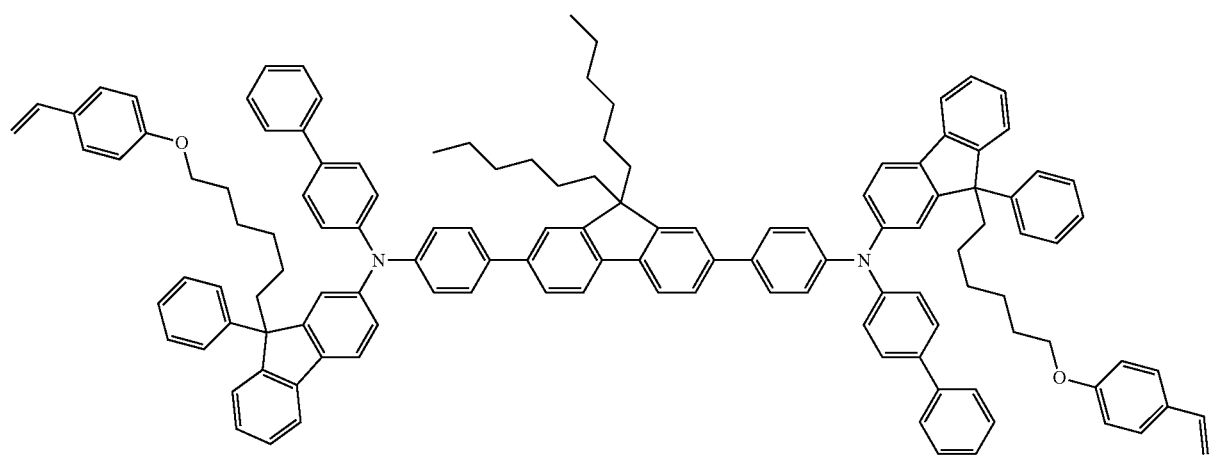
Compound 24
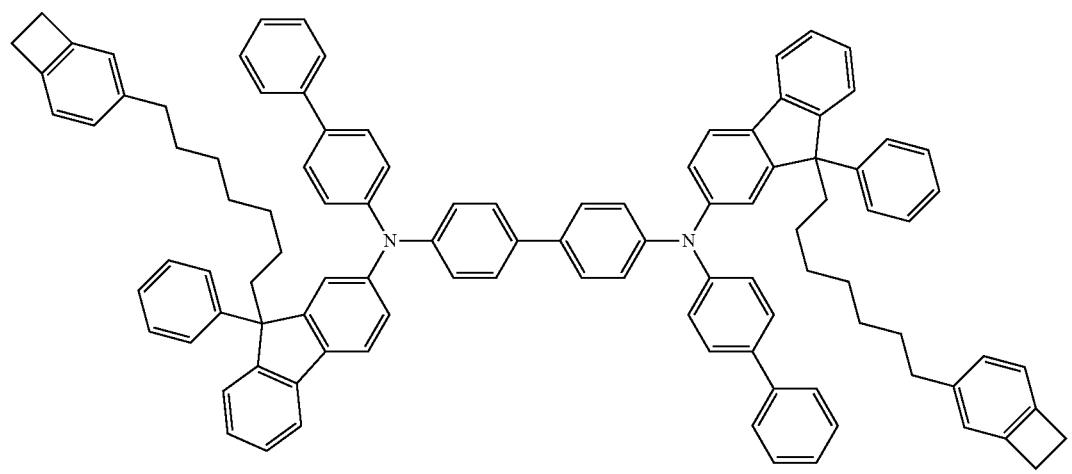

-continued
Compound 25
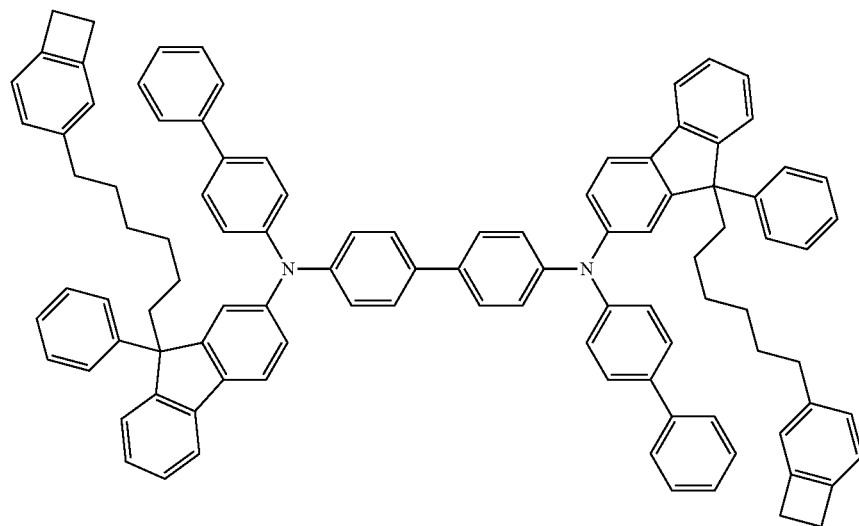
Compound 26
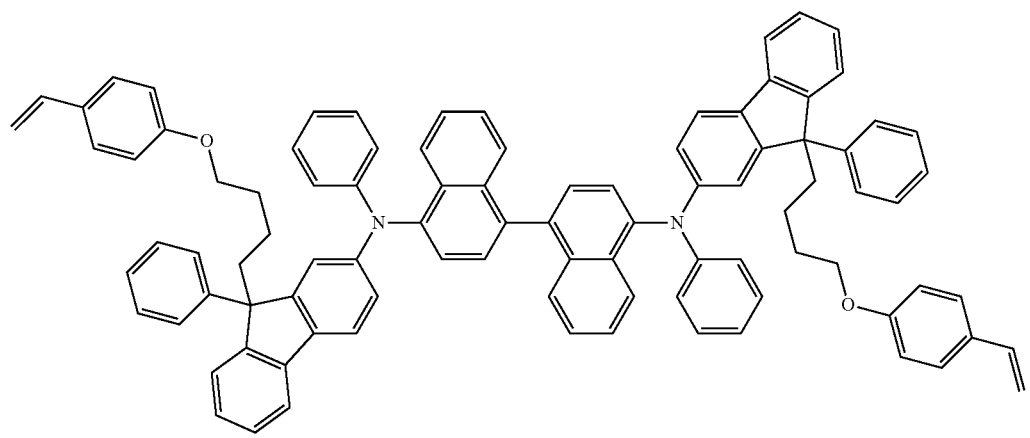
Compound 27
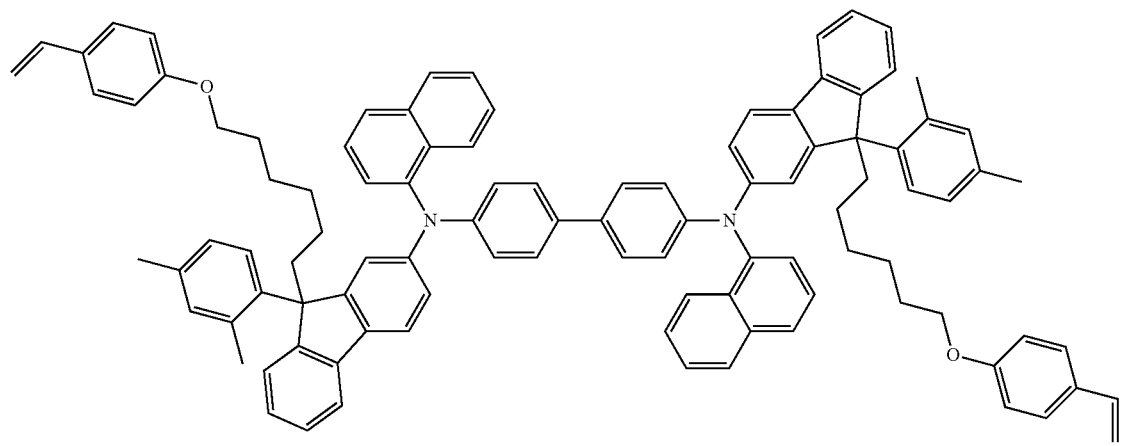

Compound 28
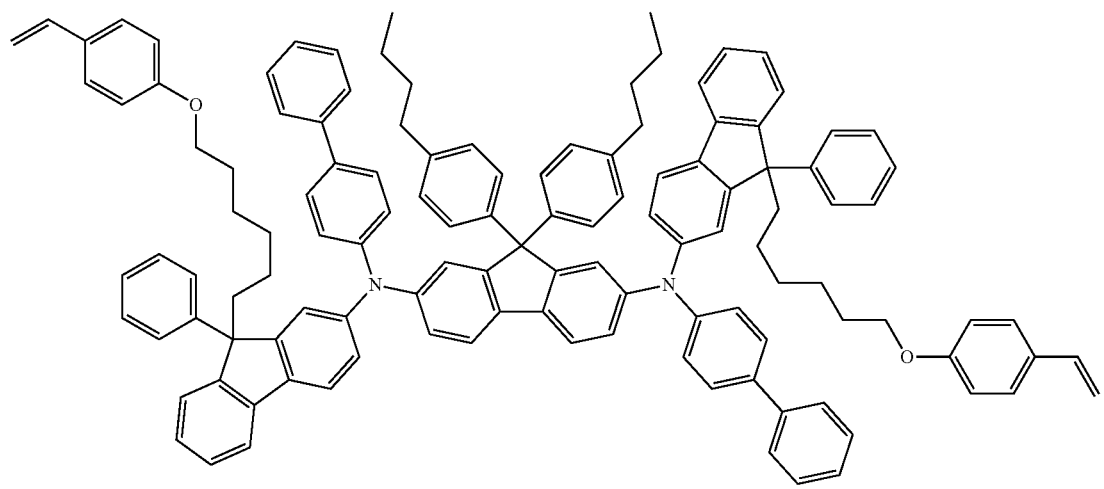
Compound 29
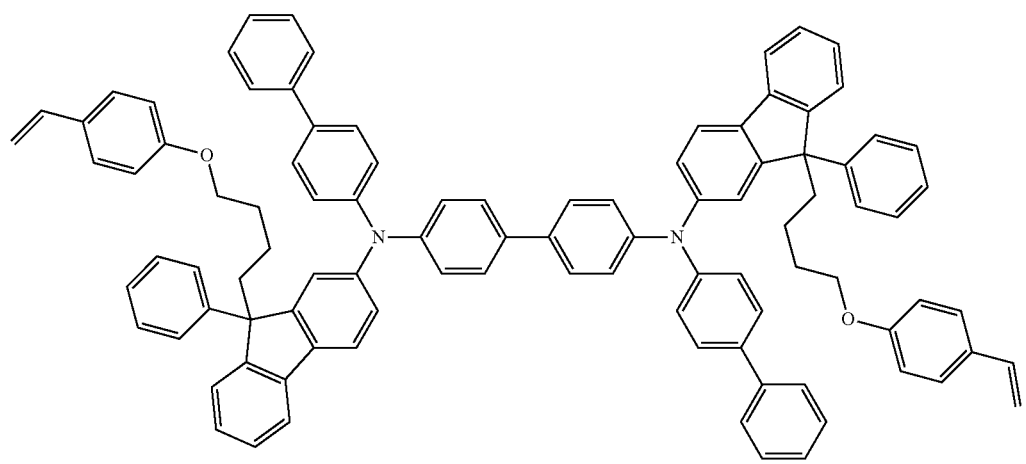
Compound 30
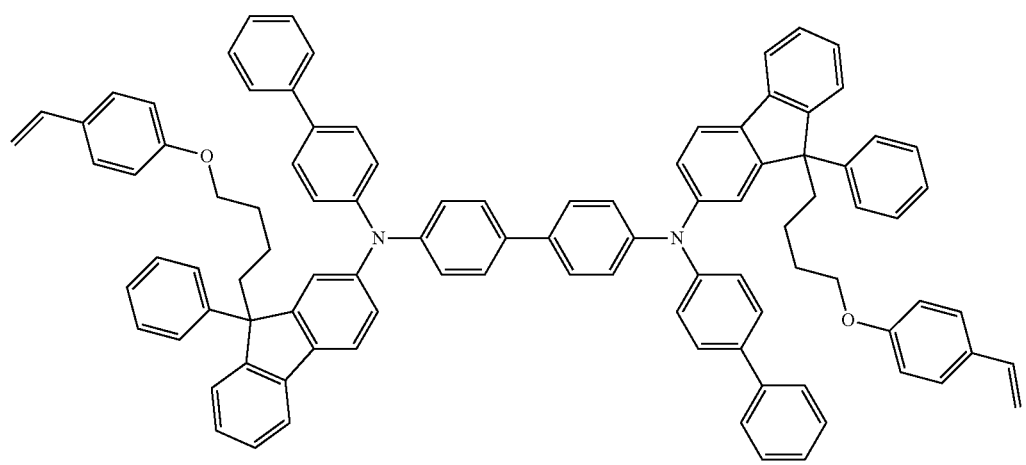

-continued
Compound 31
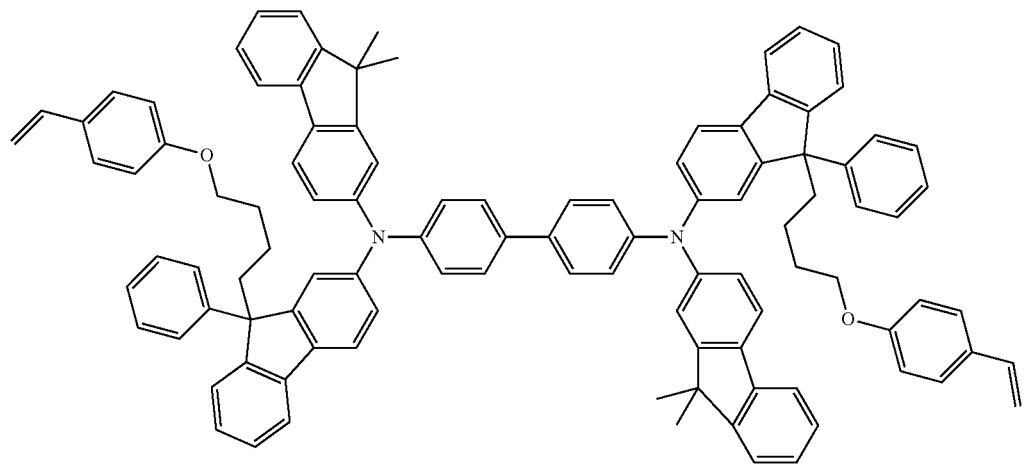
Compound 32
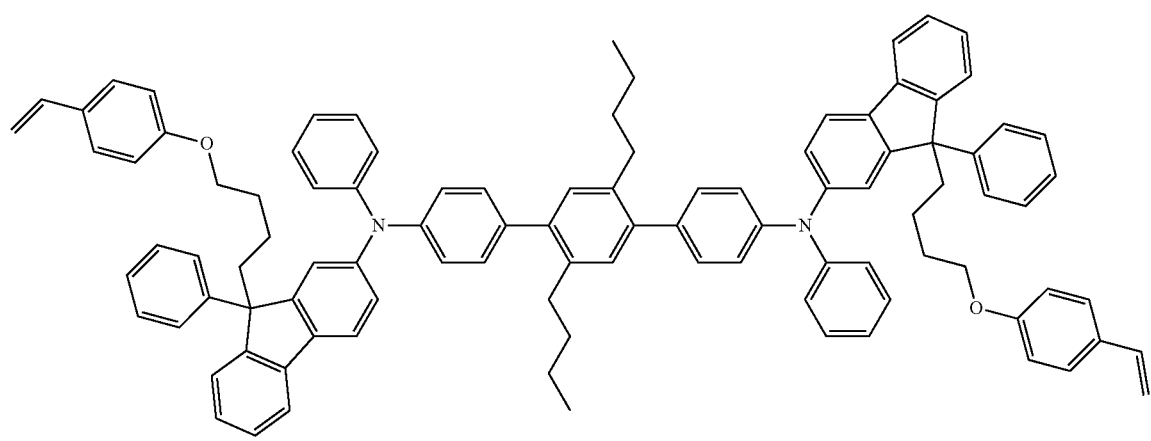
Compound 33
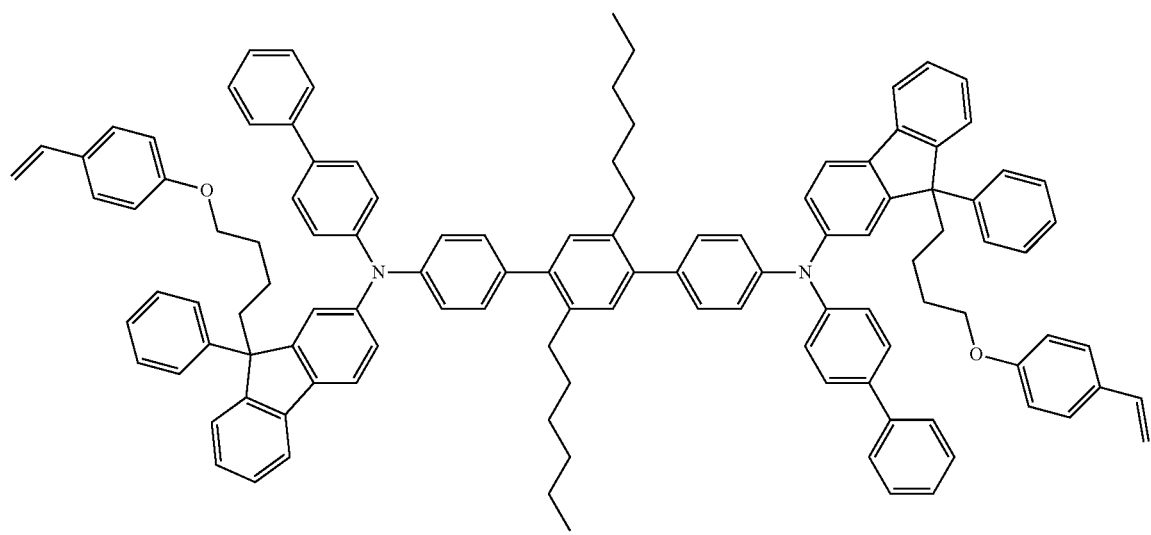

-continued
Compound 34
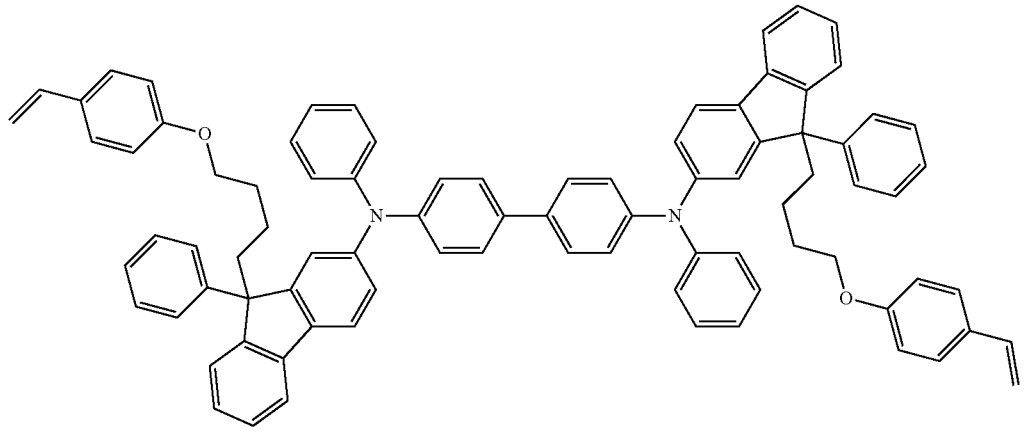
Compound 35
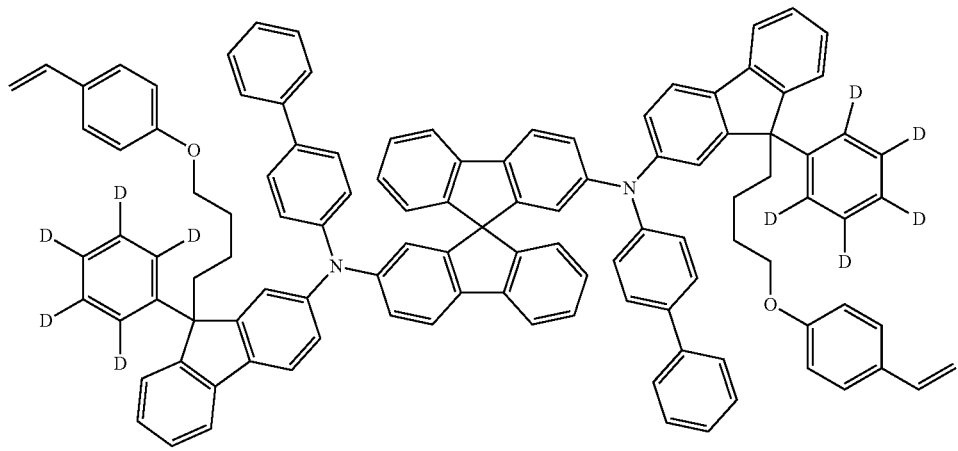
Compound 36
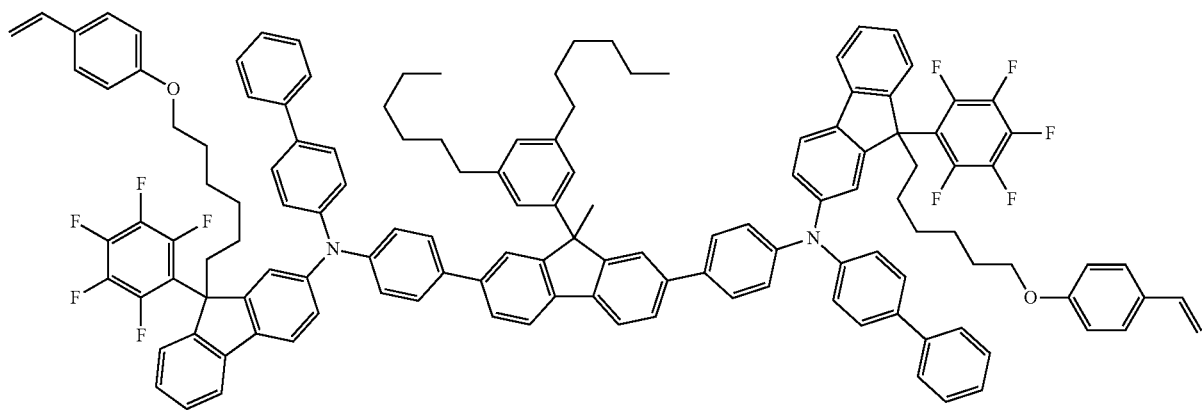

Compound 37
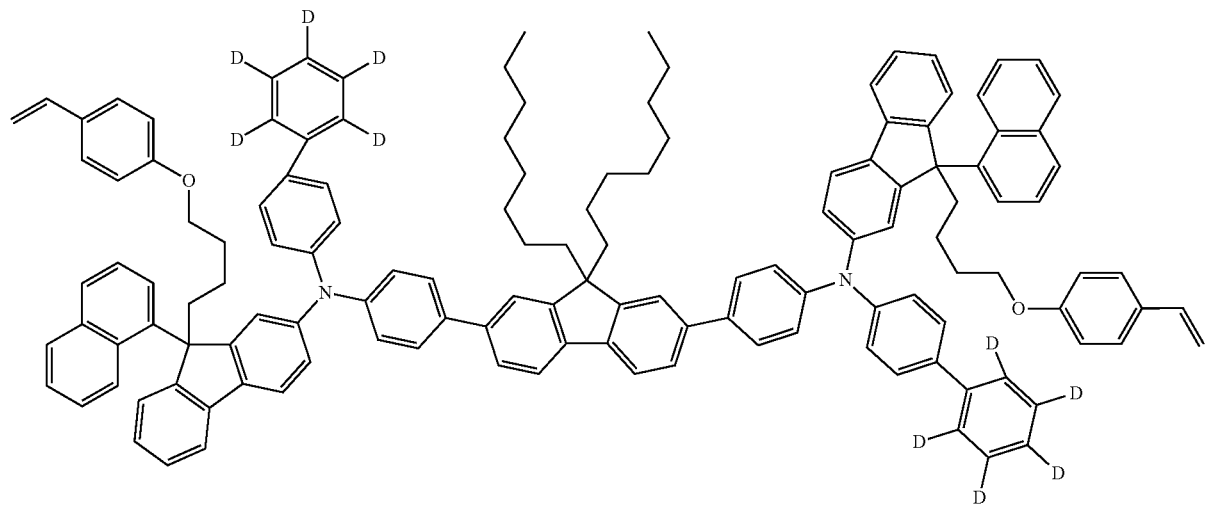
Compound 38
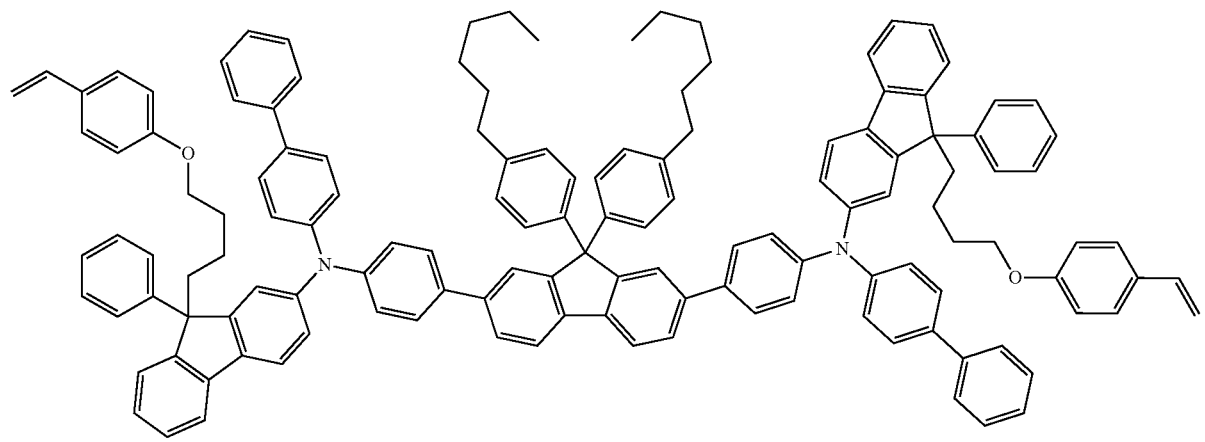
Compound 39
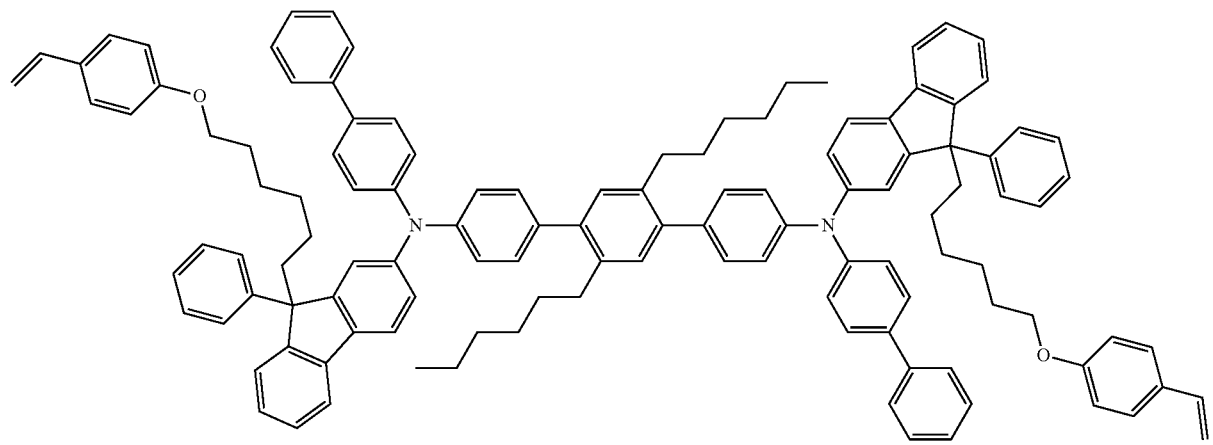

-continued
Compound 40
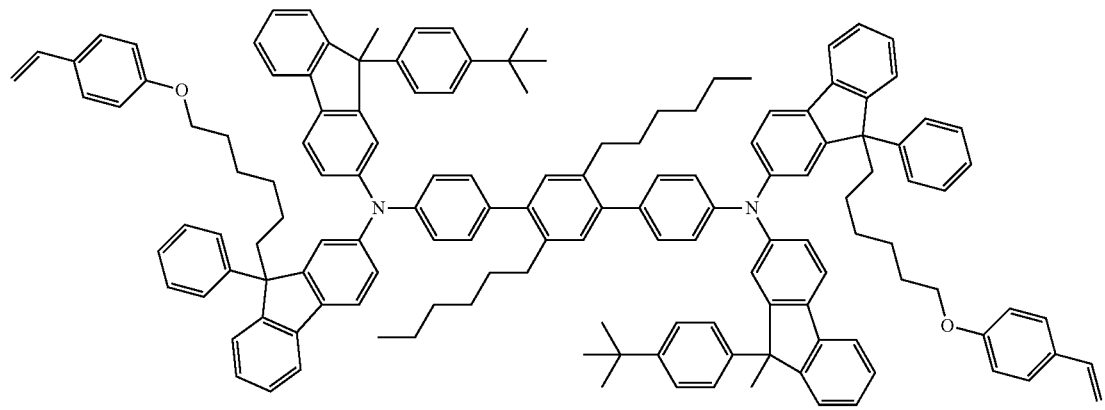
Compound 41
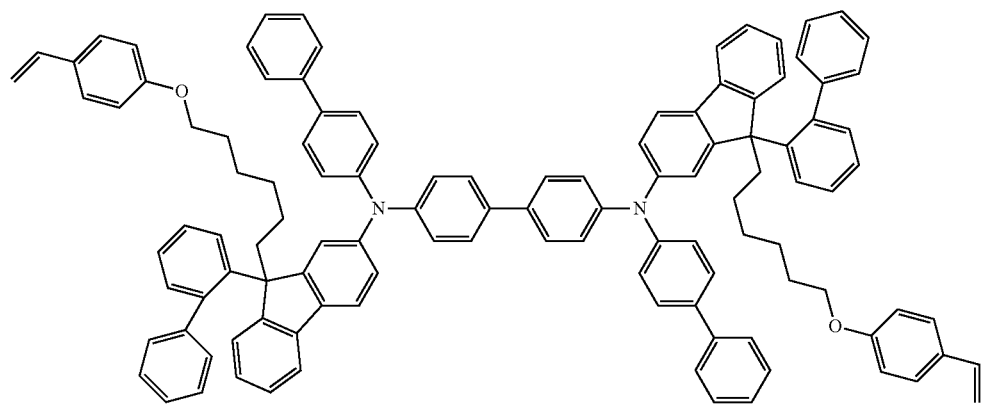
Compound 42
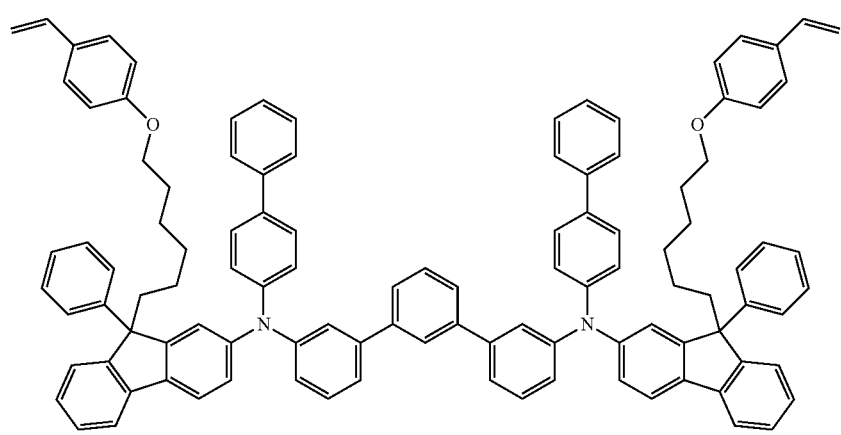

-continued
Compound 43
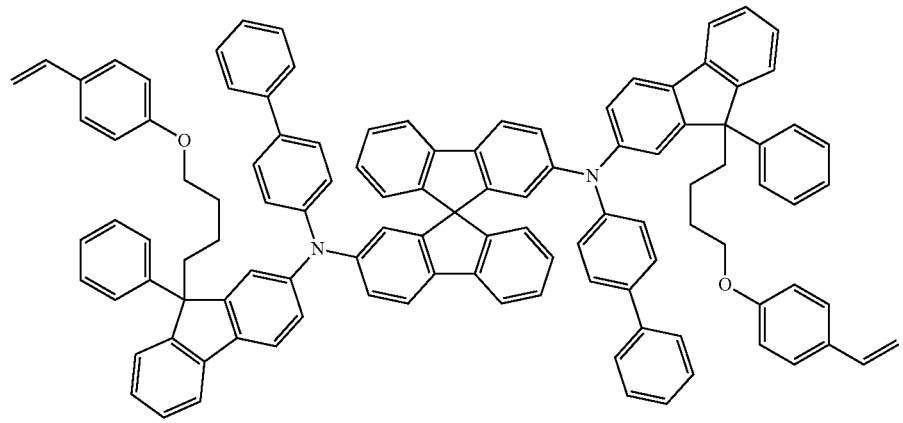
Compound 44
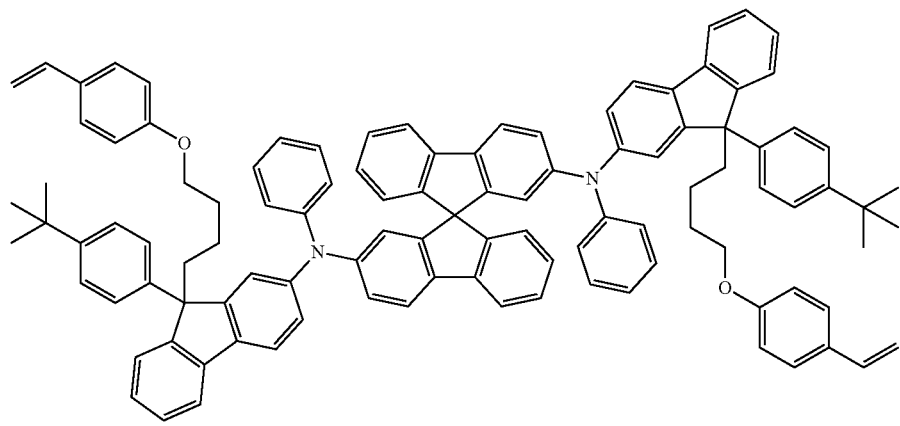
Compound 45
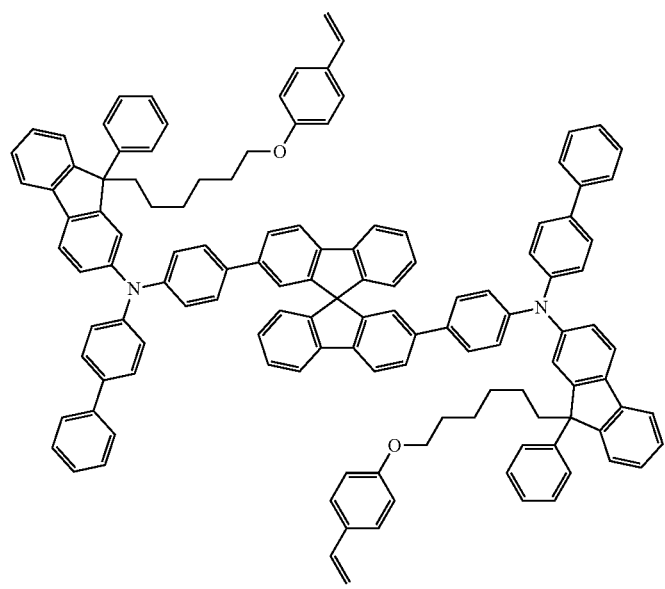

Compound 46
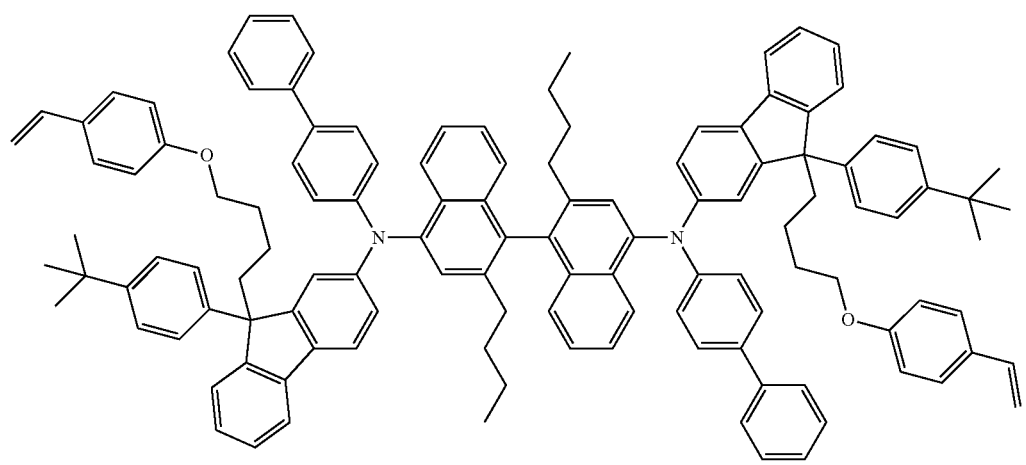
Compound 47
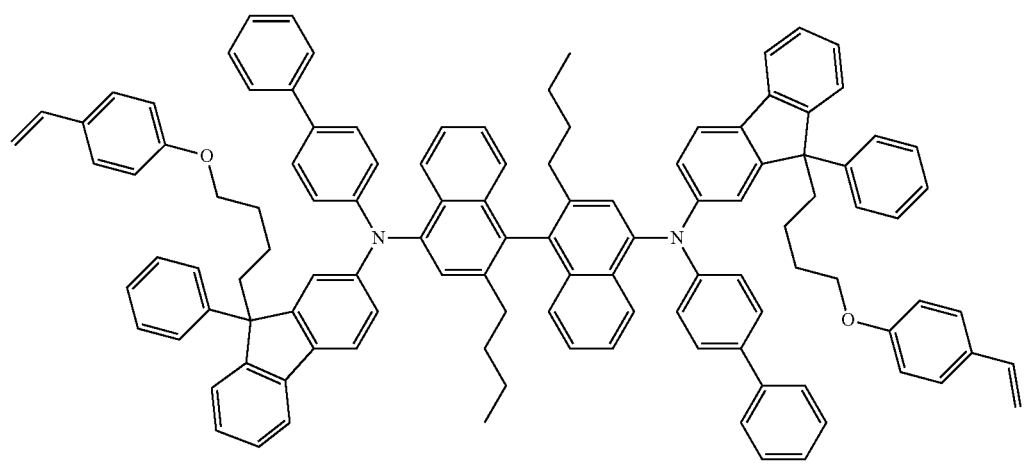
Compound 48
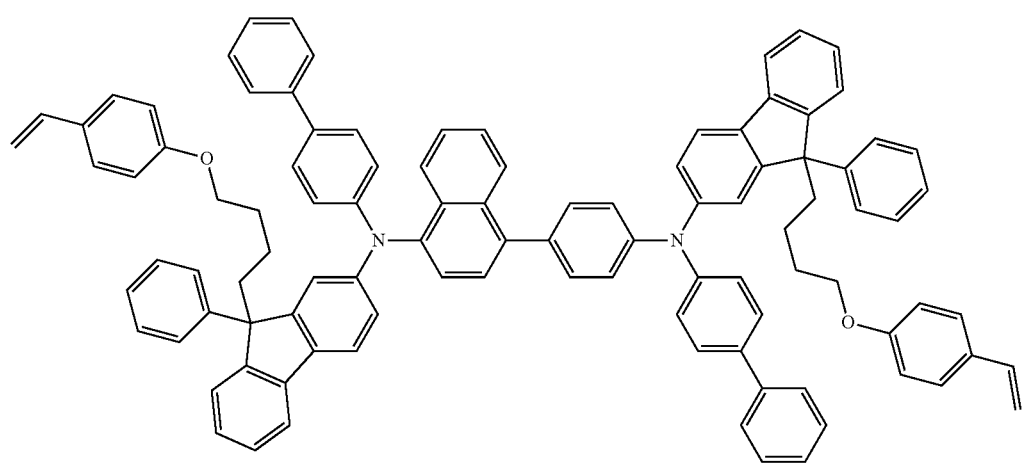

The fluorene-based compound according to an exemplary embodiment of the present specification may be prepared by a preparation method to be described below.

For example, for the fluorene-based compound of Formula 1, a core structure may be prepared as in the following Reaction Formula 1. The substituent may be bonded by a method known in the art, and the kind and position of the substituent or the number of substituents may be changed according to the technology known in the art.

<General Preparation Method of Formula 1>

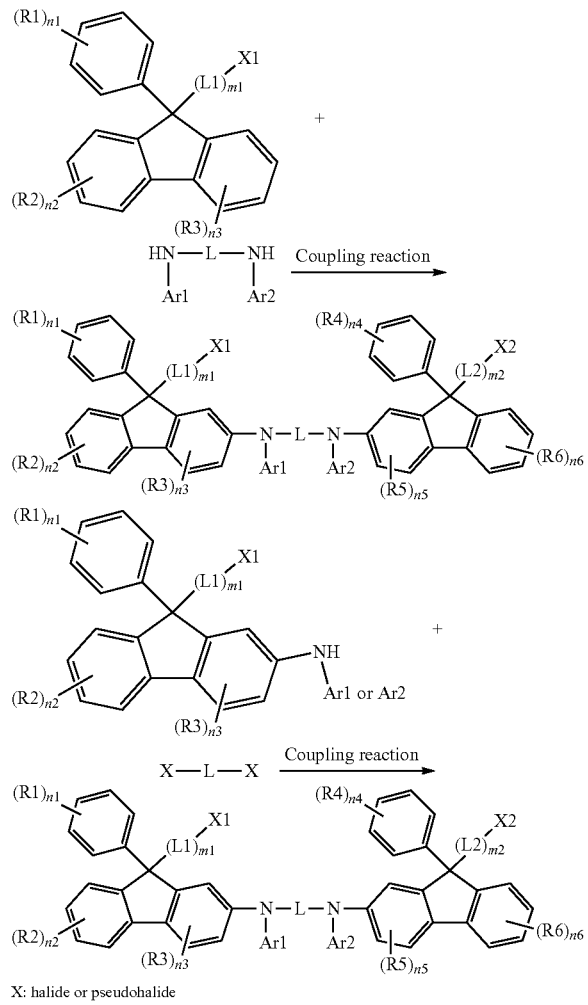

X: halide or pseudohalide

The substituents of the preparation method are the same as the definition of the substituents of Formula 1.

An exemplary embodiment of the present specification provides a coating composition comprising the above-described fluorene-based compound.

In an exemplary embodiment of the present specification, the coating composition comprises the fluorene-based compound and a solvent.

In an exemplary embodiment of the present specification, the coating composition may further comprise a polymer compound. When the coating composition further comprises a polymer compound, ink characteristics of the coating composition may be enhanced. That is, a coating composition further comprising the polymer compound may provide a viscosity suitable for coating or inkjet printing.

In an exemplary embodiment of the present specification, the coating composition may be in a liquid phase. The "liquid phase" means that the coating composition is in a liquid state at room temperature under atmospheric pressure.

In an exemplary embodiment of the present specification, the solvent is exemplified as, for example, a chlorine-based solvent such as chloroform, methylene chloride, 1,2-dichloroethane, 1,1,2-trichloroethane, chlorobenzene, and o-dichlorobenzene; an ether-based solvent such as tetrahydrofuran and dioxane; an aromatic hydrocarbon-based solvent such as toluene, xylene, trimethylbenzene, and mesitylene; an aliphatic hydrocarbon-based solvent such as cyclohexane, methylcyclohexane, n-pentane, n-hexane, n-heptane, n-octane, n-nonane, and n-decane; a ketone-based solvent such as acetone, methyl ethyl ketone, cyclohexanone, isophorone, tetralone, decalone, and acetylacetone; an ester-based solvent such as ethyl acetate, butyl acetate, and ethyl cellosolve acetate; a polyhydric alcohol such as ethylene glycol, ethylene glycol monobutyl ether, ethylene glycol monoethyl ether, ethylene glycol monomethyl ether, dimethoxy ethane, propylene glycol, diethoxymethane, triethylene glycol monoethyl ether, glycerin, and 1,2-hexanediol, and derivatives thereof; an alcohol-based solvent such as methanol, ethanol, propanol, isopropanol, and cyclohexanol; a sulfoxide-based solvent such as dimethyl sulfoxide; an amide-based solvent such as N-methyl-2-pyrrolidone and N,N-dimethylformamide; and a solvent such as tetralin, but the solvent is sufficient as long as the solvent may dissolve or disperse the fluorene derivative according to an exemplary embodiment of the present invention, and is not limited thereto.

In another exemplary embodiment, the solvents may be used either alone or in a mixture of two or more solvents.

In an exemplary embodiment of the present specification, the coating composition may further comprise one or two or more additives selected from the group consisting of a thermal polymerization initiator and a photopolymerization initiator.

In an exemplary embodiment of the present specification, as a result of measuring the fluorene-based compound of Formula 1 by a differential scanning calorimeter (DSC), a difference in temperature between an exothermic peak and an endothermic peak before the exothermic peak is 20° C. or more.

The difference in temperature between the exothermic peak and the endothermic peak before the exothermic peak may be 20° C. to 200° C.

The differential scanning calorimeter (DSC) means a device which can quantitatively measure variables such as a change in enthalpy of a sample to heat based on a quantitative analysis of the sample and a change in area of a peak during the denaturalization of the sample from positions, shapes, and the number of peaks obtained by showing a flow of heat as a function of temperature from the measurement of an amount of energy (enthalpy) required to maintain the difference in temperature between the sample and a reference material as zero while changing the temperatures of the sample and the reference material at a predetermined rate by a program.

In an exemplary embodiment of the present specification, the coating composition does not further comprise a p-doping material.

In an exemplary embodiment of the present specification, the coating composition further comprises a p-doping material.

In the present specification, the p-doping material means a material which allows a host material to have p-semiconductor characteristics. The p-semiconductor characteristics mean characteristics that electrons are injected or transported at the highest occupied molecular orbit (HOMO) energy level, that is, characteristics of a material having large hole conductivity.

According to an exemplary embodiment of the present specification, the p-doping material may be F4TCNQ; or a compound comprising a boron anion.

In an exemplary embodiment of the present specification, the p-doping material may be F4TCNQ or an F arylborate-based compound, such as the following Formulae 4-1 to 4-3, but is not limited.

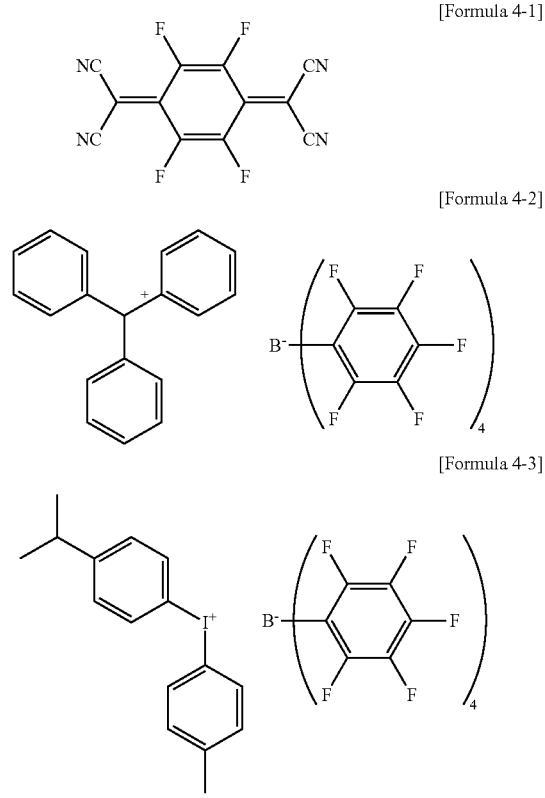

[Formula 4-1]

[Formula 4-2]

[Formula 4-3]

In the present specification, the p-doping material is sufficient as long as the material is a material which allows the host material to have p-semiconductor characteristics, one or two or more thereof may be used, and the kind thereof is not limited.

In an exemplary embodiment of the present specification, the content of the p-doping material is 0 wt % to 50 wt % based on the fluorene-based compound of Formula 1.

In an exemplary embodiment of the present specification, the content of the p-doping material is 0 to 30 wt % based on the total solid content of the coating composition. In an exemplary embodiment of the present specification, it is preferred that the content of the p-doping material is 1 to 30 wt % based on the total solid content of the coating composition, and in another exemplary embodiment, it is more preferred that the content of the p-doping material is 10 to 30 wt % based on the total solid content of the coating composition.

In another exemplary embodiment, the coating composition may further comprise: a single molecule comprising a thermosetting group or a photocurable group; or a single molecule comprising an end group capable of forming a polymer by heat. As described above, the single molecule comprising a thermosetting group or a photocurable group; or the single molecule comprising an end group capable of forming a polymer by heat may be a compound having a molecular weight of 3,000 g/mol or less. According to an example, the single molecule may have a molecular weight of 1,000 g/mol to 3,000 g/mol.

In an exemplary embodiment of the present specification, the coating composition further comprises: a single molecule having a molecular weight of 2,000 g/mol or less and comprising a thermosetting group or a photocurable group; or a single molecule having a molecular weight of 2,000 g/mol or less and comprising an end group capable of forming a polymer by heat.

The single molecule comprising a thermosetting group or a photocurable group; or the single molecule comprising an end group capable of forming a polymer by heat may mean aryl of phenyl, biphenyl, fluorene, and naphthalene; arylamine; or a single molecule in which a thermosetting group or a photocurable group or an end group capable of forming a polymer by heat is substituted with fluorene.

In another exemplary embodiment, the coating composition has a viscosity of 2 cP to 15 cP.

In an exemplary embodiment of the present specification, the coating composition has a thin film retention rate of 95% or more in a thin film retention test, after a heat treatment at 250° C. or less. The coating composition of the present invention has excellent resistance to a solvent such as toluene and cyclohexanone because the thin film retention rate in the thin film retention test is 95% or more after the heat treatment at 250° C. or less.

In the thin film retention test, a thin film is first formed by spin-coating the coating composition onto a substrate (for example, glass, and the like), a heat treatment is performed in a nitrogen atmosphere, and then UV absorbance of the thin film is measured. Thereafter, the thin film retention rate is measured by dipping the thin film into a solvent such as toluene and cyclohexanone for about 10 minutes, drying the thin film, and then measuring UV absorbance of the thin film to compare the sizes of UV absorbance maximum peaks before and after dipping the thin film into the solvent (the size of the UV absorbance maximum peak after dipping the thin film into the solvent/the size of the UV absorbance maximum peak before dipping the thin film into the solvent× 100).

The present specification also provides an organic light emitting device formed by using the coating composition.

An exemplary embodiment of the present specification comprises: a first electrode; a second electrode; and an organic material layer having one or more layers provided between the first electrode and the second electrode, and one or more layers of the organic material layer are formed by using the coating composition or a cured product thereof. The cured product of the coating composition means a state where the coating composition is cured by a heat treatment or a light treatment.

In an exemplary embodiment of the present specification, the organic material layer comprising the coating composition or the cured product thereof is a hole transport layer, a hole injection layer, or a layer which simultaneously transports and injects holes.

In another exemplary embodiment, the organic material layer comprising the coating composition or the cured product thereof is a light emitting layer.

In still another exemplary embodiment, the organic material layer comprising the coating composition or the cured product thereof is a light emitting layer, and the light emitting layer comprises the fluorene-based compound as a host of the light emitting layer.

In an exemplary embodiment of the present specification, the organic light emitting device further comprisies one or two or more layers selected from the group consisting of a hole injection layer, a hole transport layer, a layer which simultaneously injects and transports holes, an electron transport layer, an electron injection layer, a layer which simultaneously injects and transports electrons, an electron blocking layer, and a hole blocking layer.

In an exemplary embodiment of the present specification, the first electrode is an anode, and the second electrode is a cathode.

According to another exemplary embodiment, the first electrode is a cathode, and the second electrode is an anode.

In still another exemplary embodiment, the organic light emitting device may be an organic light emitting device having a structure (normal type) in which an anode, an organic material layer having one or more layers, and a cathode are sequentially stacked on a substrate.

In yet another exemplary embodiment, the organic light emitting device may be an organic light emitting device having a reverse-direction structure (inverted type) in which a cathode, an organic material layer having one or more layer, and an anode are sequentially stacked on a substrate.

The organic material layer of the organic light emitting device of the present specification may also be composed of a single-layered structure, but may be composed of a multi-layered structure in which an organic material layer having two or more layers is stacked. For example, the organic light emitting device of the present invention may have a structure comprising a hole injection layer, a hole transport layer, a layer which simultaneously injects and transports holes, a light emitting layer, an electron transport layer, an electron injection layer, a layer which simultaneously injects and transport electrons, and the like as an organic material layer. However, the structure of the organic light emitting device is not limited thereto, and may comprise a fewer number of organic layers.

In the organic light emitting device of the present specification, [a substrate/a positive electrode/a hole injection layer/a hole transport layer/a light emitting layer/an electron injection layer/an electron transport layer/a negative electrode] may be stacked in this order.

In the organic light emitting device of the present specification according to another exemplary embodiment, [a substrate/a positive electrode/a hole injection layer/a hole transport layer/a light emitting layer/a layer which simultaneously injects and transport electrons/a negative electrode] may be stacked in this order.

For example, the structure of the organic light emitting device according to an exemplary embodiment of the present specification is exemplified in FIG. 1.

FIG. 1 exemplifies a structure of an organic light emitting device in which an anode 201, a hole injection layer 301, a hole transport layer 401, a light emitting layer 501, a layer which simultaneously injects and transport electrons 601, and a cathode 701 are sequentially stacked on a substrate 101.

FIG. 1 exemplifies an organic light emitting device, and the organic light emitting device is not limited thereto.

When the organic light emitting device comprises a plurality of organic material layers, the organic material layers may be formed of the same material or different materials.

The organic light emitting device of the present specification may be manufactured by the materials and methods known in the art, except that one or more layers of the organic material layer are formed by using a coating composition comprising the fluorene-based compound.

For example, the organic light emitting device of the present specification may be manufactured by sequentially stacking an anode, an organic material layer, and a cathode on a substrate. In this case, the organic light emitting device may be manufactured by depositing a metal or a metal oxide having conductivity, or an alloy thereof on a substrate to form an anode, forming an organic material layer comprising a hole injection layer, a hole transport layer, a light emitting layer, and an electron transport layer thereon through a deposition process, a solution process, the like, and then depositing a material, which may be used as a cathode, thereon, by using a physical vapor deposition (PVD) method such as sputtering or e-beam evaporation. In addition to the method described above, an organic light emitting device may be made by sequentially depositing a cathode material, an organic material layer, and an anode material on a substrate.

The present specification also provides a method for manufacturing an organic light emitting device formed by using the coating composition.

Specifically, in an exemplary embodiment of the present specification, the method comprises: preparing a substrate; forming a first electrode on the substrate; forming an organic material layer having one or more layers on the first electrode; and forming a second electrode on the organic material layer, and one or more layers of the organic material layer are formed by using the coating composition.

According to an exemplary embodiment of the present specification, the organic material layer formed by using the coating composition is formed by using a solution process.

In an exemplary embodiment of the present specification, the organic material layer formed by using the coating composition is formed by using spin coating.

In another exemplary embodiment, the organic material layer formed by using the coating composition is formed by a printing method.

In still another exemplary embodiment of the present specification, examples of the printing method comprise inkjet printing, nozzle printing, offset printing, transfer printing or screen printing, and the like, but are not limited thereto.

For the coating composition according to an exemplary embodiment of the present specification, a solution process is suitable due to the structural characteristics, so that the organic material layer may be formed by a printing method, and as a result, there is an economic effect in terms of time and costs when a device is manufactured.

In an exemplary embodiment of the present specification, the forming of the organic material layer formed by using the coating composition comprises: coating the coating composition onto the first electrode which is a cathode or an anode; and subjecting the coated coating composition to a heat treatment or a light treatment.

In an exemplary embodiment of the present specification, a heat treatment temperature in the subjecting of the coated coating composition to the heat treatment is 85° C. to 250° C.

In another exemplary embodiment, a heat treatment time in the subjecting of the coated coating composition to the heat treatment may be 1 minute to 1 hour.

In an exemplary embodiment of the present specification, when the coating composition does not comprise an additive, it is preferred that a cross-linkage proceeds by performing a heat treatment at a temperature of 100° C. to 250° C., and it is more preferred that a cross-linkage proceeds at a temperature of 120° C. to 200° C. Further, the coating composition of the present specification may further comprise an initiator, but it is more preferred that the initiator is not used.

When the forming of the organic material layer formed by using the coating composition comprises the subjecting of the coated coating composition to the heat treatment or the light treatment, a plurality of fluorene-based compounds included in the coating composition may form a cross-linkage, thereby providing an organic material layer comprising a thin-filmed structure. In this case, it is possible to prevent the organic material layer from being dissolved or morphologically affected or decomposed by a solvent when another layer is stacked on the surface of the organic material layer formed by using the coating composition.

Therefore, when the organic material layer formed by using the coating composition is formed by a method comprising the subjecting of the coated coating composition to the heat treatment or the light treatment, resistance to a solvent is increased, so that a plurality of layers may be formed by repeatedly carrying out solution deposition and cross-linking methods, and stability is increased, so that service life characteristics of the device may be increased.

Further, the fluorene-based compound according to an exemplary embodiment of the present specification may comprise fluorene and an amine group to comprise a fluorene-based compound alone in an organic material layer, may make a film prepared from a coating composition comprising a fluorene-based compound thinned through a heat treatment or a light treatment, and may comprise a material, which is obtained by using a coating composition mixed with another monomer, as a copolymer. In addition, the fluorene-based compound may comprise a material obtained by using a coating composition mixed with another polymer, as a copolymer or a mixture.

As the anode material, materials having a high work function are usually preferred so as to facilitate the injection of holes into an organic material layer. Specific examples of the anode material which may be used in the present invention comprise: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline; and the like, but are not limited thereto.

As the cathode material, materials having a low work function are usually preferred so as to facilitate the injection of electrons into an organic material layer. Specific examples of the cathode material comprise: a metal such as barium, magnesium, calcium, sodium, potassium, titanium, indium, yttrium, lithium, gadolinium, aluminum, silver, tin, and lead, or alloys thereof; a multi-layer structured material such as LiF/Al or $LiO_2$/Al; and the like, but are not limited thereto.

The hole injection layer is a layer which injects holes from an electrode, and a hole injection material is preferably a compound which has a capability of transporting holes, and thus has an effect of injecting holes at an anode and an excellent effect of injecting holes for a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the anode material and the HOMO of the neighboring organic material layer. Specific examples of the hole injection material comprise metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based electrically conductive polymers, and the like, but are not limited thereto.

The hole transport layer is a layer which accepts holes from a hole injection layer and transports the holes to a light emitting layer, and a hole transport material is suitably a material having high hole mobility which may accept holes from an anode or a hole injection layer and transfer the holes to a light emitting layer. Specific examples thereof comprise arylamine-based organic materials, electrically conductive polymers, block copolymers having both conjugated portions and non-conjugated portions, and the like, but are not limited thereto.

The light emitting material is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof comprise: an 8-hydroxy-quinoline aluminum complex ($Alq_3$); carbazole-based compounds; dimerized styryl compounds; BAlq; 10-hydroxybenzoquinoline-metal compounds; benzoxazole-based, benzothiazole-based and benzimidazole-based compounds; poly(p-phenylenevinylene) (PPV)-based polymers; spiro compounds; polyfluorene, lubrene, and the like, but are not limited thereto.

The light emitting layer may comprise a host material and a dopant material. Examples of the host material comprise fused aromatic ring derivatives, or hetero ring-containing compounds, and the like. Specifically, examples of the fused aromatic ring derivatives comprise anthracene derivatives, pyrene derivatives, naphthalene derivatives, pentacene derivatives, phenanthrene compounds, fluoranthene compounds, and the like, and examples of the hetero ring-containing compounds comprise carbazole derivatives, dibenzofuran derivatives, ladder-type furan compounds, pyrimidine derivatives, and the like, but the examples thereof are not limited thereto.

Examples of the dopant material comprise an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof comprise a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof comprise styrylamine, styryldiamine, styryltriamine, styryltetramine, and the like, but are not limited thereto. Further, examples of the metal complex comprise an iridium complex, a platinum complex, and the like, but are not limited thereto.

The electron transport layer is a layer which accepts electrons from an electron injection layer and transports the electrons to a light emitting layer, and an electron transport material is suitably a material having high electron mobility which may proficiently accept electrons from a cathode and transfer the electrons to a light emitting layer. Specific examples thereof comprise: an Al complex of 8-hydroxyquinoline; a complex comprising $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof comprise cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof comprise fluorenone, anthraquinodimethane, diphenoquinone, thiopyran dioxide, oxazole, oxadiazole, triazole, imidazole, perylenetetracarboxylic acid, fluorenylidene methane, anthrone, and the like, and a derivative thereof, a metal complex compound, a nitrogen-containing 5-membered ring derivative, and the like, but are not limited thereto.

Examples of the metal complex compound comprise 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer which blocks holes from reaching a cathode, and may be generally formed under the same conditions as those of the hole injection layer. Specific examples thereof comprise an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the materials to be used.

MODE FOR INVENTION

Hereinafter, the present specification will be described in detail with reference to Examples for specifically describing the present specification However, the Examples according to the present specification may be modified in various forms, and it is not interpreted that the scope of the present specification is limited to the Examples described below. The Examples of the present specification are provided to more completely explain the present specification to a person with ordinary skill in the art.

PREPARATION EXAMPLES

Preparation Example 1. Synthesis of Compound 1

(1) Synthesis of Intermediate 3

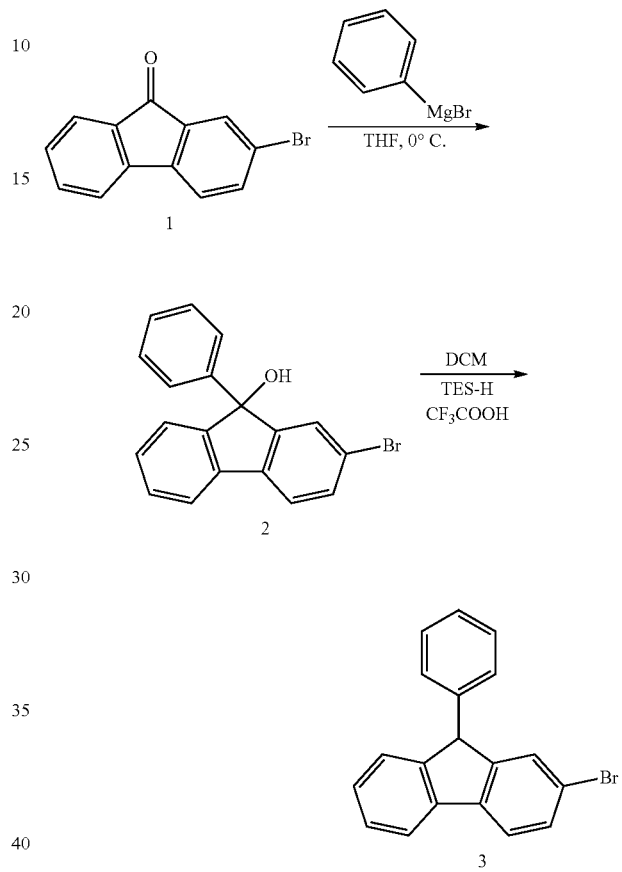

Synthesis of 2-bromo-9-phenyl-9H-fluoren-9-ol (2): A flask containing a solution having 2-bromo-9H-fluoren-9-one (1) (5 g, 19.3 mmol) dissolved in anhydrous tetrahydrofuran (THF) was put into an iced water bath. Phenylmagnesiumbromide (3 M in tetrahydrofuran [THF], 9.65 ml, 29.0 mmol) was added thereto, and the resulting mixture was stirred for 20 minutes at 0° C. The reaction was stopped with $NH_4Cl$ (aq), followed by extraction with diethyl ether ($Et_2O$). The organic layer was dried using $MgSO_4$, and the organic solvent was removed using a vacuum rotary evaporator. The residue was column purified to obtain 6.5 g (quantitative yield) of Intermediate 2.

Synthesis of 2-bromo-9-phenyl-9H-fluorene (3): After Intermediate 2 (3.6 g, 10.6 mmol) was dissolved in dichloromethane [DCM], triethylsilane (2.6 ml, 16.1 mmol) and 1.3 ml of trifluoroacetic acid were added thereto, and the resulting mixture was stirred at room temperature overnight. It was confirmed by thin layer chromatography (TLC) that Intermediate 2 disappeared, silica gel was added thereto, and the organic solvent was removed by a vacuum rotary evaporator. Column purification was performed with a silica gel, onto which the product was adsorbed, to obtain 3.26 g (yield 95%) of Intermediate 3.

(2) Synthesis of Intermediate 5

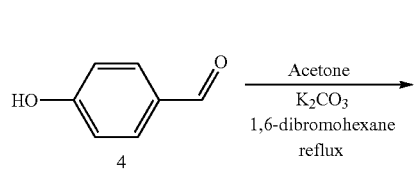

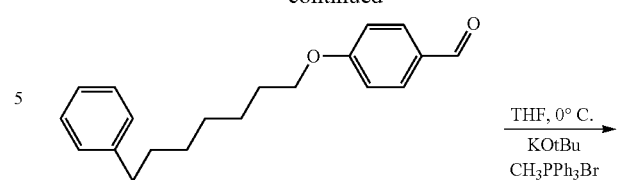

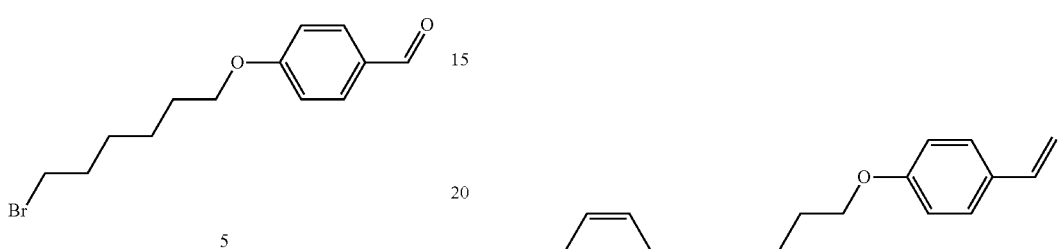

Synthesis of 4-((6-bromohexyl)oxy)benzaldehyde (5): After 4-hydroxybenzaldehyde (6.1 g, 50 mmol), potassium carbonate (10 g, 75 mmol), and 1,6-dibromohexane (15 ml, 100 mmol) were dissolved in acetone, the resulting solution was refluxed for 3 hours. After the reactant was filtered, the organic solvent was removed using a vacuum rotary evaporator. The residue was column purified to obtain 9.9 g (yield 69%) of Intermediate 5.

(3) Synthesis of Intermediate 7

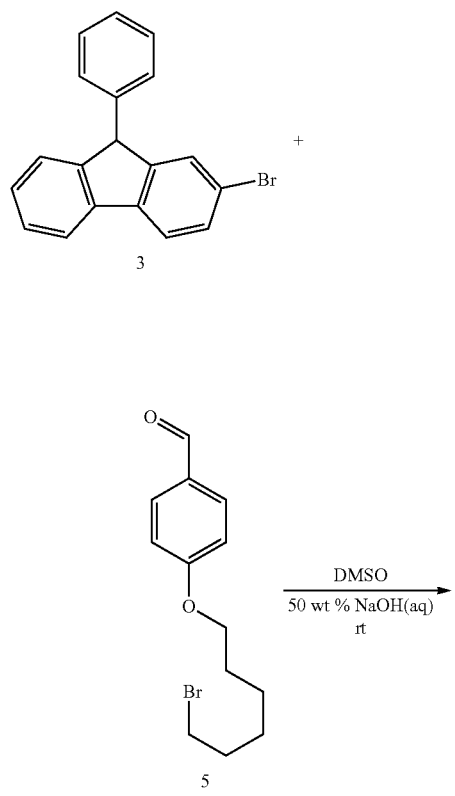

Synthesis of 4-((6-(2-bromo-9-phenyl-9H-fluoren-9-yl)hexyl)oxy)benzaldehyde (6): Intermediate 3 (3.7 g, 11.5 mmol) and Intermediate 5 (3 g, 10.5 mmol) were dissolved in 20 ml of dimethyl sulfoxide [DMSO] in an oil bath at 50° C. 0.5 ml of 50 wt % NaOH (aq) was added thereto, the resulting mixture was stirred overnight, 0.5 ml of 50 wt % NaOH (aq) was added again thereto, and the resulting mixture was further stirred for 2 hours. The reactant was added to 400 ml of water and precipitated, and then the precipitate was filtered. A solid obtained by filtering was added again to 100 ml of ethanol, the resulting mixture was stirred for about 10 minutes, and then the product was filtered again. The filter cake was dried in a vacuum oven to obtain 4.48 g (yield 81%) of Intermediate 6.

Synthesis of 2-bromo-9-phenyl-9-(6-(4-vinylphenoxy)hexyl)-9H-fluorene (7): A flask containing methyl phosphonium bromide (5.1 g, 14.3 mmol) was dipped into iced water, and then 100 ml of anhydrous tetrahydrofuran [THF] was added thereto. KOtBu (1.6 g, 14.3 mmol) was added thereto, and the resulting mixture was stirred for 30 minutes. 4-((6-(2-bromo-9-phenyl-9H-fluoren-9-yl)hexyl)oxy)benzaldehyde (3 g, 5.7 mmol) was dissolved in anhydrous tetrahydrofuran [THF], and the resulting solution was put into a reaction flask and stirred again for 1 hour. The reaction was stopped by adding water thereto, and the product was extracted with dichloromethane [DCM]. After the organic solvent was dried over MgSO$_4$ and filtered, the organic solvent was removed by using a vacuum rotary evaporator. The residue was column purified to obtain 2.63 g (yield 88%) of Intermediate 7.

(4) Synthesis of Compound 1

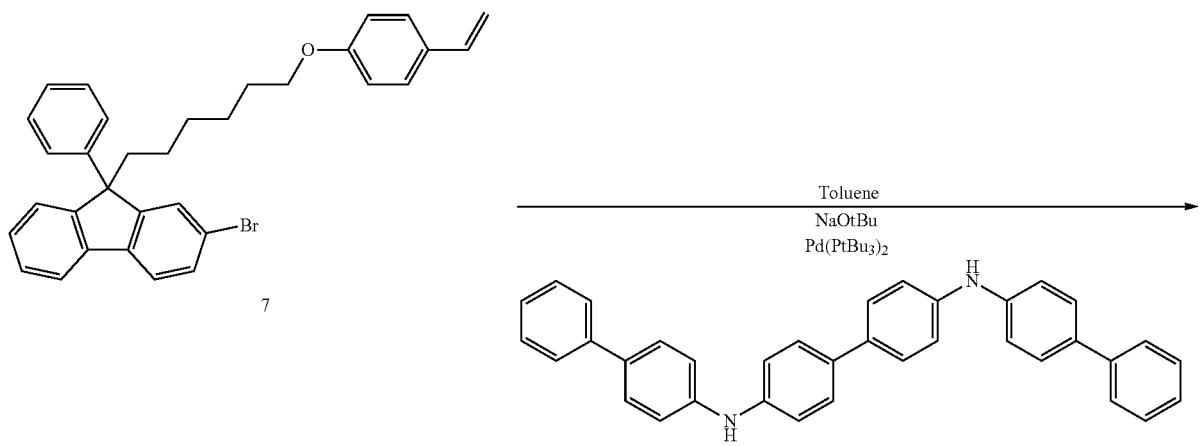

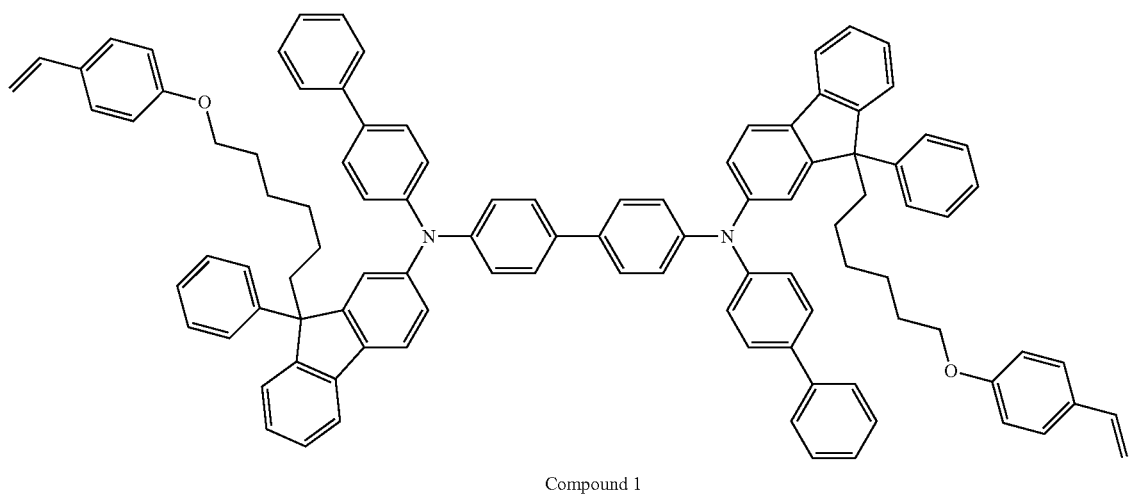

Compound 1

Synthesis of Compound 1 (N4,N4'-di([1,1'-biphenyl]-4-yl)-N4,N4'-bis(9-phenyl-9-(6-(4-vinylphenoxy)hexyl)-9H-fluoren-2-yl)-[1,1'-biphenyl]-4,4'-diamine): Intermediate 7 (700 mg, 1.34 mmol), N4,N4'-di([1,1'-biphenyl]-4-yl)-[1,1'-biphenyl]-4,4'-diamine (327 mg, 0.67 mmol), and NaOtBu (384 mg, 4 mmol) were put into a 50-ml round flask, and 7 ml of anhydrous toluene was added thereto. After the round flask containing the reactant was put into an oil bath at 90° C. and the reactant was stirred for 4 hours, the oil bath was removed, and the product was diluted with dichloromethane [DCM]. Silica gel and celite were added thereto, and the resulting mixture was stirred for 5 minutes and then filtered. After the organic solvent was removed from the filtrate by using a vacuum rotary evaporator, the residue was column purified to obtain 560 mg (yield 61%, HPLC purity 99.4%) of Compound 1.

NMR measurement value of Compound 1: $^1$H NMR (500 MHz, CD$_2$Cl$_2$) δ 7.70 (d, 2H), 7.68 (d, 2H), 7.57 (d, 4H), 7.48 (t, 8H), 7.41 (t, 4H), 7.34-7.26 (m, 8H), 7.23-7.10 (m, 26H), 6.76 (d, 4H), 6.64-6.58 (dd, 2H), 5.56 (d, 2H), 5.07 (d, 2H), 3.85 (t, 4H), 2.46-2.36 (m, 4H), 1.67-1.61 (m, 4H) 1.35-1.23 (m, 8H), 0.92-0.73 (m 4H)

Preparation Example 2. Synthesis of Compound 10

(1) Synthesis of Intermediate 10

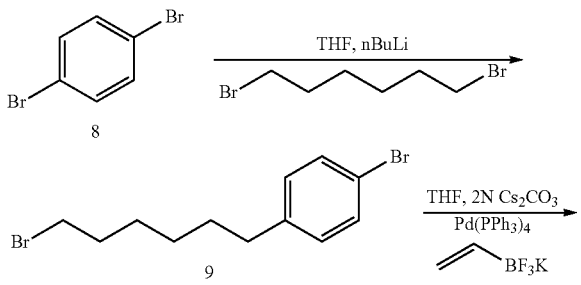

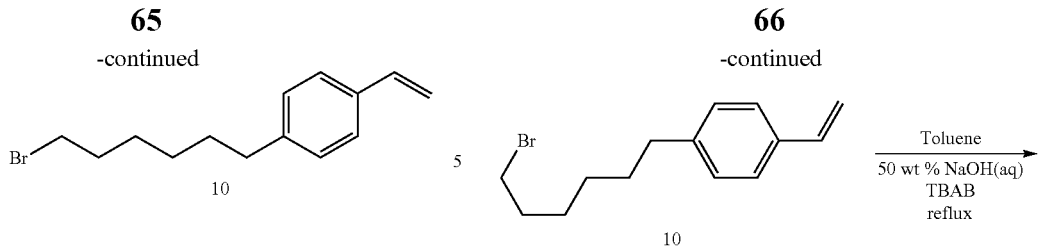

Synthesis of 1-bromo-4-(6-bromohexyl)benzene (9): After 1,4-dibromobenzene (8) (8.0 g, 33.9 mmol) was dissolved in tetrahydrofuran [THF], the temperature was lowered using a dry ice/acetone bath. nBuLi (13.6 ml, 33.9 mmol, 2.5 M in hexane) was slowly added thereto, and then the resulting mixture was stirred for 1 hour. Next, 1,6-dibromohexane (11 ml, 72 mmol) was added thereto, and then the resulting mixture was stirred overnight. The reaction was stopped with water, and the product was extracted with dichloromethane. The extract was subjected to distillation purification to obtain 5.7 g (yield 53%) of Intermediate 9.

Synthesis of 1-(6-bromohexyl)-4-vinylbenzene (10): After Intermediate 9 (3.0 g, 9.4 mmol) and vinyl trifluoroborane potassium salt (1.9 g, 14 mmol) were dissolved in tetrahydrofuran [THF], a 2 N aqueous $Cs_2CO_3$ solution and $Pd(PPh_3)_4$ (1.1 mg, 0.94 mmol) were added thereto, and the resulting mixture was stirred under a reflux condition for 6 hours. Next, water was added thereto, and the product was extracted with ethyl acetate. The organic layer was dried over $MgSO_4$, concentrated by using a vacuum rotary evaporator, and then column purified to obtain 2.06 g (yield 82%) of Intermediate 10.

(2) Synthesis of Intermediate 11

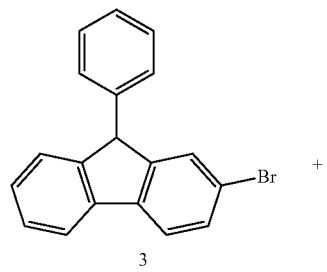

Synthesis of 2-bromo-9-phenyl-(6-(4-vinylphenyl)hexyl)-9H-fluorene (11): Intermediate 10 (532 mg, 2.0 mmol) and Intermediate 3 (642 mg, 2.0 mmol) were dissolved in 20 ml of toluene, 4.5 ml of 50 wt % NaOH was added thereto, and the resulting mixture was stirred under reflux for 12 hours. After the product was extracted with dichloromethane and dried over $MgSO_4$, the product was concentrated by using a vacuum rotary evaporator, and then column purified to obtain 788 mg (yield 78%) of Intermediate 11.

(3) Synthesis of Compound 10

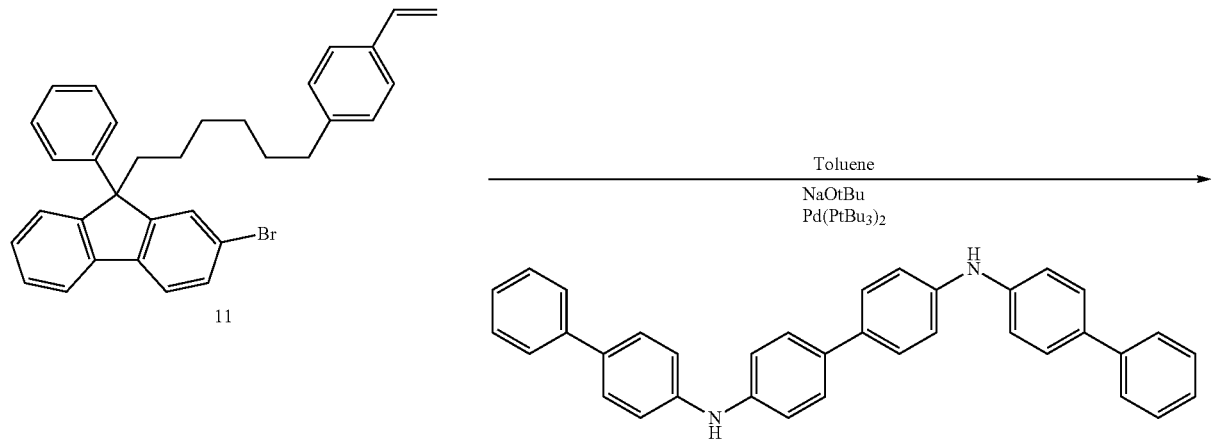

-continued

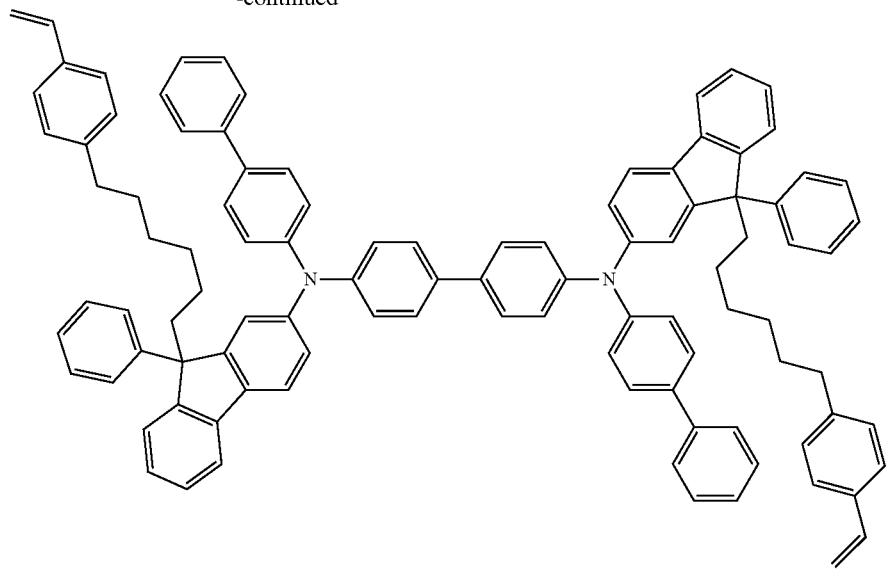

Compound 10

Synthesis of Compound 10: Intermediate 11 (788 mg, 1.56 mmol), N4,N4'-di([1,1'-biphenyl]-4-yl)-[1,1'-biphenyl]-4,4'-diamine (362 mg, 0.74 mmol), and NaOtBu (427 mg, 4.4 mmol) were put into a 50-ml round flask, and 13 ml of anhydrous toluene was added thereto. After the round flask containing the reactant was put into an oil bath at 80° C. and the reactant was stirred for 4 hours, the oil bath was removed, and the product was diluted with dichloromethane [DCM]. Silica gel and celite were added thereto, and the resulting mixture was stirred for 5 minutes and then filtered. After the organic solvent was removed from the filtrate by using a vacuum rotary evaporator, the residue was column purified to obtain 634 mg (yield 64%, HPLC purity 99.2%) of Compound 10.

NMR measurement value of Compound 10: $^1$H NMR (500 MHz, $CD_2Cl_2$) δ 7.70-7.68 (m, 4H), 7.57 (d, 4H), 7.47 (t, 8H), 7.42 (t, 4H), 7.34-7.29 (m, 4H), 7.26 (d, 4H), 7.22-7.12 (m, 26H), 7.05 (d, 4H), 6.67-6.61 (dd, 2H), 5.64 (d, 2H), 5.13 (d, 2H), 2.49 (t, 4H), 2.42-2.34 (m, 4H), 1.50-1.44 (m, 4H), 1.26-1.10 (m, 8H), 0.90-0.81 (m 4H)

Preparation Example 3. Synthesis of Compound 29

(1) Synthesis of Intermediate 12

Synthesis of 4-(4-bromobutoxy)benzaldehyde (12): 4-hydroxybenzaldehyde (6.1 g, 50 mmol), potassium carbonate (10 g, 75 mmol), and 1,4-dibromobutane (12 ml, 100 mmol) were dissolved in acetone, and then the resulting solution was refluxed for 3 hours. After the reactant was filtered, the organic solvent was removed by using a vacuum rotary evaporator, and the residue was column purified to obtain 7.7 g (yield 60%) of Intermediate 12.

(2) Synthesis of Intermediate 14

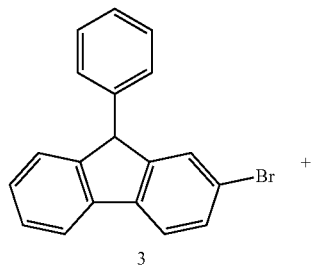

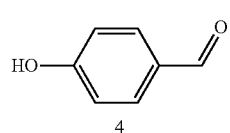

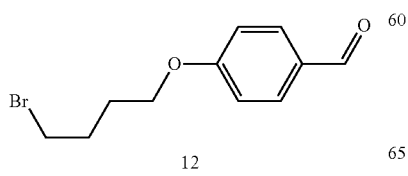

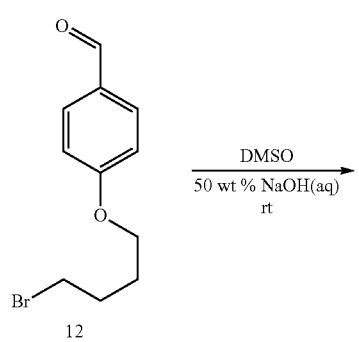

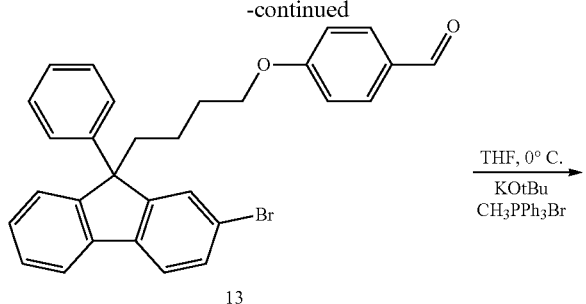

13

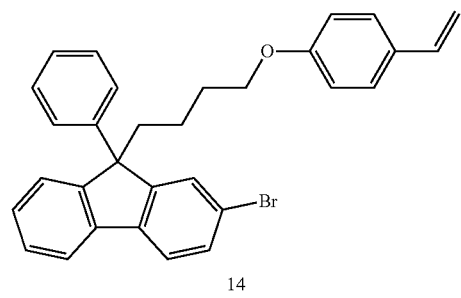

14

Synthesis of 4-(4-(2-bromo-9-phenyl-9H-fluoren-9-yl) butoxy)benzaldehyde (13): Intermediate 3 (9 g, 28 mmol) and Intermediate 12 (7 g, 27.2 mmol) were dissolved in 60 ml of dimethyl sulfoxide [DMSO] in an oil bath at 50° C. 1.5 ml of 50 wt % NaOH (aq) was added thereto, the resulting mixture was stirred overnight, 1.5 ml of 50 wt % NaOH (aq) was added again thereto, and the resulting mixture was further stirred for 2 hours. The reactant was added to 600 ml of water and precipitated, and then the precipitate was filtered. A solid obtained by filtering was added again to 100 ml of ethanol, the resulting mixture was stirred for about 10 minutes, and then the product was filtered again. The filter cake was dried in a vacuum oven to obtain 10.7 g (yield 79%) of Intermediate 13.

Synthesis of 2-bromo-9-phenyl-9-(4-(4-vinylphenoxy) butyl)-9H-fluorene (14): A flask containing methyl phosphonium bromide (7.15 g, 20 mmol) was dipped into iced water, and then 100 ml of anhydrous tetrahydrofuran [THF] was added thereto. KOtBu (2.24 g, 20 mmol) was added thereto, and the resulting mixture was stirred for 30 minutes. Intermediate 13 (5 g, 10 mmol) was dissolved in anhydrous tetrahydrofuran [THF], and the resulting solution was put into a reaction flask, and then stirred again for 1 hour. The reaction was stopped by adding water thereto, and the product was extracted with dichloromethane [DCM]. After the organic solvent was dried over $MgSO_4$ and filtered, the organic solvent was removed by using a vacuum rotary evaporator. The residue was column purified to obtain 4.45 g (yield 90%) of Intermediate 14.

(4) Synthesis of Compound 29

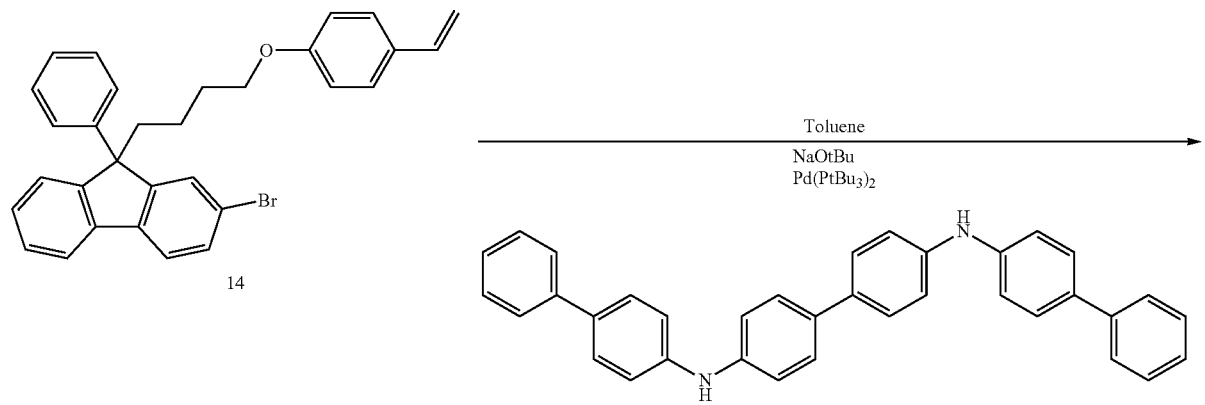

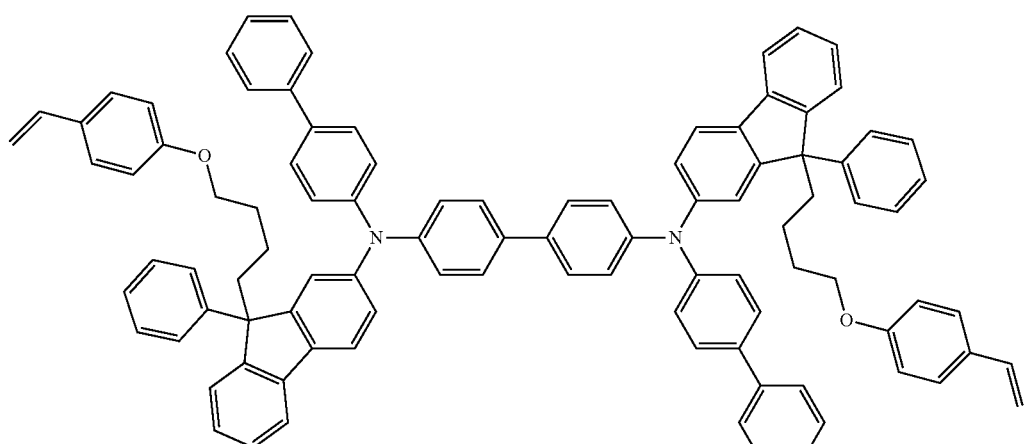

Compound 29

Synthesis of Compound 29 (N4,N4'-di([1,1'-biphenyl]-4-yl)-N4,N4'-bis(9-phenyl-9-(4-(4-vinylphenoxy)butyl)-9H-fluoren-2-yl)-[1,1'-biphenyl]-4,4'-diamine): Intermediate 14 (1.62 g, 3.27 mmol), N4,N4'-di([1,1'-biphenyl]-4-yl)-[1,1'-biphenyl]-4,4'-diamine (743 mg, 1.52 mmol), and NaOtBu (730 mg, 7.6 mmol) were put into a 50-ml round flask, and 12 ml of anhydrous toluene was added thereto. After the round flask containing the reactant was put into an oil bath at 90° C. and the reactant was stirred for 1 hour, the oil bath was removed, and the product was diluted with dichloromethane [DCM]. Silica gel and celite were added thereto, and the resulting mixture was stirred for 5 minutes and then filtered. After the organic solvent was removed from the filtrate by using a vacuum rotary evaporator, the residue was column purified to obtain 1.1 g (yield 55%, HPLC purity 99.2%) of Compound 29.

NMR measurement value of Compound 29: $^1$H NMR (500 MHz, $CD_2Cl_2$) δ 7.70 (d, 2H), 7.68 (d, 2H), 7.57 (d, 4H), 7.48 (t, 8H), 7.41 (t, 4H), 7.34-7.26 (m, 8H), 7.23-7.10 (m, 26H), 6.76 (d, 4H), 6.64-6.58 (dd, 2H), 5.56 (d, 2H), 5.07 (d, 2H), 3.83-3.74 (m, 4H), 2.53-2.35 (m, 4H), 1.70-1.58 (m, 4H), 1.04-0.84 (m 4H)

Preparation Example 4. Synthesis of Compound 39

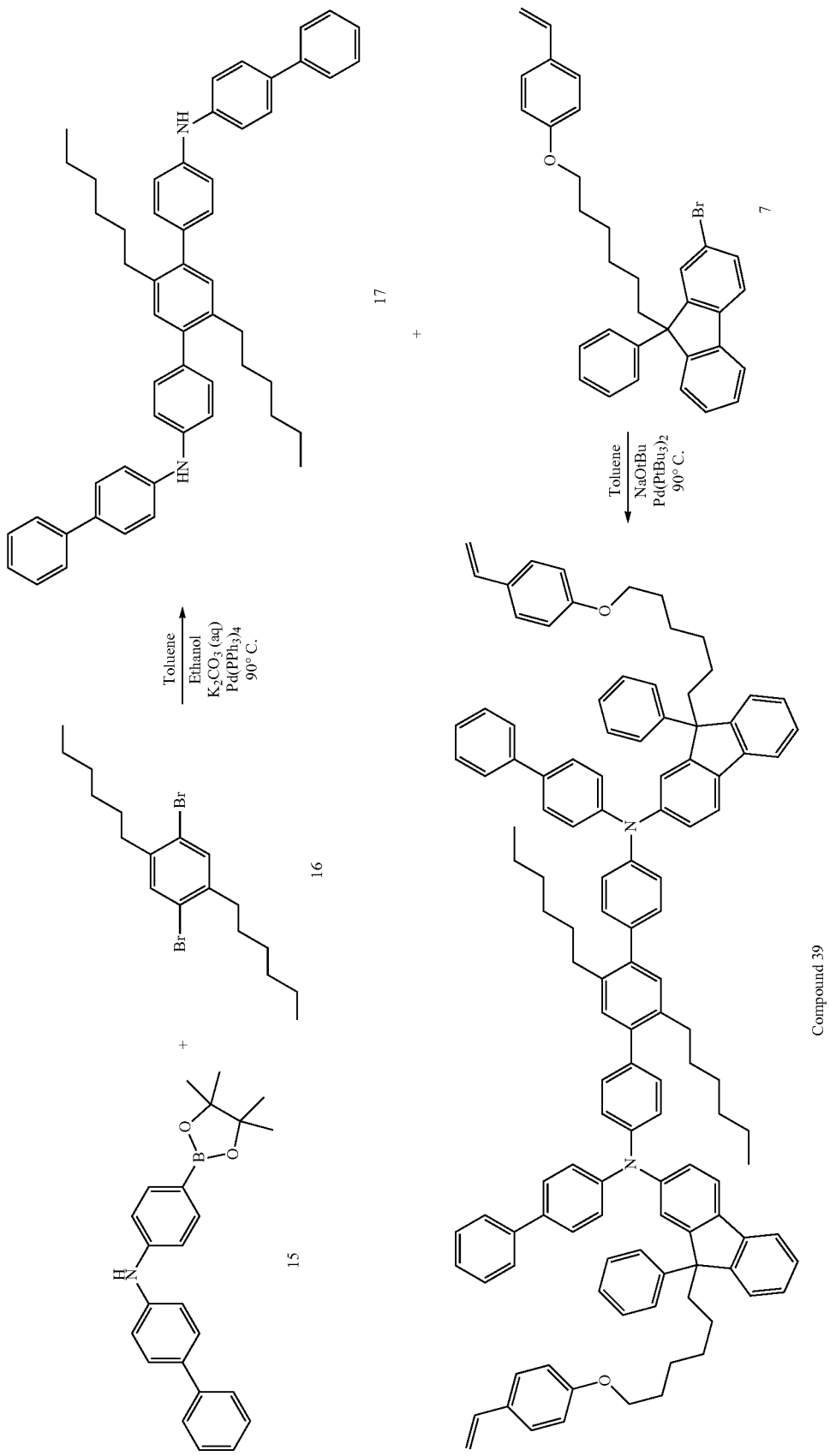

Synthesis of Intermediate 17 (N4,N4"-di([1,1-biphenyl]-4-yl)-2',5'-dihexyl-[1,1':4',1"-terphenyl]-4,4"-diamine): A toluene/EtOH/2 N K$_2$CO$_3$ (aq)(2v:1v:1v) solvent was put into a reaction flask containing N-(4-(4,4,5,5-tetramethyl-1,3,2-dioxaborolan-2-yl)phenyl)-[1,1'-biphenyl]-4-amine (15) (1.2 g, 3.3 mmol) and 1,4-dibromo-2,5-dihexylbenzene (16) (0.6 g, 1.5 mmol). The reaction flask was degassed using a vacuum pump. Pd(PPh$_3$)$_4$ (347 mg, 0.3 mmol) was put into the reaction flask, and the resulting mixture was stirred at 90° C. for a day. Ethanol was removed using a vacuum rotary evaporator, and the organic material was extracted with dichloromethane (DCM). After the organic layer was dried over MgSO$_4$, the organic layer was filtered and column purified to obtain 730 mg (yield 66%) of Intermediate 17.

Synthesis of Compound 39 (N4,N4"-di([1,1'-biphenyl]-4-yl)-2',5'-dihexyl-N4,N4"-bis(9-phenyl-9-(6-(4-vinylphenoxy)hexyl)-9H-fluoren-2-yl)-[1,1':4',1"-terphenyl]-4,4"-diamine): Intermediate 7 (1.13 g, 2.16 mmol), Intermediate 17 (720 mg, 0.98 mmol), and NaOtBu (470 mg, 4.9 mmol) were put into a 50-ml round flask, and 12 ml of anhydrous toluene was added thereto. After the round flask containing the reactant was put into an oil bath at 90° C. and the reactant was stirred for 1 hour, the oil bath was removed, and the product was diluted with dichloromethane [DCM]. Silica gel and celite were added thereto, and the resulting mixture was stirred for 5 minutes and then filtered. After the organic solvent was removed from the filtrate by using a vacuum rotary evaporator, the residue was column purified to obtain 986 mg (yield 62%, HPLC purity 99.3%) of Compound 39. APCI-Mass measurement value [M+H]$^+$ of Compound 39: 1618.0

Preparation Example 5. Synthesis of Compound 43

(1) Synthesis of Intermediate 19

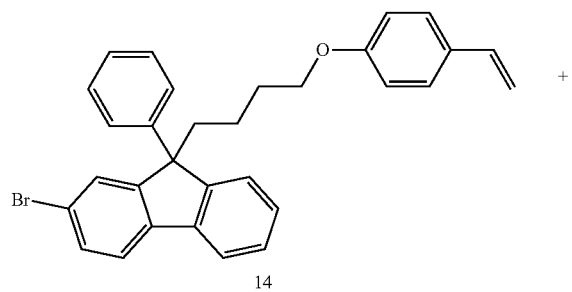

14

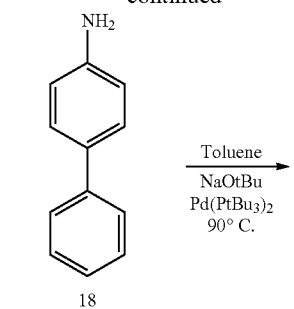

18

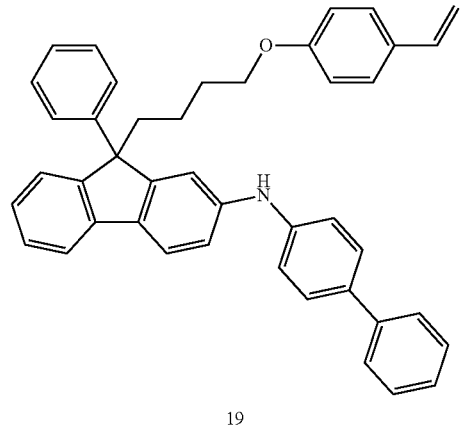

19

Synthesis of Intermediate 19 (N-([1,1'-biphenyl]-4-yl)-9-phenyl-9-(4-(4-vinylphenoxy)butyl)-9H-fluoren-2-amine): Toluene was put into a flask containing Intermediate 14 (3.0 g, 6.1 mmol), [1,1'-biphenyl]-4-amine (2.0 g, 11.8 mmol), and sodium tert-butoxide (1.73 g, 18.0 mmol). The flask containing the reactants was dipped into an oil bath at 90° C., and then Pd(PtBu$_3$)$_2$ (93 mg, 0.18 mmol) was added thereto, and the flask was rotated for 1 hour. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 2.93 g (yield 83%) of Intermediate 19.

(2) Synthesis of Compound 43

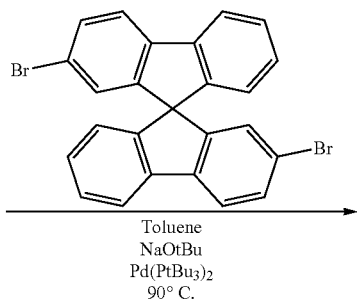

19

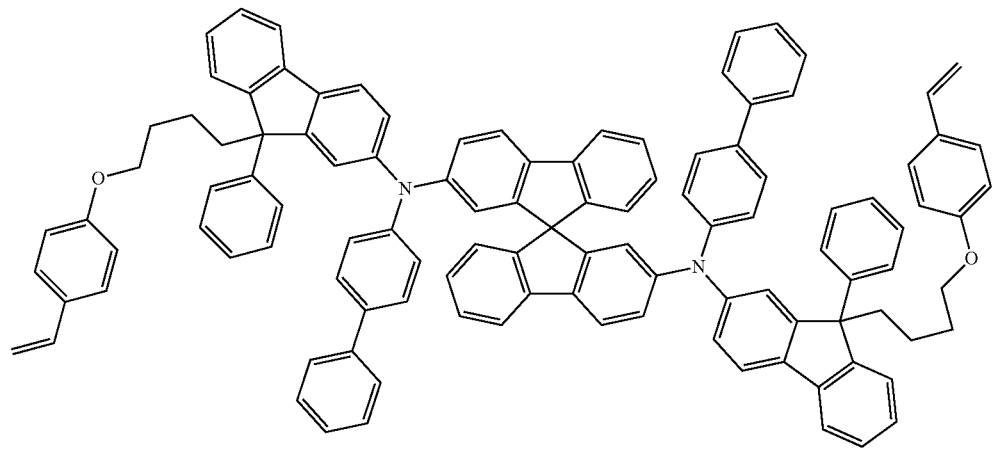

Compound 43

Synthesis of Compound 43: Toluene was put into a flask containing Intermediate 19 (1.28 g, 2.2 mmol), 2,2'-dibromo-9,9'-spirobi[fluorene] (474 mg, 1 mmol), and sodium tert-butoxide (1.34 g, 14.0 mmol), and the flask was bubbled with nitrogen. The flask containing the reactants was dipped into an oil bath at 90° C., and then Pd(PtBu$_3$)$_2$ (36 mg, 0.07 mmol) was added thereto, and the flask was rotated for 1 hour. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 810 mg (yield 57%, HPLC purity 98.7%) of Compound 43. APCI-Mass measurement value [M+H]$^+$ of Compound 43: 1479.8

Preparation Example 6. Synthesis of Comparative Compound A (1) Synthesis of Intermediate 22

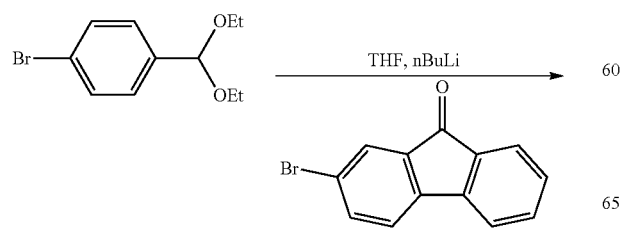

-continued

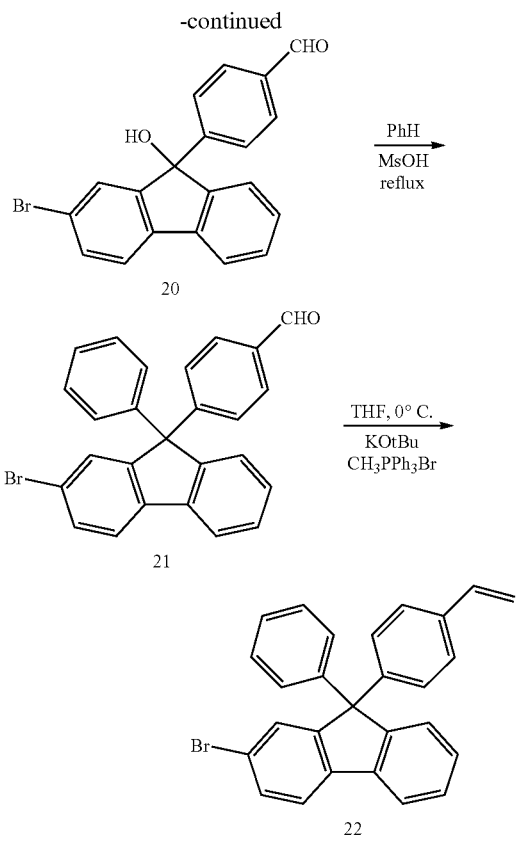

Synthesis of 4-(2-bromo-9-hydroxy-9H-fluoren-9-yl)benzaldehyde (20): 1-bromo-4-(diethyoxymethyl)benzene (13.2 ml, 64.9 mmol) was dissolved in tetrahydrofuran and the temperature was lowered to −78° C. nBuLi (2.5 M in hexane, 24 ml, 60 mmol) was added thereto, and the resulting mixture was stirred at −78° C. for 30 minutes. 2-bromo-9H-fluoren-9-one (10 g, 38.6 mmol) was added thereto at once and the resulting mixture was stirred overnight. The reaction was terminated with 1 N HCl (aq), followed by extraction with ethyl acetate. After the collected organic solution was dried over magnesium sulfate (MgSO$_4$) and filtered, the organic solvent was removed by a vacuum rotary evaporator. After the residue was column purified, the purified product was recrystallized (toluene/hexane) to obtain 13 g (yield 55%) g of Intermediate 20.

Synthesis of 4-(2-bromo-9-phenyl-9H-fluoren-9-yl)benzaldehyde (21): 140 ml of benzene was put into Intermediate 20 (4.5 g, 12.3 mmol), methane sulfonic acid (400 µl, 6.16 mmol) was added thereto, and then the resulting mixture was refluxed using a Dean-Stark apparatus. The acid was neutralized with saturated NaHCO$_3$ (aq), followed by column purification to obtain 2.73 g (yield 52%) of Intermediate 21.

Synthesis of 2-bromo-9-phenyl-9-(4-vinylphenyl)-9H-fluorene (22): Intermediate 21 (2.9 g, 6.82 mmol) and CH$_3$BrPPh$_3$ (4.89 g, 13.7 mmol) were added to tetrahydrofuran (THF), potassium tert-butoxide (1.553 g, 13.7 mmol) was added thereto at 0° C., and the resulting mixture was stirred for 1 hour. The reaction was stopped with water, and the product was extracted with ethyl acetate (EA). After magnesium sulfate (MgSO$_4$) was added to the collected organic solution and the resulting mixture was dried and filtered, the organic solvent was removed by a vacuum rotary evaporator. The residue was column purified to obtain 2.8 g (yield 97%) of Intermediate 22.

(2) Synthesis of Comparative Compound A

Synthesis of Comparative Compound A: Toluene was put into a flask containing Intermediate 22 (1.58 g, 3.74 mmol), N4,N4'-diphenyl-[1,1'-biphenyl]-4,4'-diamine (572 mg, 1.7 mmol), and sodium tert-butoxide (980 mg, 10.2 mmol), and the flask was bubbled with nitrogen. The flask containing the reactants was dipped into an oil bath at 90° C., and then Pd(PtBu$_3$)$_2$ (43 mg, 0.085 mmol) was added thereto, and the flask was rotated for 24 hours. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 950 mg (yield 55%) of Comparative Compound A.

NMR measurement value of Comparative Compound A:
$^1$H NMR (500 MHz, CD$_2$Cl$_2$) δ 7.71 (d, 2H), 7.65 (d, 2H), 7.42 (d, 4H), 7.35 (d, 4H), 7.27-7.20 (m, 18H), 7.17-7.13 (m, 4H), 7.11-7.06 (m, 14H), 7.03 (t, 2H), 6.70-6.64 (dd, 2H), 5.69 (d, 2H), 5.19 (d, 2H)

Preparation Example 7. Synthesis of Comparative Compound B (1) Synthesis of Intermediate 20

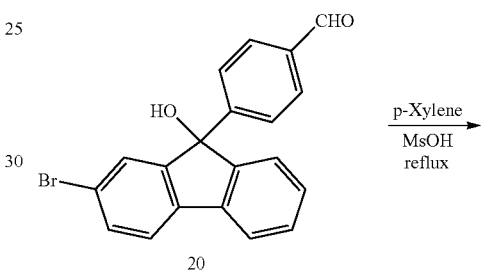

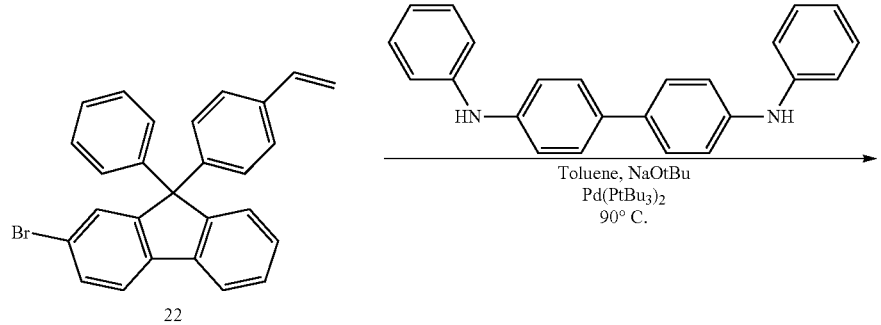

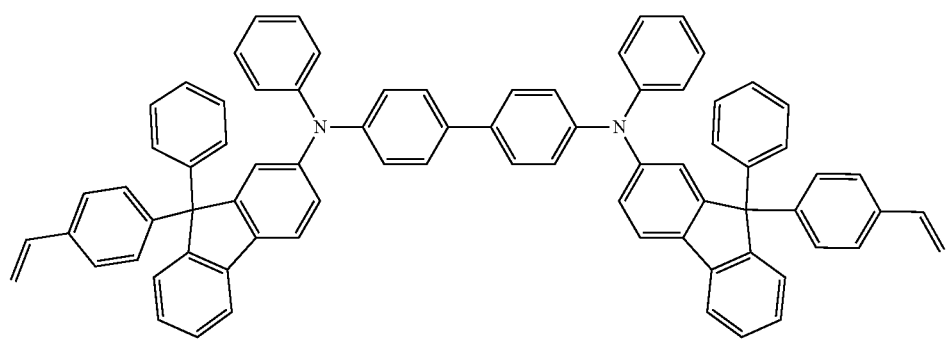

A

-continued

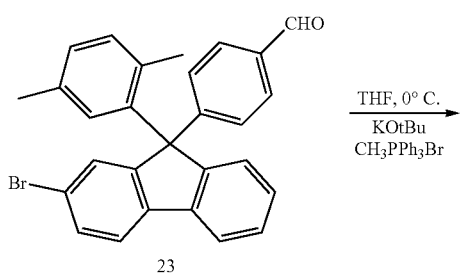

23

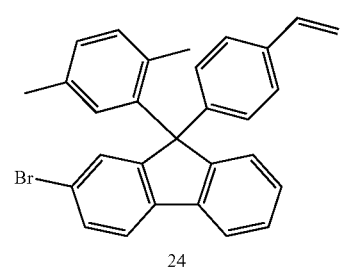

24

Synthesis of 4-(2-bromo-9-(2,5-dimethylphenyl)-9H-fluoren-9-yl)benzaldehyde (23): 140 ml of p-xylene was put into Intermediate 20 (5.11 g, 14 mmol), methane sulfonic acid (1.8 ml, 28 mmol) was added thereto, and then the resulting mixture was stirred at 70° C. for one day. The acid was neutralized with saturated NaHCO$_3$ (aq), followed by extraction with ethyl acetate. After the collected organic solution was dried over magnesium sulfate (MgSO$_4$) and filtered, the organic solvent was removed by a vacuum rotary evaporator. The residue was column purified to obtain 4.3 g (yield 68%) of Intermediate 23.

Synthesis of 2-bromo-9-(2,5-dimethylphenyl)-9-(4-vinylphenyl)-9H-fluorene (24): 100 ml of anhydrous tetrahydrofuran (THF) was added to CH$_3$BrPPh$_3$ (11.8 g, 33.19 mmol), potassium tert-butoxide (3.2 g, 28.44 mmol) was added thereto at 0° C., and the resulting mixture was stirred for 10 minutes. Intermediate 23 (4.3 g, 9.48 mmol) was dissolved in anhydrous tetrahydrofuran (THF)(20 ml, 10 ml, 10 ml), the resulting solution was added thereto, and 10 minutes later, the reaction was stopped with water, and the product was extracted with ethyl acetate. After the collected organic solution was dried over NaSO$_4$ and filtered, the organic solvent was removed by using a vacuum rotary evaporator. The residue was column purified to obtain 3.88 g (yield 91%) of Intermediate 24.

(2) Synthesis of Comparative Compound B

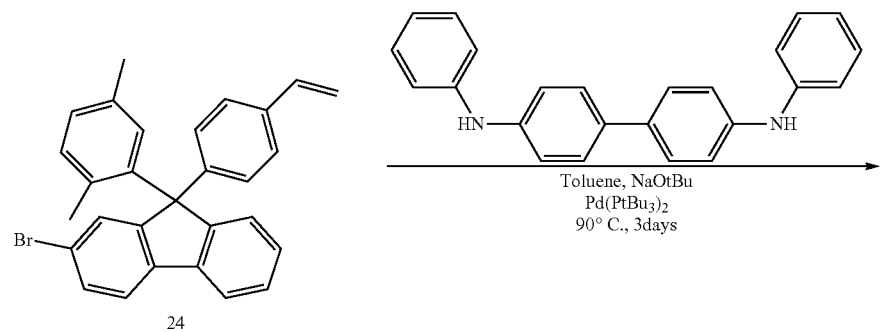

24

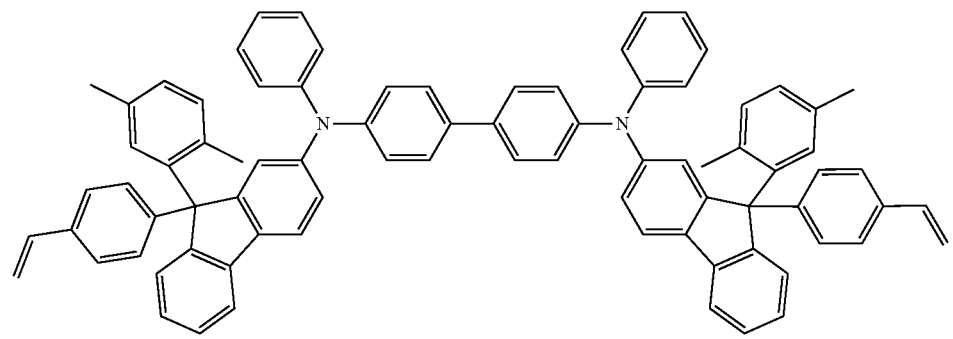

B

Synthesis of Comparative Compound B: Toluene was put into a flask containing Intermediate 24 (1.37 g, 3.03 mmol), N4,N4'-diphenyl-[1,1'-biphenyl]-4,4'-diamine (464 mg, 1.38 mmol), and sodium tert-butoxide (769 mg, 8.3 mmol), and the flask was bubbled with nitrogen. The flask containing the reactants was dipped into an oil bath at 90° C., and then Pd(PtBu$_3$)$_2$ (36 mg, 0.085 mmol) was added thereto, and the flask was rotated for 24 hours. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 500 mg (yield 34%) of Comparative Compound B.

NMR measurement value of Comparative Compound B: $^1$H NMR (500 MHz, CD$_2$Cl$_2$) δ 7.70 (d, 2H), 7.63 (d, 2H), 7.43 (d, 4H), 7.37 (t, 2H), 7.30-7.20 (m, 14H), 7.15-7.05 (m, 14H), 7.02 (t, 2H), 6.93 (s, 4H), 6.86 (s, 2H), 6.71-6.65 (dd, 2H), 5.70 (d, 2H), 5.20 (d, 2H), 2.15 (s, 6H), 1.57 (s, 6H)

Preparation Example 8. Synthesis of Comparative Compound C (1) Synthesis of Comparative Compound C

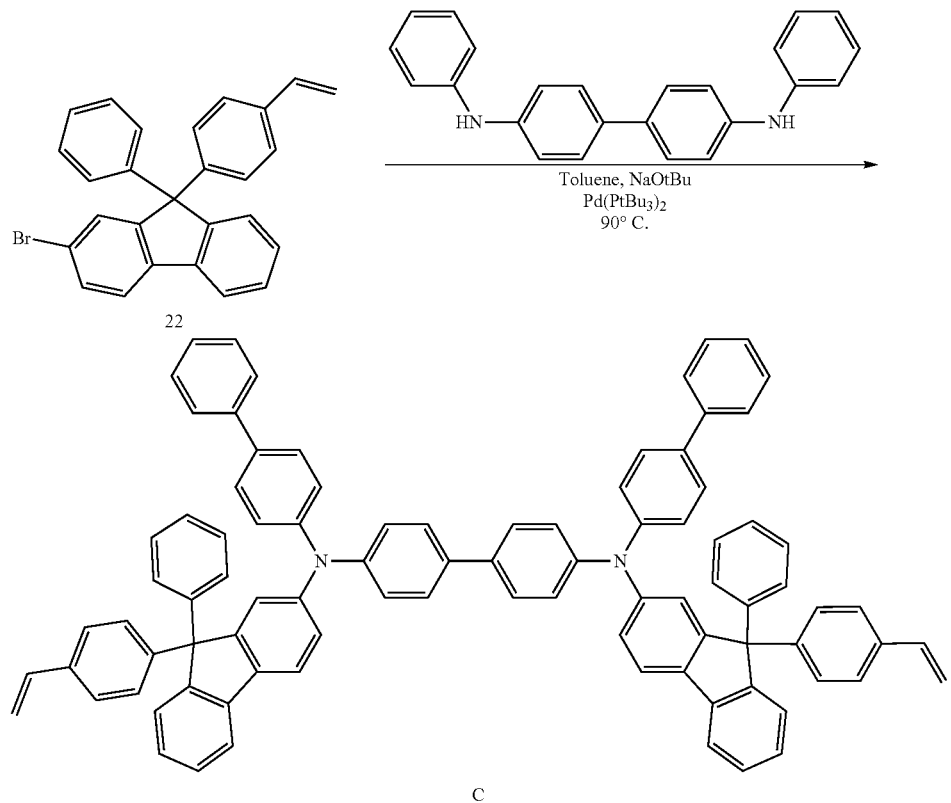

Synthesis of Comparative Compound C: Toluene was put into a flask containing Intermediate 22 (1.53 g, 3.61 mmol), N4,N4'-diphenyl-[1,1'-biphenyl]-4,4'-diamine (801 mg, 1.64 mmol), and sodium tert-butoxide (946 mg, 9.84 mmol), and the flask was bubbled with nitrogen. The flask containing the reactants was dipped into an oil bath at 90° C., and then Pd(PtBu$_3$)$_2$ (42 mg, 0.08 mmol) was added thereto, and the flask was rotated for 24 hours. The reaction was stopped by adding water thereto, the product was extracted with dichloromethane (DCM), and then the organic layer was dried over MgSO$_4$. After the organic solvent was removed using a vacuum rotary evaporator, the residue was column purified to obtain 1.06 mg (yield 55%, HPLC purity 99.4%) of Comparative Compound C.

NMR measurement value of Comparative Compound C: $^1$H NMR (500 MHz, CD$_2$Cl$_2$) δ 7.73 (d, 2H), 7.69 (d, 2H), 7.59 (d, 4H), 7.48 (t, 8H), 7.43 (t, 4H), 7.38-7.30 (m, 8H), 7.28-7.11 (m, 30H), 6.71-6.65 (dd, 2H), 5.69 (d, 2H), 5.20 (d, 2H)

EXPERIMENTAL EXAMPLE

Experimental Example 1. DSC Data Analysis

Starting from 30° C., the temperature was increased to 300° C. at 10° C. per minute, and then the temperature was maintained for 30 minutes. The temperature was decreased to 30° C. at 10° C. per minute again and then increased to 300° C. at 10° C. per minute again, thereby obtaining the DSC data. Tg, Tm, and the curing point, which were obtained, are shown in Table 1.

TABLE 1

| Compound | Endothermic peak (Tg, Tm) | Curing point (Tr max) | Remark |
| --- | --- | --- | --- |
| Compound 1 | 97° C. | 152° C. | Tr max is a |
| Comparative Compound A | 141 to 167° C. | 222° C. | point where the heat |
| Comparative Compound B | 127° C. | 210° C. | generation becomes a |

TABLE 1-continued

| Compound | Endothermic peak (Tg, Tm) | Curing point (Tr max) | Remark |
|---|---|---|---|
| Comparative Compound C | 134° C., 176° C. | 234° C. | maximum on DSC. |

In comparison of Comparative Compounds A and B, it was observed that Tg, Tm, and Trmax were changed by an aryl group directly linked to the 9H position of fluorene. It could be seen that when a xylyl group larger than a phenyl group is directly attached to the 9H position, Tg and Tm values, which may affect the mobility of molecule, were lowered, and the curing point was also lowered by 10° C. or more.

In comparison of Compound 1 and Comparative Compound C, it can be seen that Compound 1 has a much lower melting point and a much lower curing point than Comparative Compound C. Due to the effect of a fluorene group which became large in size, which are affected by an alkyl group used as a spacer, the interaction between molecules of these fluorene derivatives was reduced, and the creation of an appropriate space between a curing group and the fluorene could reduce a steric hindrance around the curing group, thereby inducing an intrinsic curing point of the curing group.

FIGS. 2 to 5 are graphs illustrating the DSC measurement results.

Experimental Example 2. Measurement of Thin Film Retention Rate

Thin films were formed by spin-coating 2 wt % toluene solutions of Compound 1 and Comparative Compound A onto glass. In a nitrogen atmosphere, the thin film formed of Compound 1 and the thin film formed of Comparative Compound A were heat-treated at 200° C. and 220° C., respectively, for 30 minutes, and UV absorbance of each thin film was measured. Again, the thin films were dipped into toluene and cyclohexanone (CHON) for 10 minutes and dried, and then UV was measured. A thin film retention rate was measured by comparing the sizes of the maximum peaks of UV absorbance before and after dipping the thin films into toluene and cyclohexanone (CHON).

In the case of Comparative Compound A having a curing group directly attached to fluorene, the thin film was not retained (FIG. 7, thin film retention rate 12% (toluene) and 3 wt % (cyclohexanone)), but Compound 1 having an appropriate space between the fluorene monomer (fluorene moiety) and the curing group had excellent resistance to the solvent (FIG. 6, thin film retention rate 100% (toluene, cyclohexanone)). It can be seen that the reduction in steric hindrance around the curing group and the increase in mobility of the curing group itself are helpful for the curing reaction.

FIG. 6 is a view illustrating a result of a film retention rate experiment of Compound 1.

FIG. 7 is a view illustrating a result of a film retention rate experiment of Comparative Compound A.

Experimental Example 3. Device Example

Preparation of ITO Substrate

A glass substrate thinly coated with indium tin oxide (ITO) to have a thickness of 1,500 Å was put into distilled water in which a detergent was dissolved, and ultrasonically washed. In this case, a product manufactured by Fischer Co., was used as the detergent, and distilled water, which had been filtered twice with a filter manufactured by Millipore Co., was used as the distilled water. After the ITO was washed for 30 minutes, ultrasonic washing was conducted twice repeatedly using distilled water for 10 minutes.

After the washing with distilled water was completed, the substrate was ultrasonically washed with isopropyl alcohol and acetone solvents, and dried, and then the substrate was cleaned for 5 minutes, and the substrate was transported to a glovebox.

Device Example 1

A 1.5 wt % toluene ink of HT-1:TB (8:2) was spin-coated (4,000 rpm) onto a surface of a transparent ITO electrode, and the electrode was subjected to a heat treatment (curing) at 230° C. for 30 minutes, thereby forming a hole injection layer to have a thickness of 30 nm. A 2 wt % toluene ink of Compound 1 was spin-coated (3,000 rpm) onto the hole injection layer formed above and the electrode was subjected to a heat treatment (curing) at 200° C. for 30 minutes, thereby forming a hole transport layer to have a thickness of 40 nm. A 1 wt % toluene ink of EM-1 was used and spin-coated (3,000 rpm) onto the hole transport layer formed, and the electrode was subjected to a heat treatment, thereby film-forming a light emitting layer to have a thickness of 20 nm. Thereafter, the electrode was transported to a vacuum deposition apparatus, and then ET-1 was vacuum-deposited on the light emitting layer to have a thickness of 35 nm, thereby forming an electron injection and transport layer. LiF and aluminum were sequentially deposited on the electron injection and transport layer to have a thickness of 1 nm and 100 nm, respectively, thereby forming a cathode.

In the aforementioned procedure, the deposition rate of the organic material was maintained at 0.4 to 0.7 Å/sec, the deposition rates of lithium fluoride and aluminum of the cathode were maintained at 0.3 Å/sec and at 2 Å/sec, respectively, and the degree of vacuum during the deposition was maintained at $2 \times 10^{-7}$ to $5 \times 10^{-6}$ torr. The following compound EM-1 has a Mw of 20,000 g/mol or more.

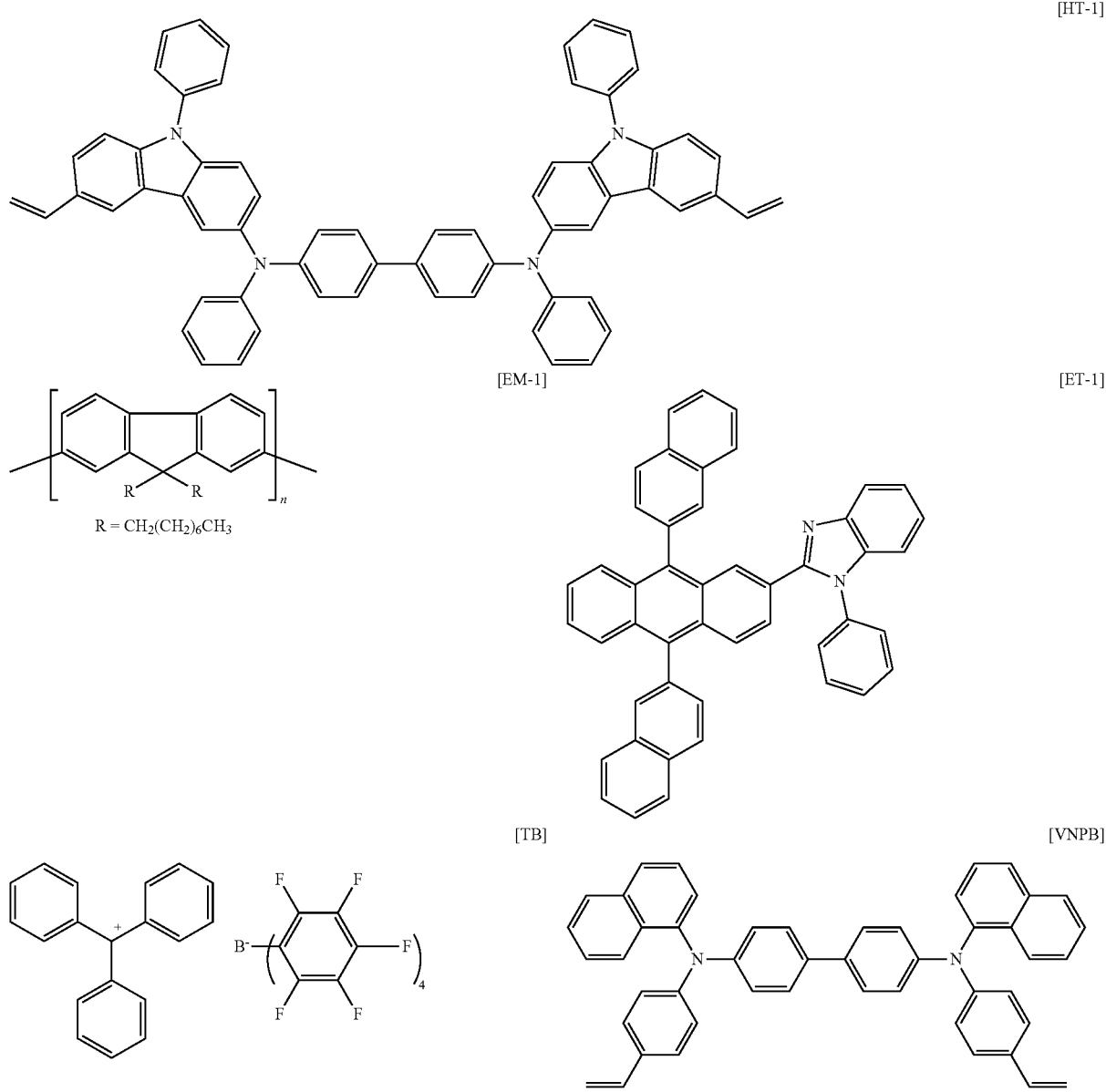

Device Example 2

An organic light emitting device was manufactured in the same manner as in Device Example 1, except that a 1.5 wt % toluene ink of Compound 1:TB (8:2) was used instead of a 1.5 wt % toluene ink of HT-1:TB (8:2) during the film formation of the hole injection layer in the manufacturing process of Device Example 1.

Device Example 3

An organic light emitting device was manufactured in the same manner as in Device Example 1, except that a 2 wt % toluene ink of Compound 29 was used instead of a 2 wt % toluene ink of Compound 1 during the film formation of the hole transport layer in the manufacturing process of Device Example 1.

Device Example 4

An organic light emitting device was manufactured in the same manner as in Device Example 1, except that a 2 wt % toluene ink of Compound 39 was used instead of a 2 wt % toluene ink of Compound 1 during the film formation of the hole transport layer in the manufacturing process of Device Example 1.

Device Example 5

An organic light emitting device was manufactured in the same manner as in Device Example 1, except that a 2 wt % toluene ink of Compound 43 was used instead of a 2 wt % toluene ink of Compound 1 during the film formation of the hole transport layer in the manufacturing process of Device Example 1.

Comparative Device Example

An organic light emitting device was manufactured in the same manner as in Device Example 1, except that a 2 wt % toluene ink of VNPB was used instead of a 2 wt % toluene ink of Compound 1 during the film formation of the hole transport layer in the manufacturing process of Device Example 1.

The driving voltage, the current density, the quantum efficiency (QE), and the luminance value at a current density of 10 mA/cm² in each of the devices manufactured by using the materials according to the present invention and the comparative material are shown in the following Table 2. T95 means time taken to be reduced from the initial luminance (500 nit) to 95% of the initial luminance at a current density of 10 mA/cm².

TABLE 2

|  | Volt | J(mA/cm²) | QE (%) | Cd/m² | T95@ 500 nit |
|---|---|---|---|---|---|
| Device Example 1 | 7.6 | 10.0 | 0.5 | 53 | 3.5 |
| Device Example 2 | 6.6 | 10.0 | 0.7 | 71 | 4.1 |
| Device Example 3 | 7.3 | 10.0 | 0.6 | 55 | 3.9 |
| Device Example 4 | 7.8 | 10.0 | 0.6 | 57 | 3.4 |
| Device Example 5 | 7.5 | 10.0 | 0.6 | 56 | 4.0 |
| Comparative Device Example | 8.0 | 10.0 | 0.2 | 22 | 2.3 |

As shown in Table 2, it can be confirmed that Device Examples 1 to 5 comprising the fluorene-based compound according to the present invention has good current efficiency and excellent service life characteristics as compared to the Comparative Device Example.

The invention claimed is:
1. A fluorene-based compound represented by the following Formula 1:

[Formula 1]

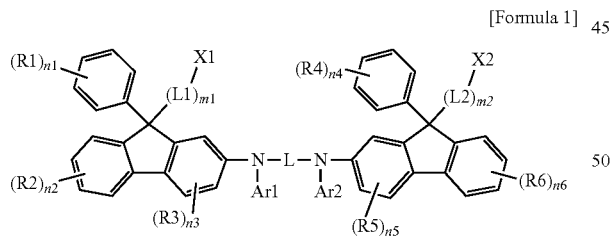

in Formula 1,
L1 and L2 are the same as or different from each other, and are each independently a substituted or unsubstituted alkylene group; a substituted or unsubstituted cycloalkylene group; or a substituted or unsubstituted heteroarylene group,
L is a substituted or unsubstituted arylene group; or a substituted or unsubstituted heteroarylene group,
R1 to R6 are the same as or different from each other, and are each independently hydrogen; deuterium; a halogen group; a substituted or unsubstituted alkyl group; a substituted or unsubstituted alkoxy group; a substituted or unsubstituted aryl group; or a substituted or unsubstituted heteroaryl group, and R1 to R6 are each optionally connected to each other to form a substituted or unsubstituted hydrocarbon ring,
Ar1 and Ar2 are the same as or different from each other, and are each independently a substituted or unsubstituted aryl group; or a substituted or unsubstituted heteroaryl group,
X1 and X2 are the same as or different from each other, and are each independently a photocurable group or a thermosetting group,
n1 and n4 are each independently an integer of 0 to 5,
n2 and n6 are each independently an integer of 0 to 4,
n3 and n5 are each independently an integer of 0 to 3,
when n1 to n6 are each 2 or more, R1s to R6s are each independently the same as or different from each other,
m1 and m2 are each independently an integer of 2 to 12, and
when m1 and m2 are each 2 or more, L1s and L2s are each independently the same as or different from each other,
wherein the photocurable group or the thermosetting group in the definitions of X1 and X2 is any one of the following structures:

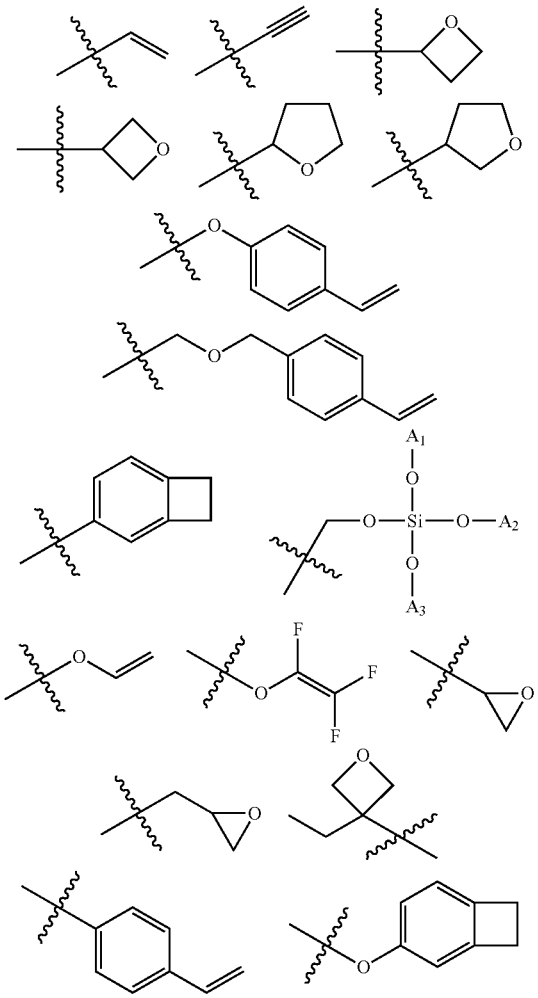

in the structures,
A1 to A3 are the same as or different from each other, and are each independently a substituted or unsubstituted alkyl group having 1 to 6 carbon atoms.

2. The fluorene-based compound of claim 1, wherein L is a substituted or unsubstituted arylene group having 6 to 30 carbon atoms; or a substituted or unsubstituted heteroarylene group having 2 to 30 carbon atoms.

3. The fluorene-based compound of claim 1, wherein Ar1 and Ar2 are the same as or different from each other, and are each independently a substituted or unsubstituted aryl group having 6 to 30 carbon atoms; or a substituted or unsubstituted heteroarylene group having 2 to 30 carbon atoms.

4. The fluorene-based compound of claim 1, wherein Formula 1 is represented by any one of the following Compounds 1 to 48:

Compound 1

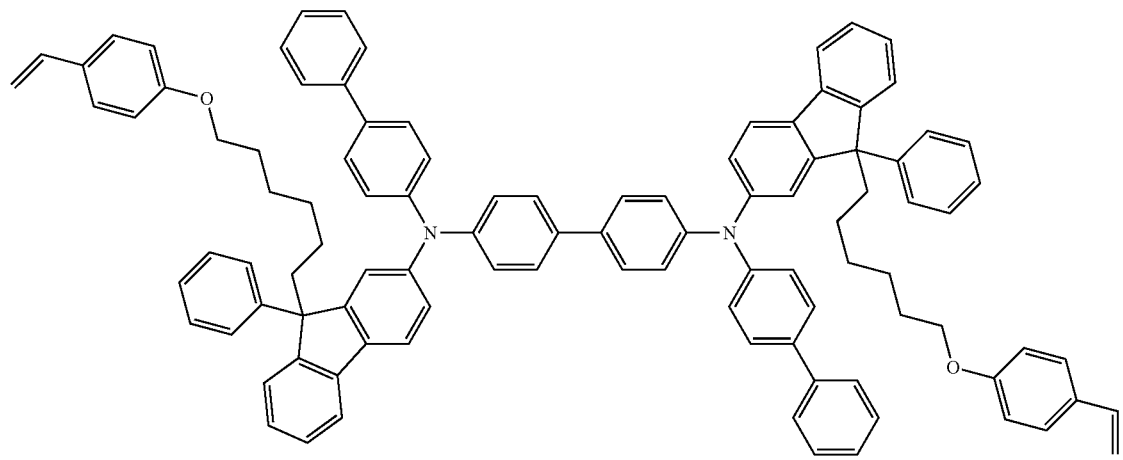

Compound 2

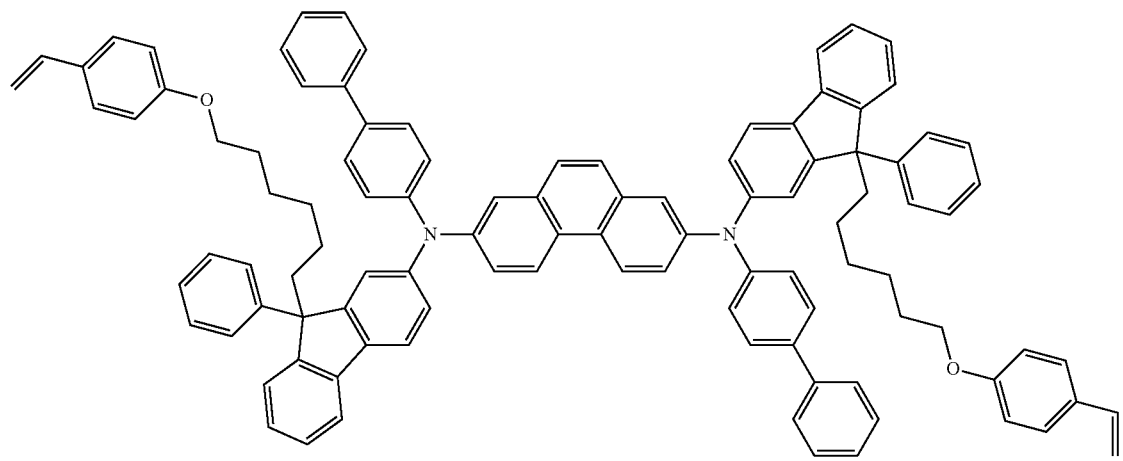

Compound 3

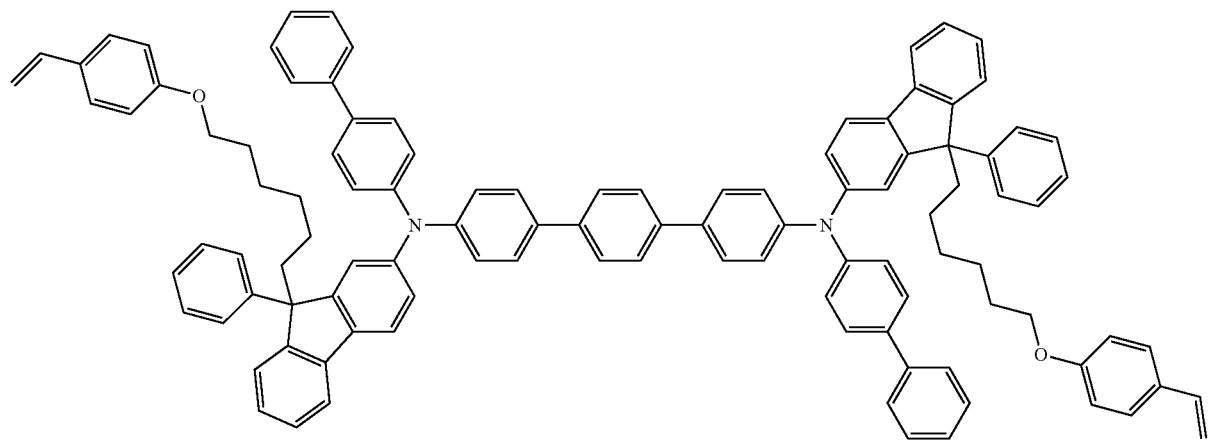

-continued
Compound 4
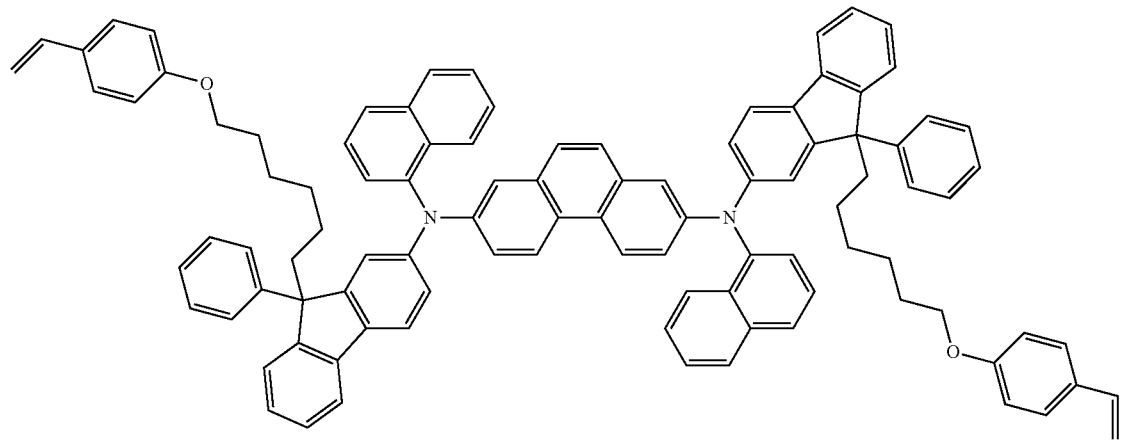
Compound 5
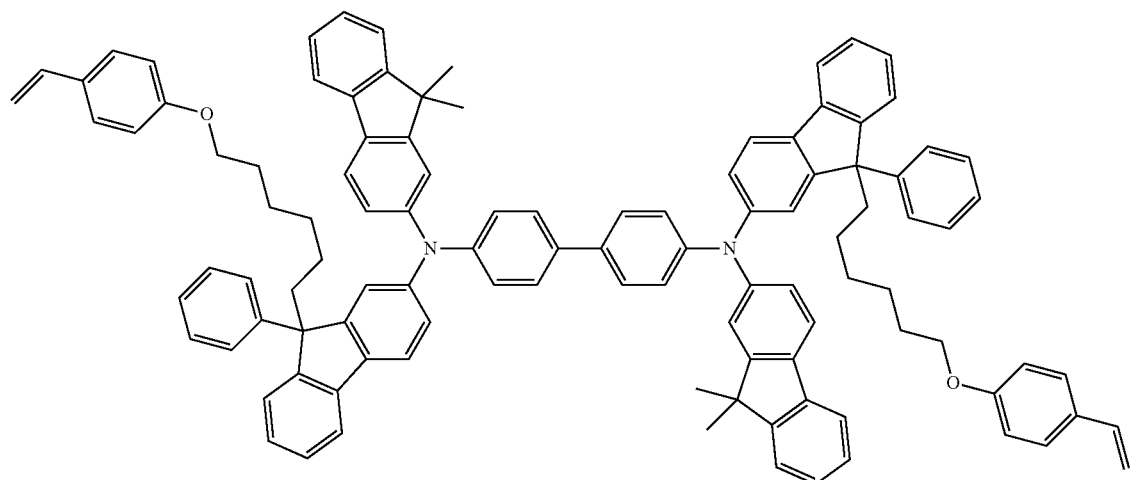
Compound 6
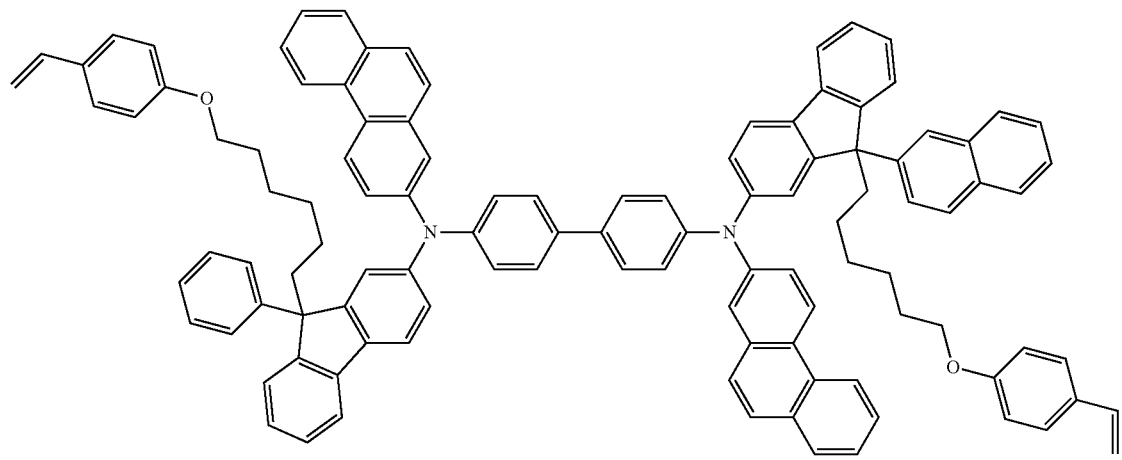

Compound 7
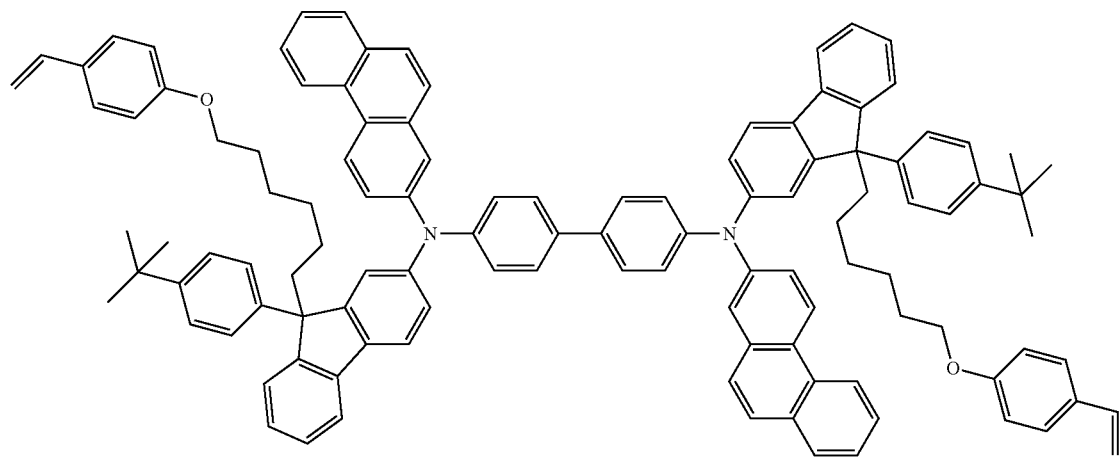
Compound 8
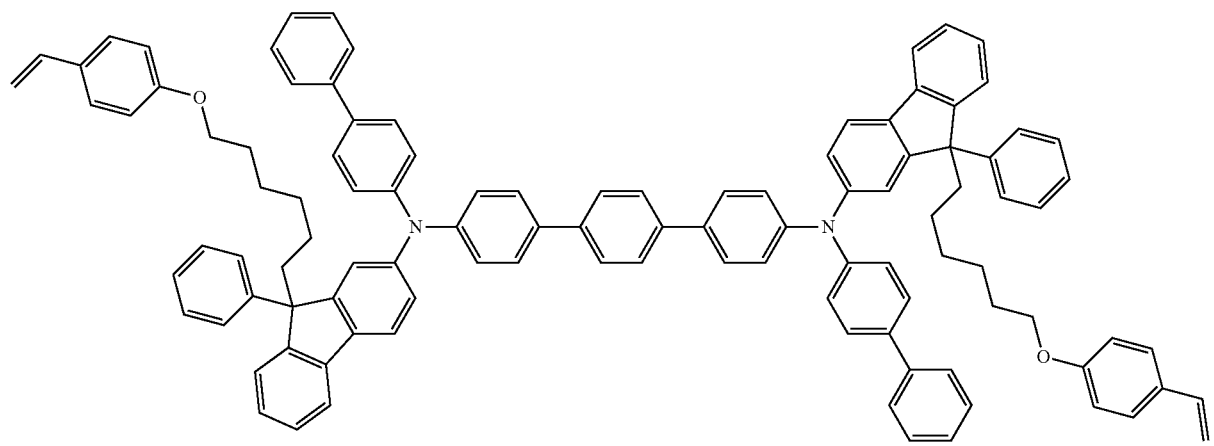
Compound 9
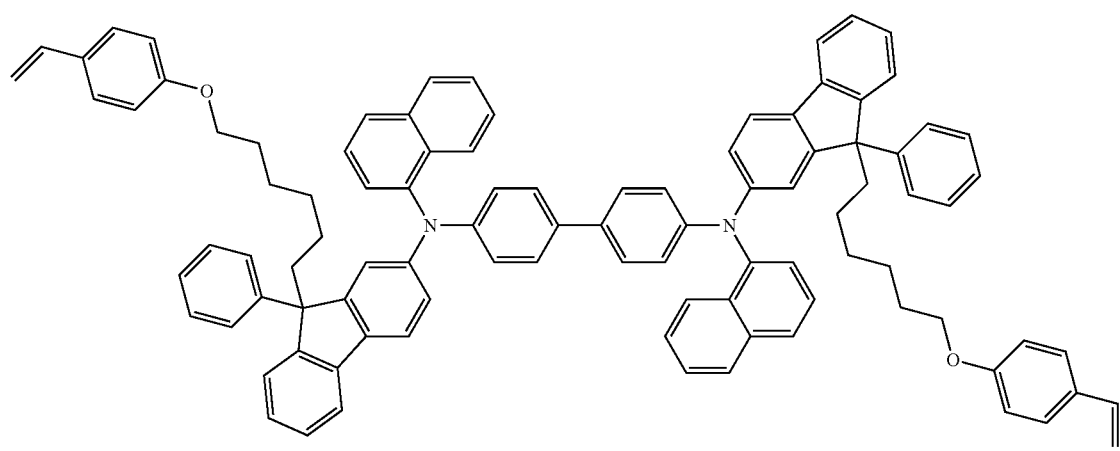

-continued
Compound 10
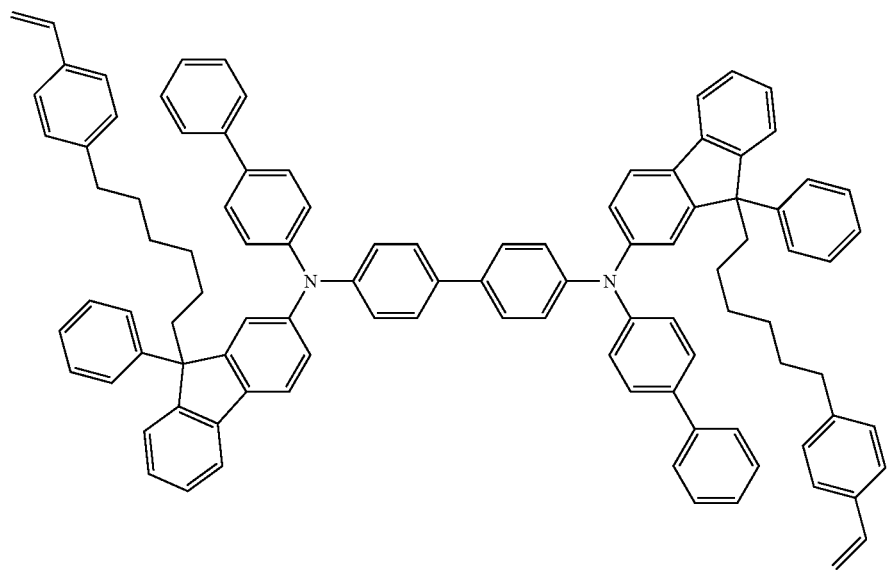
Compound 11
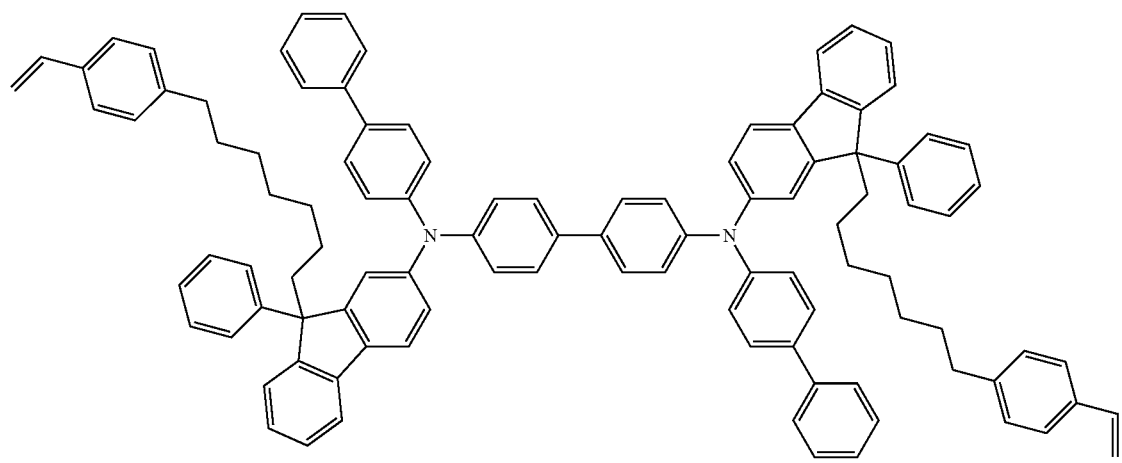
Compound 12
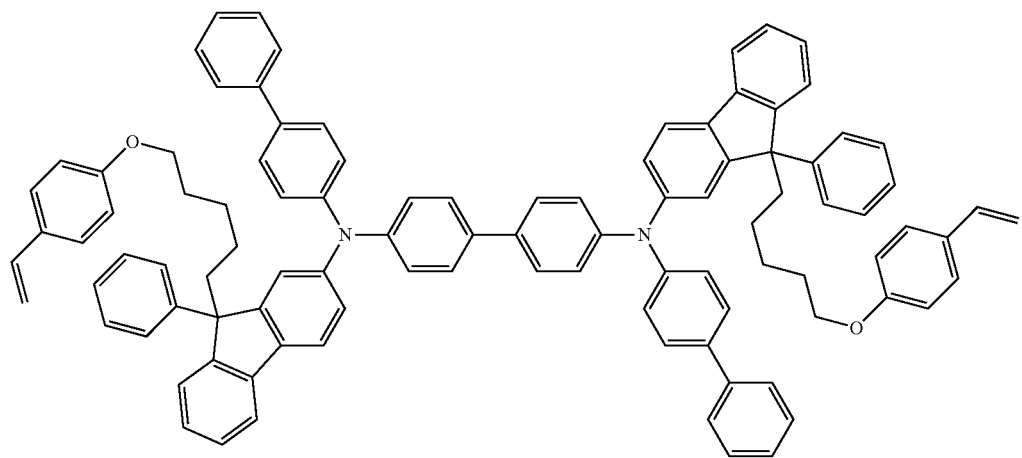

-continued
Compound 13
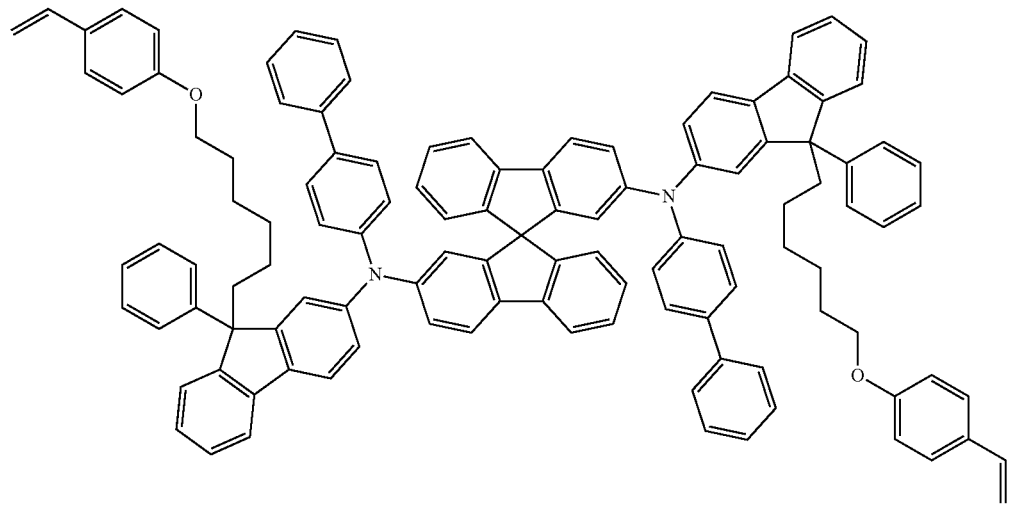
Compound 14
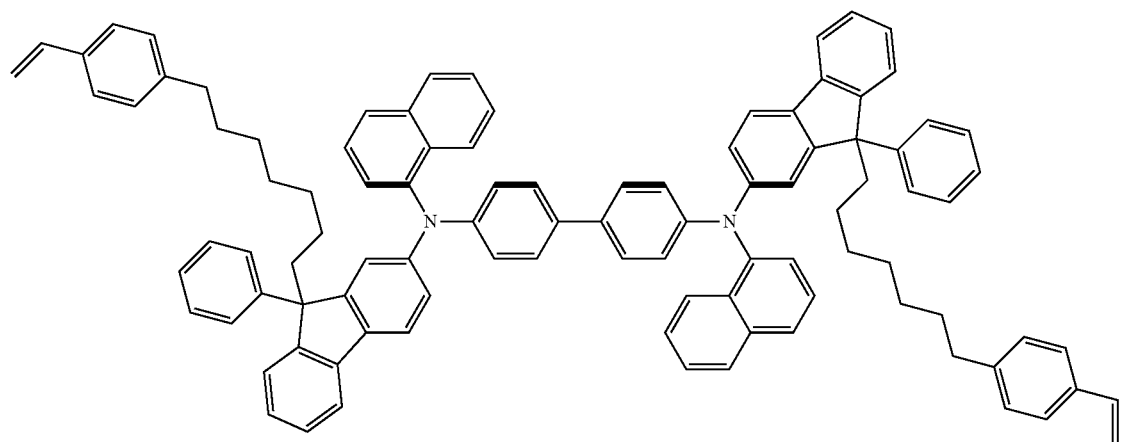
Compound 15
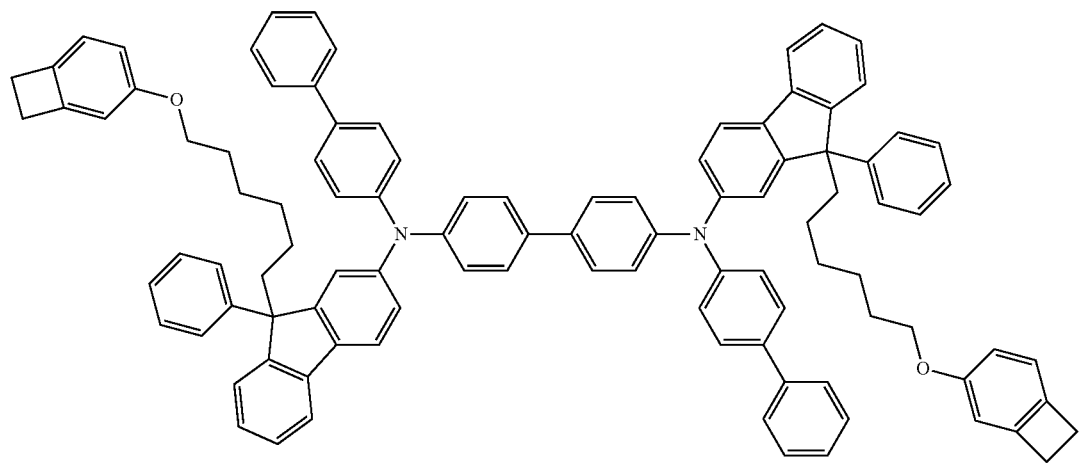

-continued
Compound 16
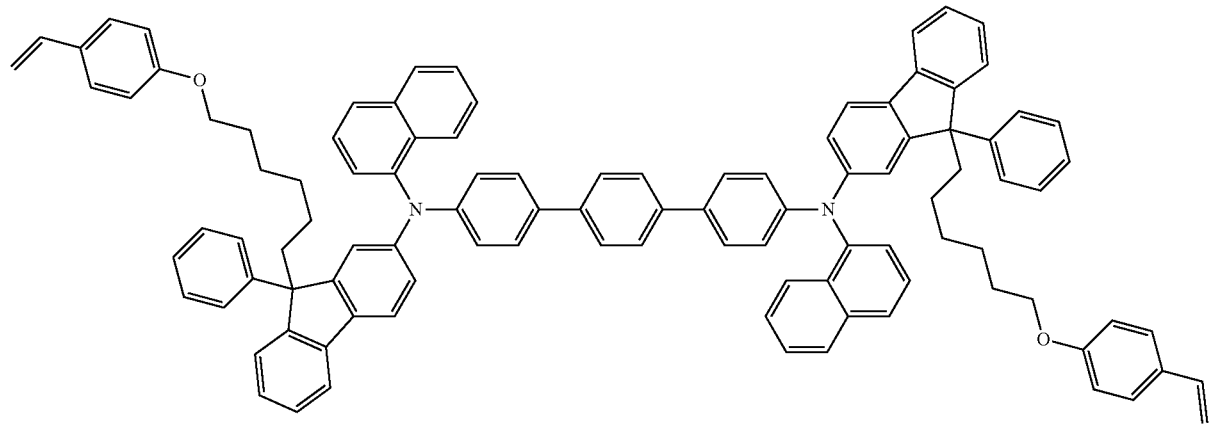
Compound 17
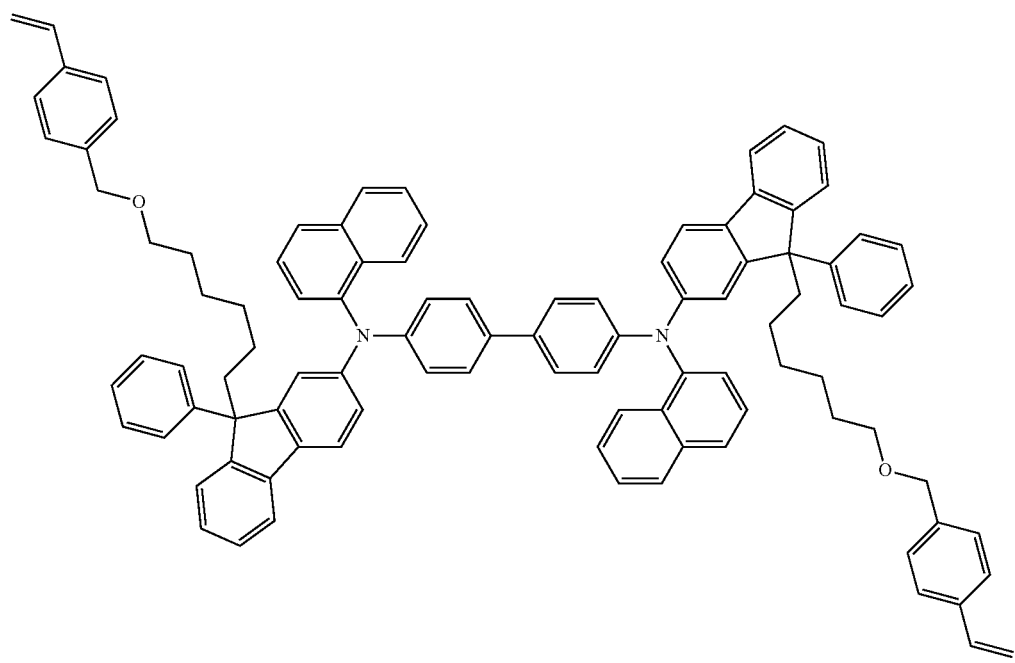
Compound 18
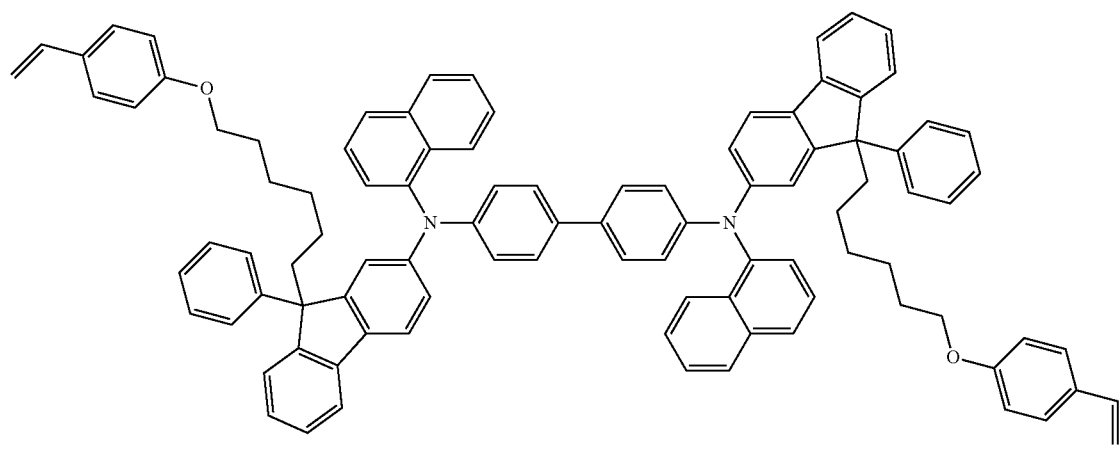

-continued
Compound 19
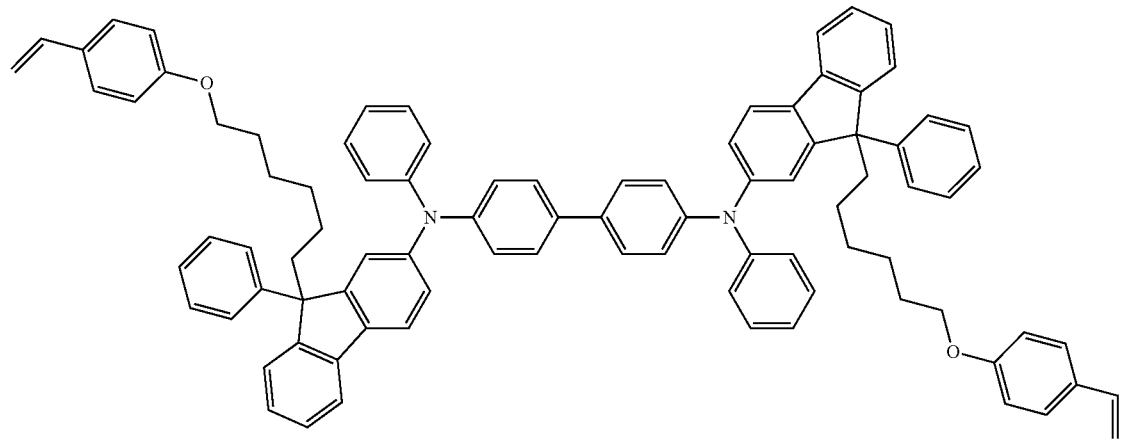
Compound 20
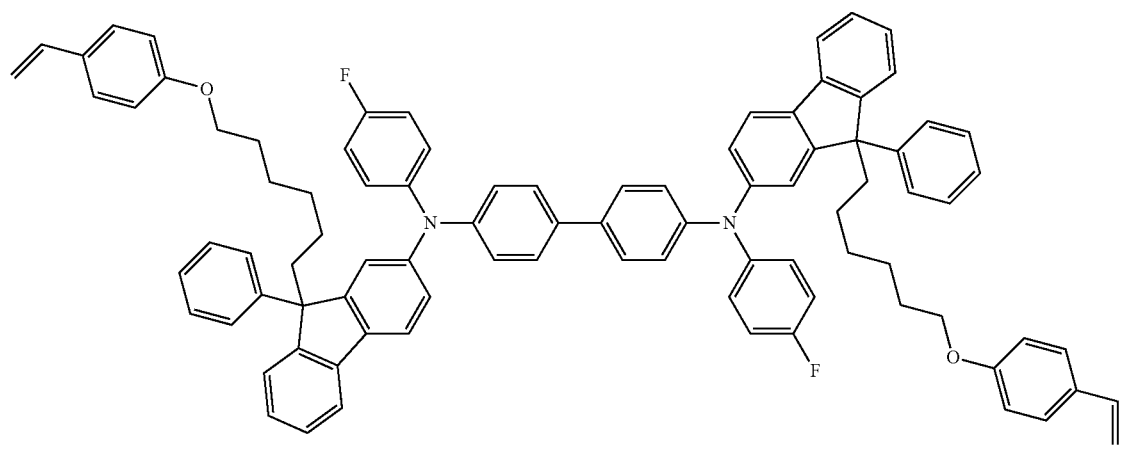
Compound 21
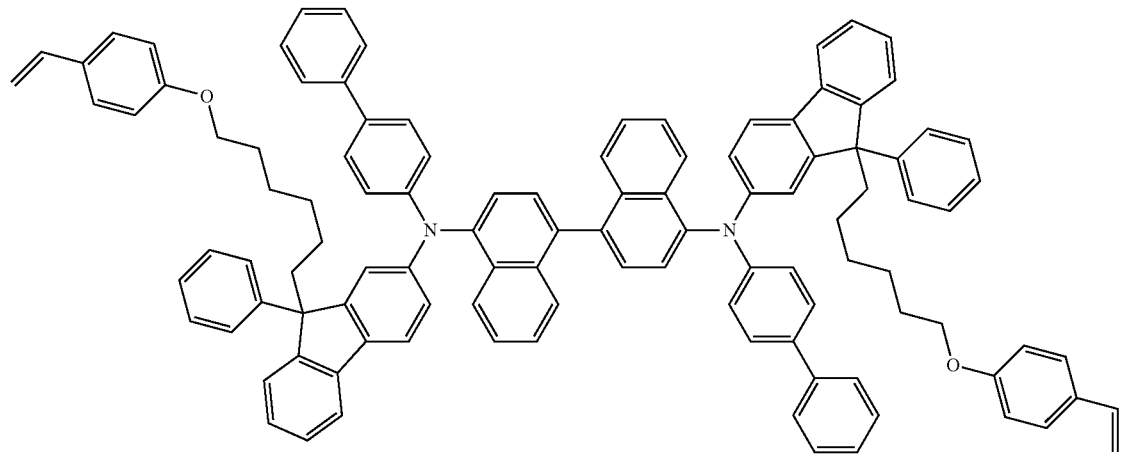

Compound 22
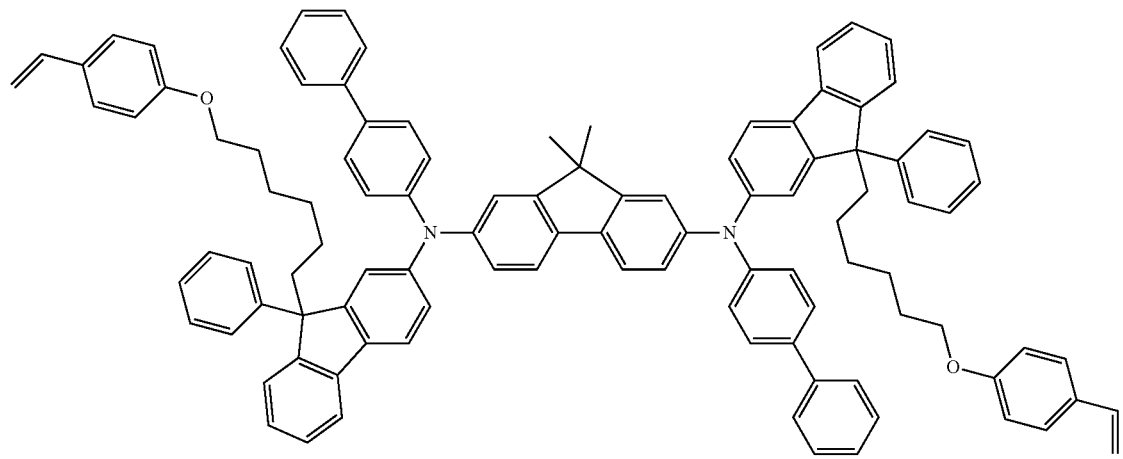
Compound 23
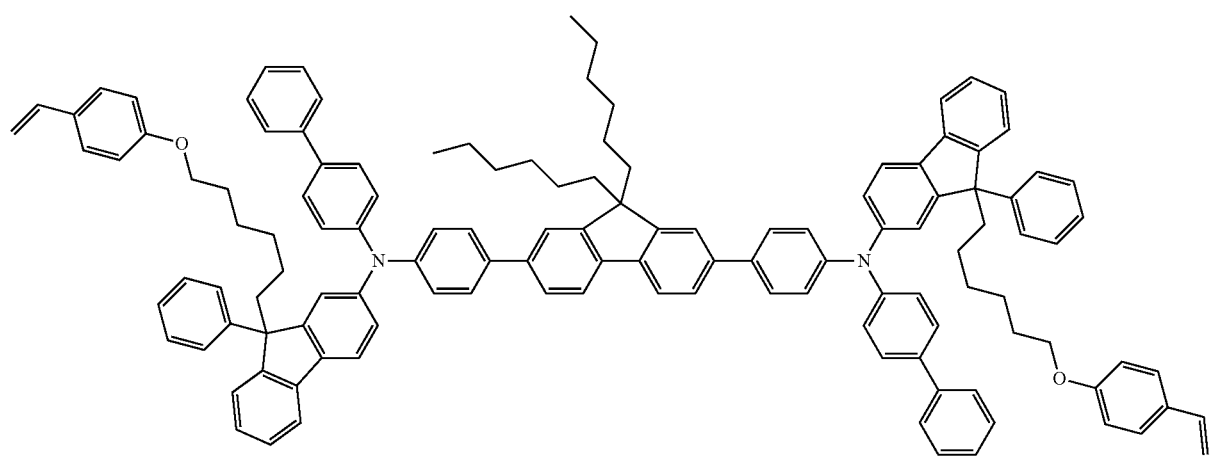
Compound 24
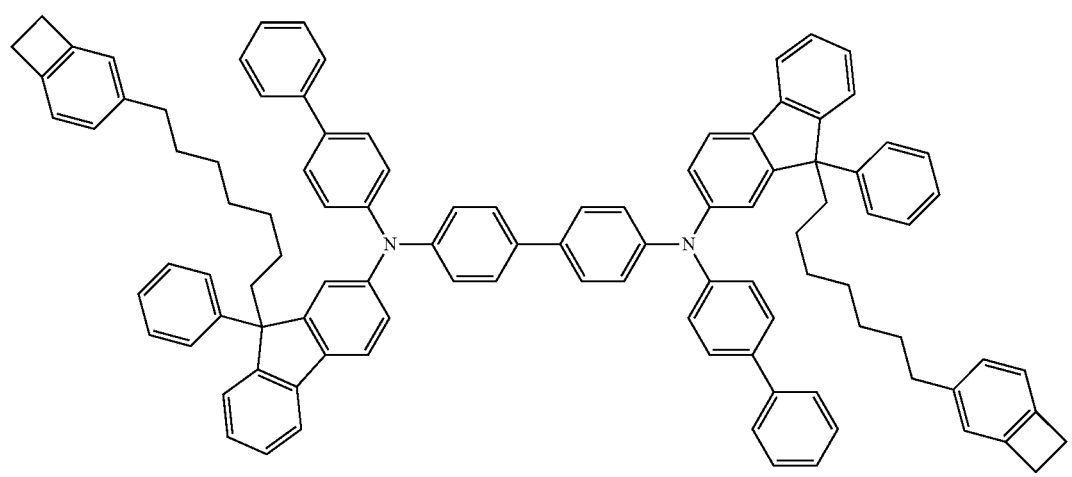

Compound 25
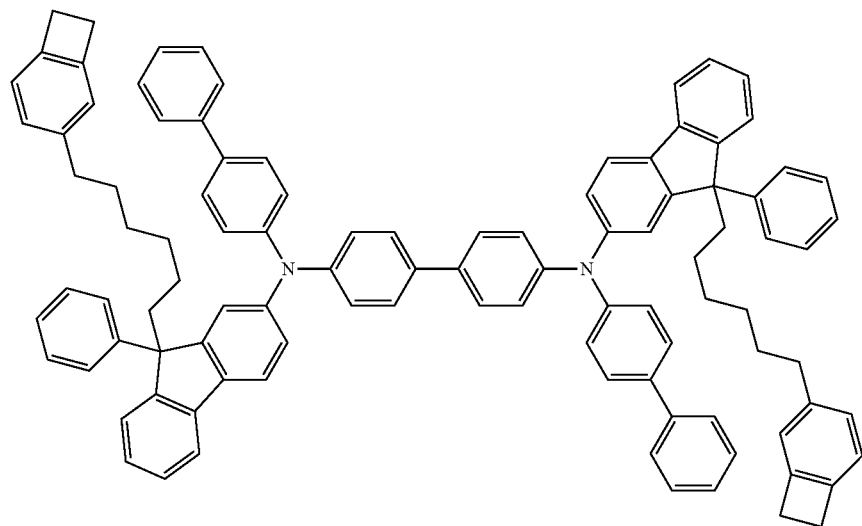
Compound 26
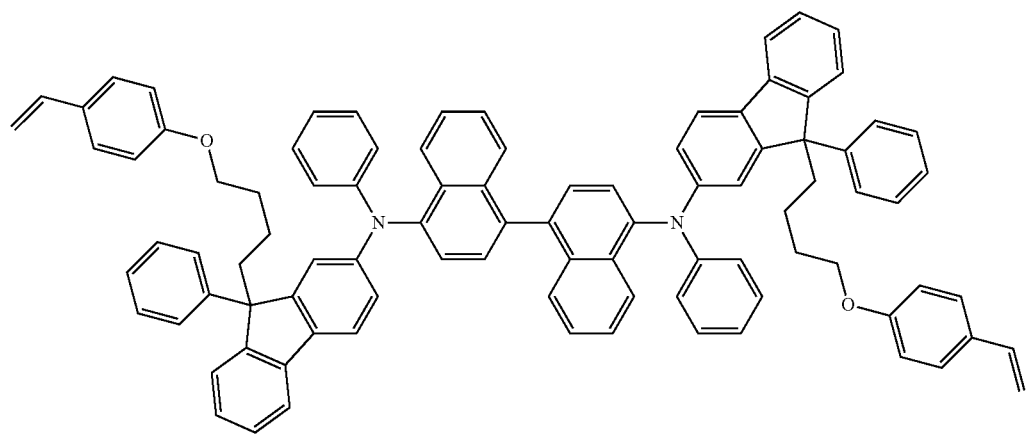
Compound 27
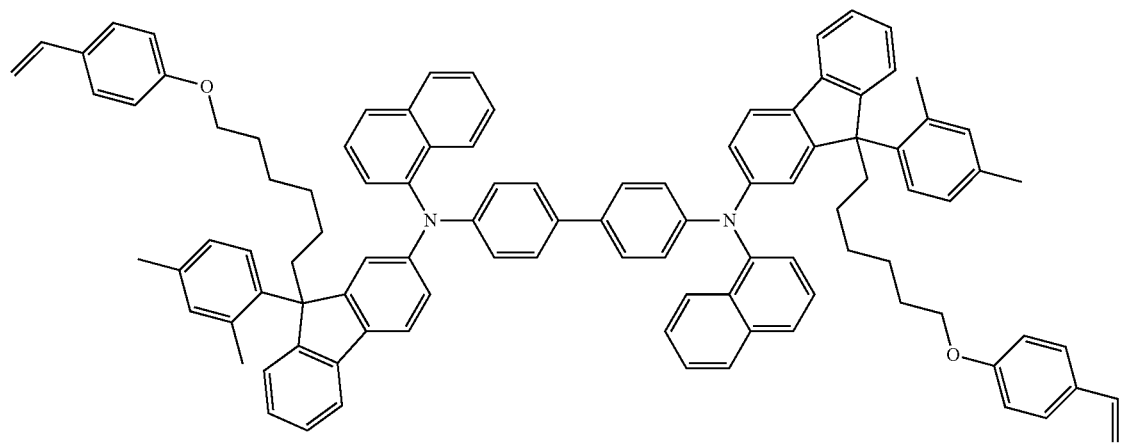

-continued
Compound 28
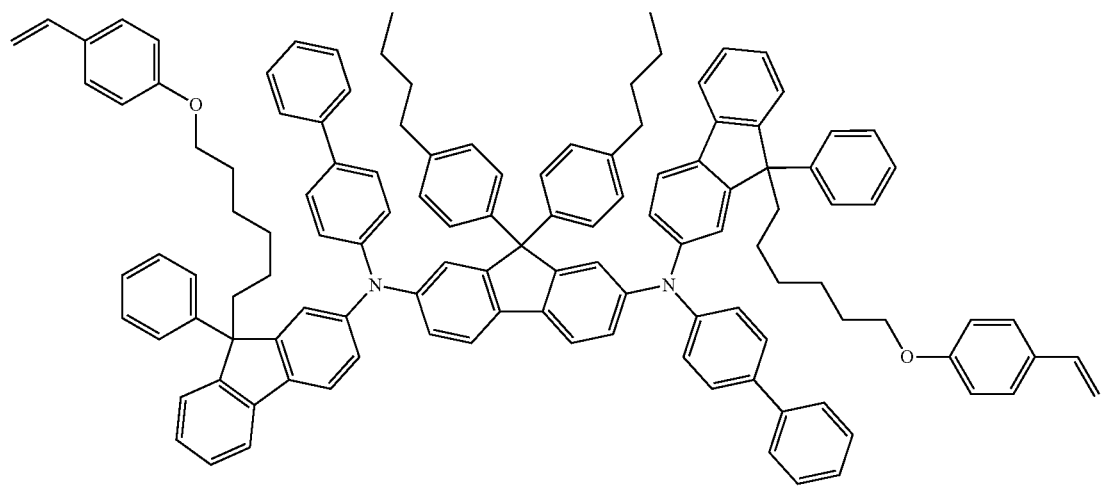
Compound 29
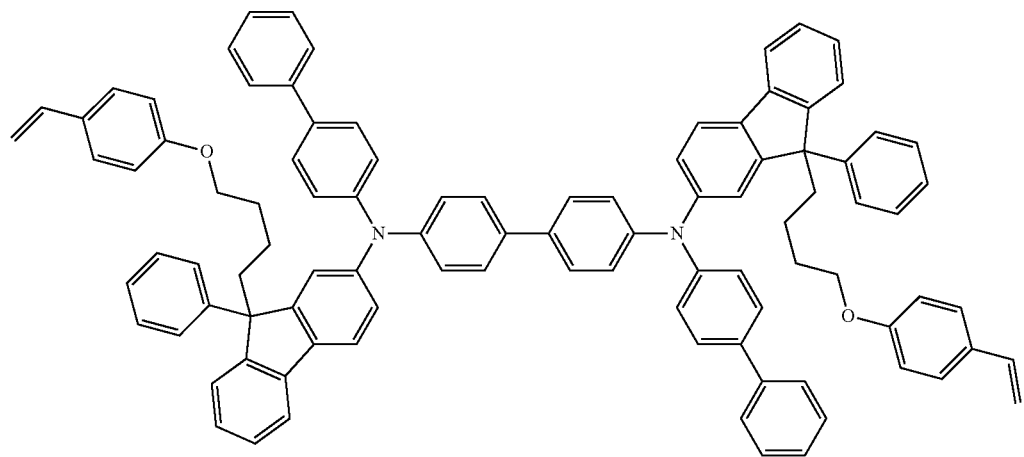
Compound 30
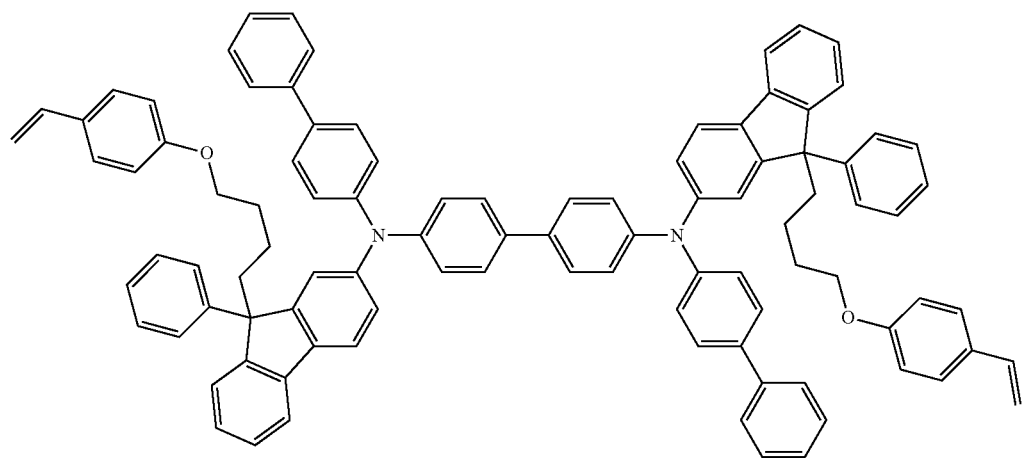

Compound 31
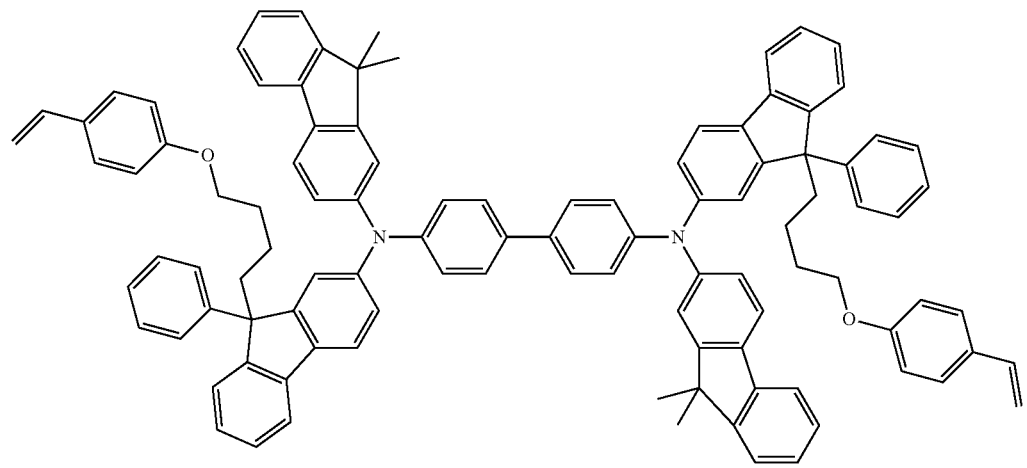
Compound 32
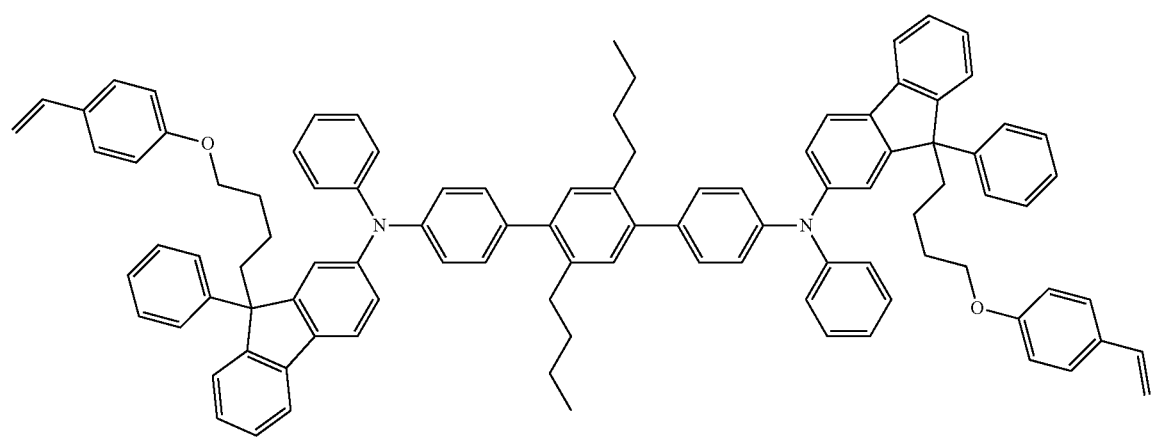
Compound 33
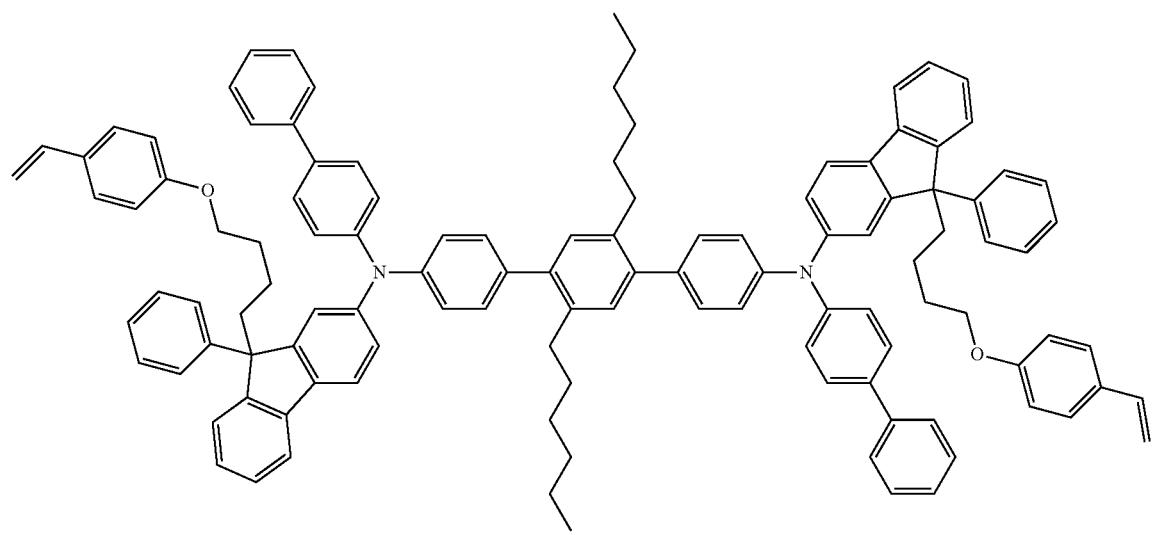

-continued
Compound 34
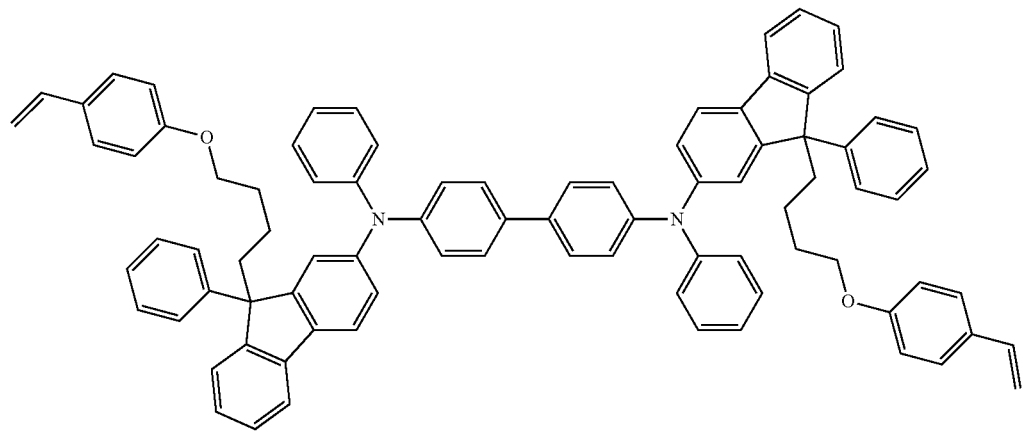
Compound 35
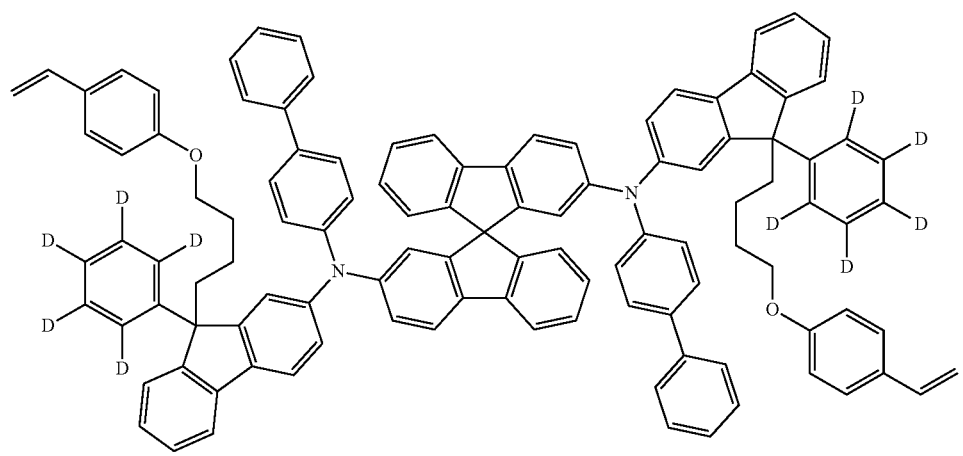
Compound 36
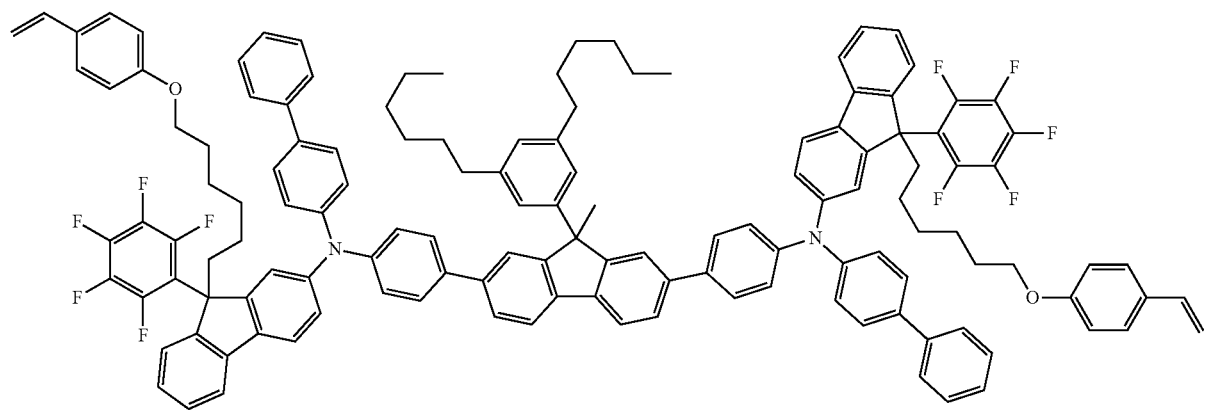

Compound 37
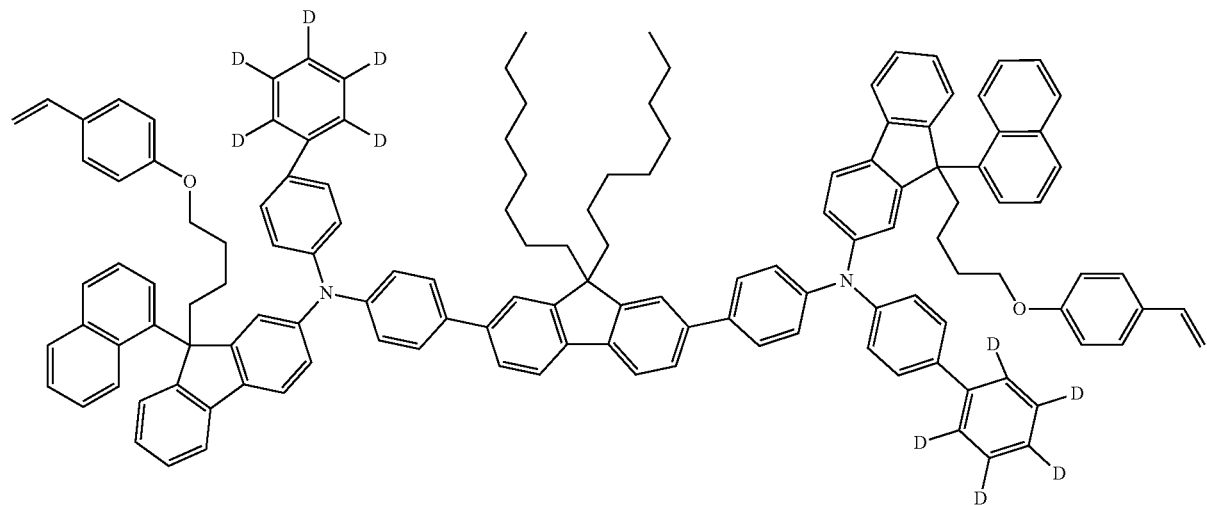
Compound 38
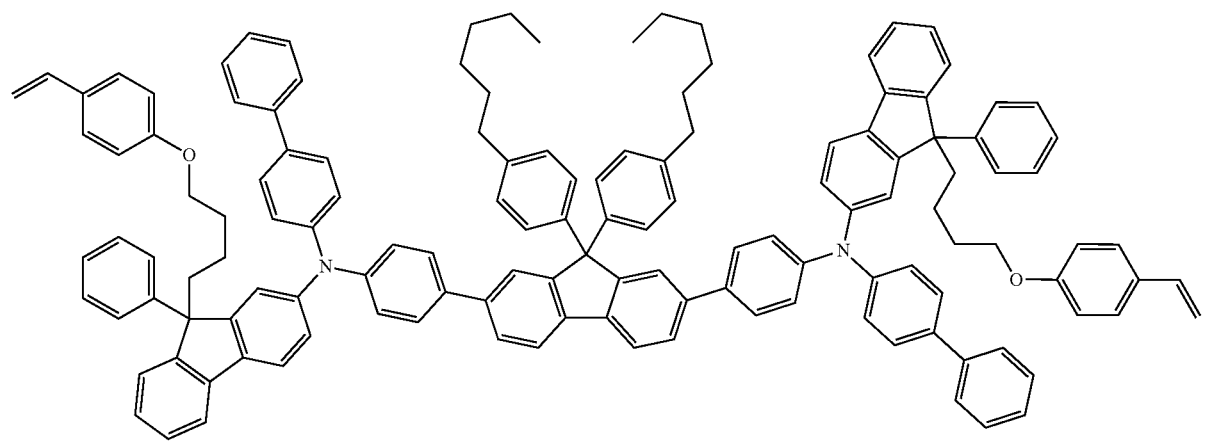
Compound 39
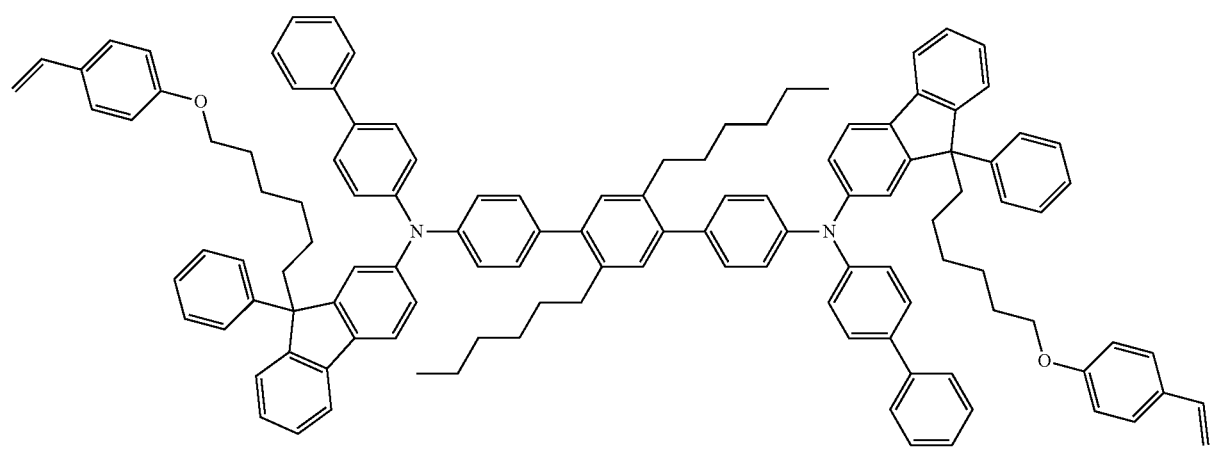

Compound 40
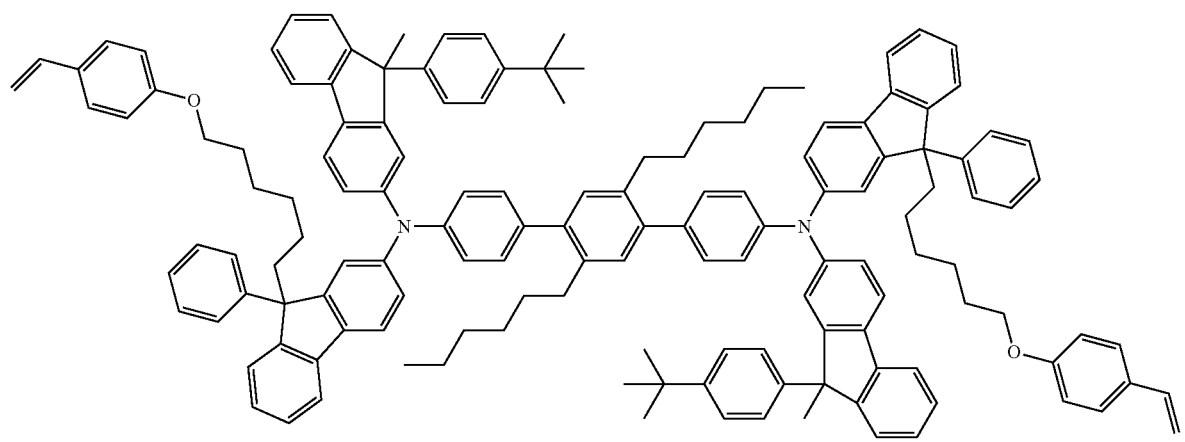
Compound 41
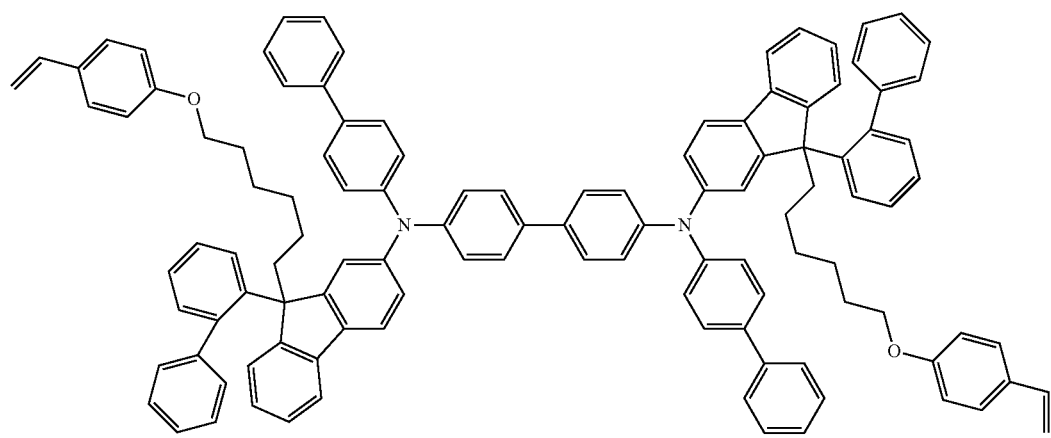
Compound 42
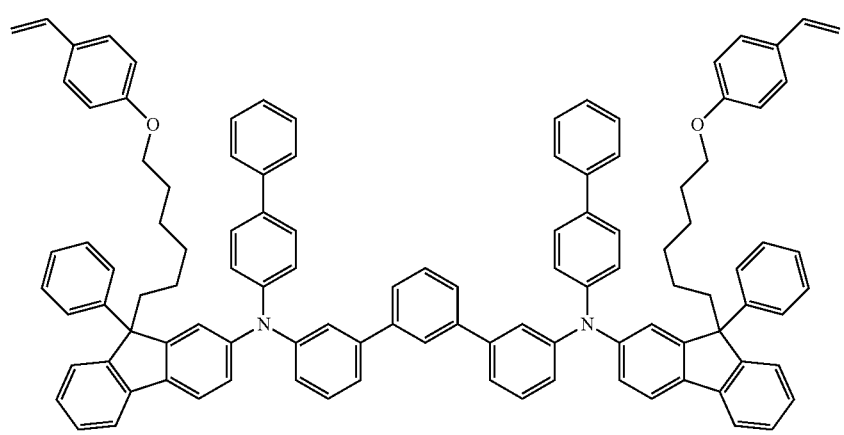

Compound 43
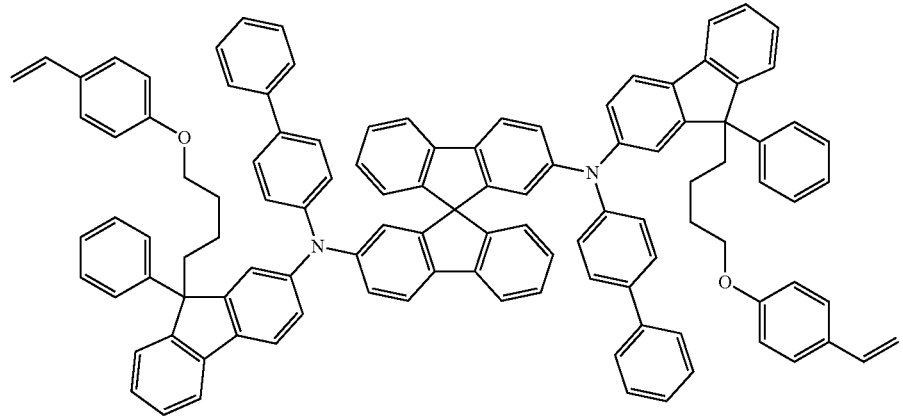
Compound 44
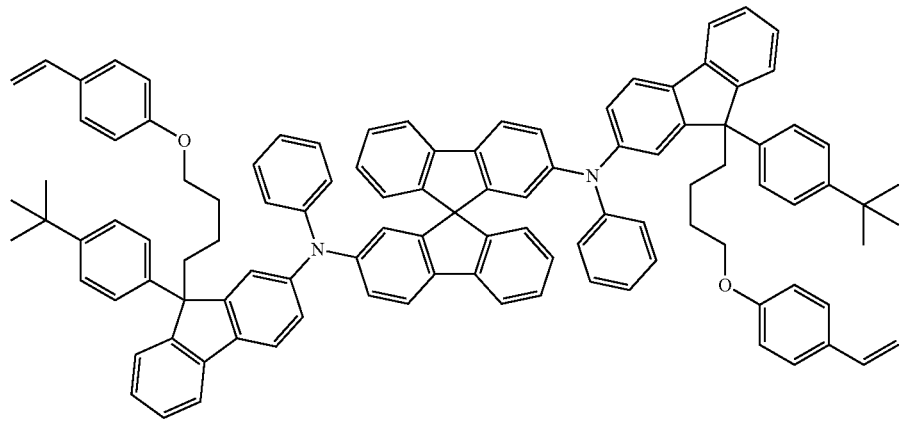
Compound 45
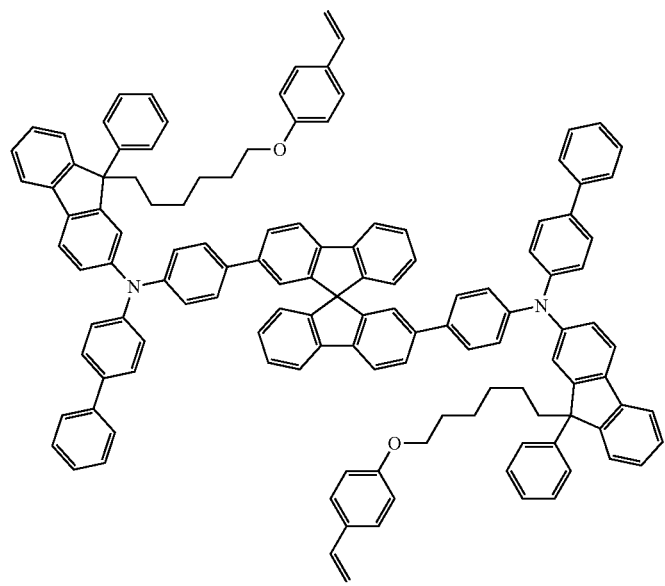

-continued
Compound 46
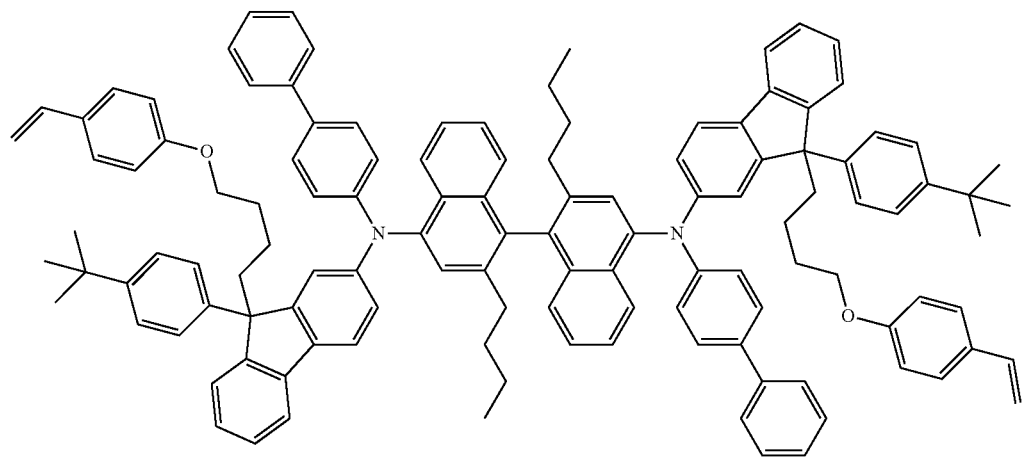
Compound 47
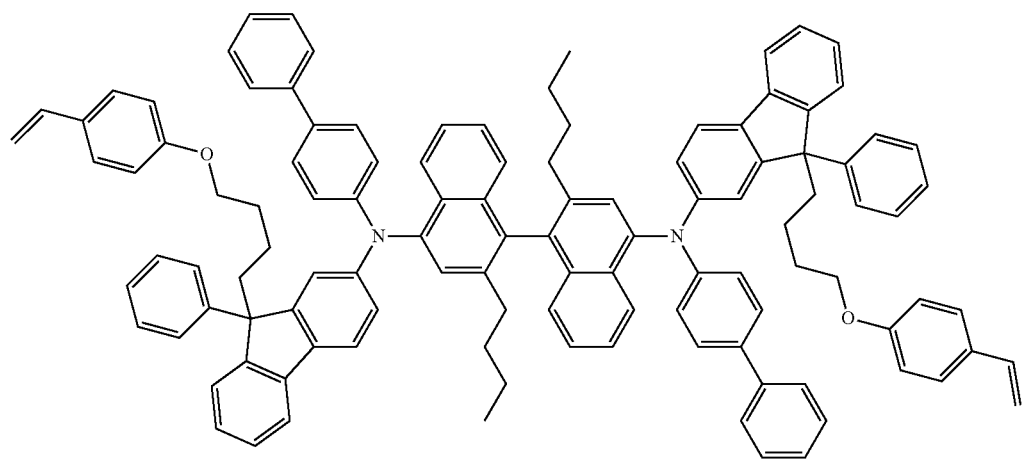
Compound 48
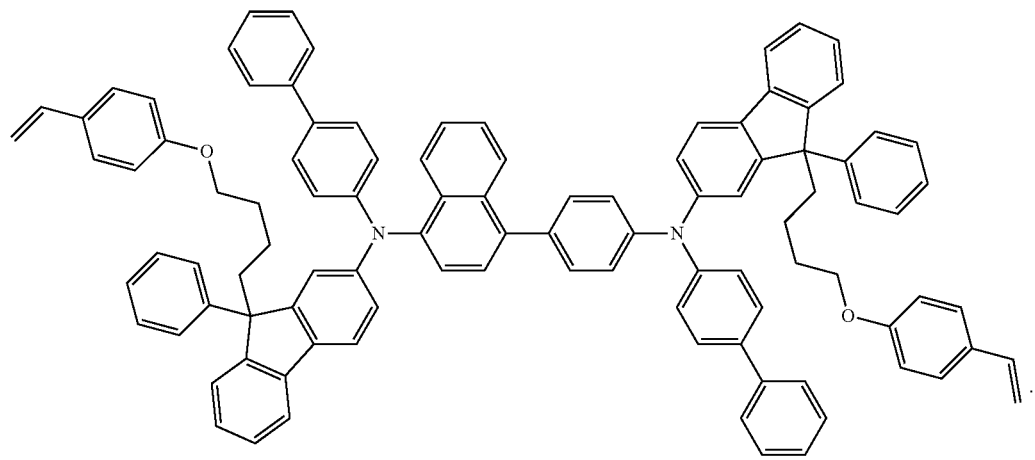

5. A coating composition comprising the fluorene-based compound of claim 1.

6. The coating composition of claim 5, further comprising:
a p-doping material.

7. The coating composition of claim 6, wherein the p-doping material is F4TCNQ; or a compound comprising a boron anion.

8. The coating composition of claim 5, further comprising:
a single molecule comprising a thermosetting group or a photocurable group; or
a single molecule comprising an end group capable of forming a polymer by heat.

9. The coating composition of claim 5, wherein the coating composition has a thin film retention rate of 95% or more in a thin film retention test, after a heat treatment at 250° C. or less.

10. An organic light emitting device comprising:
a first electrode;
a second electrode; and
an organic material layer having one or more layers provided between the first electrode and the second electrode,
wherein one or more layers of the organic material layer comprise the coating composition of claim 6 or a cured product thereof, and
the cured product of the coating composition is in a state where the coating composition is cured by a heat treatment or a light treatment.

11. The organic light emitting device of claim 10, wherein the organic material layer comprising the coating composition or the cured product thereof is a hole transport layer, a hole injection layer, or a layer which simultaneously transports and injects holes.

12. A method for manufacturing an organic light emitting device, the method comprising:
preparing a substrate;
forming a first electrode on the substrate;
forming an organic material layer having one or more layers on the first electrode; and
forming a second electrode on the organic material layer,
wherein the forming of the organic material layer comprises forming an organic material layer having one or more layers by using the coating composition of claim 5.

13. The method of claim 12, wherein the forming of the organic material layer formed by using the coating composition comprises:
coating the coating composition onto the first electrode; and
subjecting the coated coating composition to a heat treatment or a light treatment.

14. The fluorene-based compound of claim 1, wherein L is any one of the following structures:

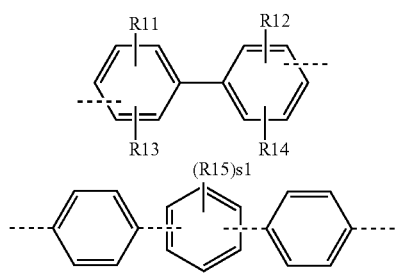

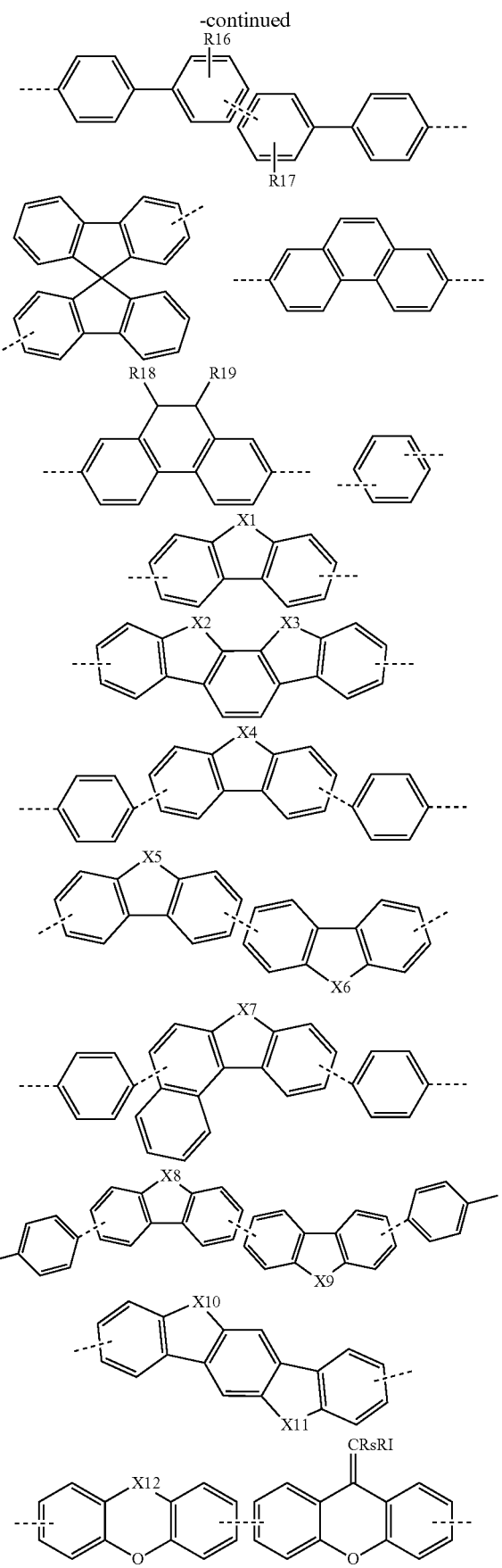

-continued

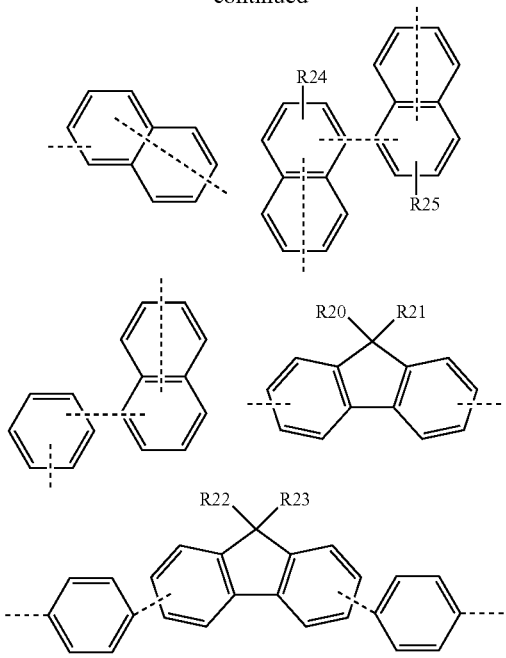

in the structures,
X12 is S, SO, CRuRv, SiRwRx or NRy,
X1 to X11 are the same as or different from each other, and are each independently O, S, SiR'R" or NR,
R11 to R25, Rs, Rt, Ru, Rv, Rw, Rx, Ry, R, R', and R" are the same as or different from each other, and are each independently hydrogen; deuterium; a halogen group; a substituted or unsubstituted alkyl group; or a substituted or unsubstituted aryl group, and
s1 is an integer of 0 to 4.

15. The fluorene-based compound of claim 1, wherein Ar1 and Ar2 are the same as or different from each other, and are each independently one of the following structures:

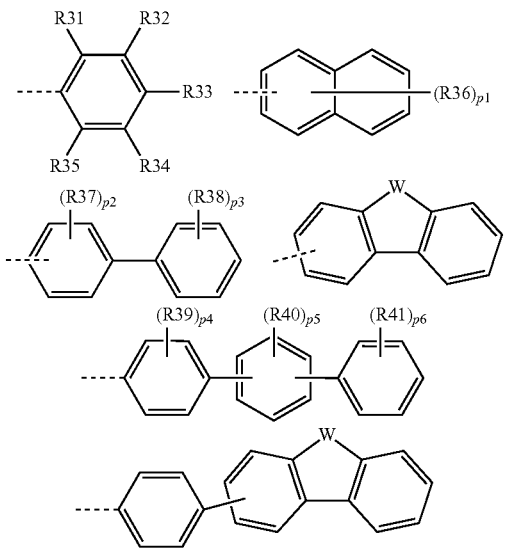

-continued

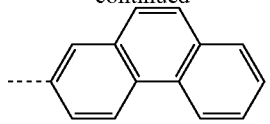

in the structures,
W is O, S, NRa, CRbRc or SiRdRe,
R31 to R41, Ra, Rb, Rc, Rd, and Re are the same as or different from each other, and are each independently hydrogen; deuterium; a halogen group; a substituted or unsubstituted alkyl group; or a substituted or unsubstituted aryl group,
p1 is an integer of 0 to 7,
p2, p4, and p5 are each an integer of 0 to 4,
p3 and p6 are each an integer of 0 to 5, and
when p1 to p6 are each 2 or more, R36s to R41s are each independently the same as or different from each other.

16. The coating composition of claim 5, further comprising a solvent.

17. The coating composition of claim 16, wherein the solvent is a chlorine-based solvent; an ether-based solvent; an aromatic hydrocarbon-based solvent; an aliphatic hydrocarbon-based solvent; a ketone-based solvent; an ester-based solvent; a polyhydric alcohol; an alcohol-based solvent; a sulfoxide-based solvent; an amide-based solvent; tetralin; or a mixture thereof.

18. The coating composition of claim 7, wherein the compound comprising a boron anion is any one of the following Formulae 4-2 to 4-3:

[Formula 4-2]

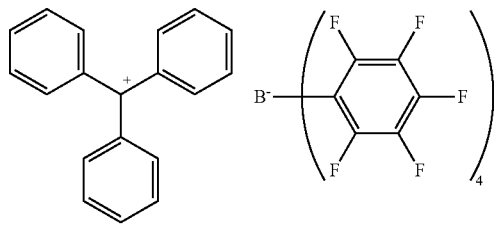

[Formula 4-3]

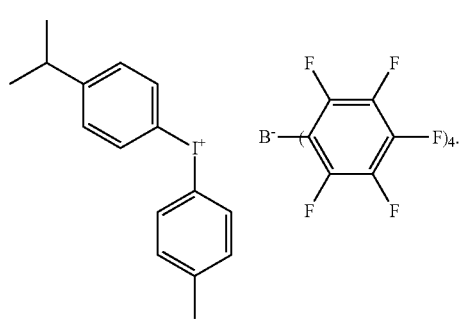

19. The coating composition of claim 6, wherein the p-doping material is present at 1 to 30 wt % based on the total content of the coating composition.

* * * * *